(12) United States Patent
Roth et al.

(10) Patent No.: US 8,449,560 B2
(45) Date of Patent: May 28, 2013

(54) DEVICES AND METHODS FOR PLACEMENT OF PARTITIONS WITHIN A HOLLOW BODY ORGAN

(75) Inventors: Alex T. Roth, Redwood City, CA (US); Andrew H. Hancock, Fremont, CA (US); Chris Pamichev, Sunnyvale, CA (US); John Gaiser, Mountain View, CA (US); Gary Weller, Los Gatos, CA (US); Christopher Julian, Los Gatos, CA (US); James Gannoe, West Milford, NJ (US); Craig Gerbi, Half Moon Bay, CA (US); Crystine M. Lee, San Francisco, CA (US)

(73) Assignees: Satiety, Inc.; Ethicon, Inc., Norwood, MA (US)

( * ) Notice: Subject to any disclaimer, the term of this patent is extended or adjusted under 35 U.S.C. 154(b) by 1394 days.

(21) Appl. No.: 11/648,708

(22) Filed: Dec. 29, 2006

(65) Prior Publication Data

US 2007/0167960 A1      Jul. 19, 2007

Related U.S. Application Data

(63) Continuation-in-part of application No. 11/324,135, filed on Dec. 29, 2005, now Pat. No. 8,252,009, which is a continuation-in-part of application No. 10/797,303, filed on Mar. 9, 2004.

(51) Int. Cl.
*A61B 17/08* (2006.01)
(52) U.S. Cl.
USPC .......... 606/151; 606/139; 606/153; 227/175.1
(58) Field of Classification Search
USPC ..................... 606/139, 151, 153; 227/175.1
See application file for complete search history.

(56) References Cited

U.S. PATENT DOCUMENTS

| 2,108,206 A | 2/1938 | Meeker |
| 2,508,690 A | 7/1948 | Schmerl |

(Continued)

FOREIGN PATENT DOCUMENTS

| AU | 2006-230695 A1 | 11/2006 |
| EP | 0 137 878 A1 | 4/1985 |

(Continued)

OTHER PUBLICATIONS

Benjamin, S.B., et al., *A Double-Blind Cross Over Study of the Garren-Edwards anti-Obesity Bubblem* Abstract Submitted to A/S/G/E/ 1987, Georgetown University Hospital and Fairfax Hospital, Washington, D.C. and Fairfax, VA.

(Continued)

*Primary Examiner* — Gary Jackson
*Assistant Examiner* — Diane Yabut
(74) *Attorney, Agent, or Firm* — Nutter McClennen & Fish LLP; William C. Geary, III

(57) ABSTRACT

Devices and methods for tissue acquisition and fixation, or gastroplasty, are described. Generally, the devices of the system may be advanced in a minimally invasive manner within a patient's body to create one or more plications within the hollow body organ. A tissue treatment device attached to a distal end of a flexible elongated member and has a cartridge member opposite an anvil member. The cartridge member and the anvil member are movable between a closed position and an open position, and a moveable barrier is disposed between the cartridge and anvil members to help acquire a dual fold of tissue. The tissue treatment device can be repositioned to form multiple plications within the organ.

29 Claims, 51 Drawing Sheets

U.S. PATENT DOCUMENTS

| | | |
|---|---|---|
| 3,372,443 A | 3/1968 | Daddona, Jr. |
| 3,395,710 A | 8/1968 | Stratton et al. |
| 3,986,493 A | 10/1976 | Hendren, III |
| 4,057,065 A | 11/1977 | Thow |
| 4,063,561 A | 12/1977 | McKenna |
| 4,133,315 A | 1/1979 | Berman et al. |
| 4,134,405 A | 1/1979 | Smit |
| 4,198,982 A | 4/1980 | Fortner et al. |
| 4,246,893 A | 1/1981 | Berson |
| 4,258,705 A | 3/1981 | Sorensen et al. |
| 4,311,146 A | 1/1982 | Wonder |
| 4,315,509 A | 2/1982 | Smit |
| 4,343,066 A | 8/1982 | Lance |
| 4,402,445 A | 9/1983 | Green |
| 4,416,267 A | 11/1983 | Garren et al. |
| 4,458,681 A | 7/1984 | Hopkins |
| 4,485,805 A | 12/1984 | Foster, Jr. |
| 4,496,288 A | 1/1985 | Nakamura et al. |
| 4,501,264 A | 2/1985 | Rockey |
| 4,547,192 A | 10/1985 | Brodsky et al. |
| 4,558,699 A | 12/1985 | Bashour |
| 4,592,339 A | 6/1986 | Kuzmak et al. |
| 4,592,354 A | 6/1986 | Rothfuss |
| 4,598,699 A | 7/1986 | Garren et al. |
| 4,607,618 A | 8/1986 | Angelchik |
| 4,610,383 A | 9/1986 | Rothfuss et al. |
| 4,636,205 A | 1/1987 | Steer |
| 4,641,653 A | 2/1987 | Rockey |
| 4,643,169 A | 2/1987 | Koss et al. |
| 4,646,722 A | 3/1987 | Silverstein et al. |
| 4,648,383 A | 3/1987 | Angelchik |
| 4,671,287 A | 6/1987 | Fiddian-Green |
| 4,694,827 A | 9/1987 | Weiner et al. |
| 4,696,288 A | 9/1987 | Kuzmak et al. |
| 4,716,900 A | 1/1988 | Ravo et al. |
| 4,723,547 A | 2/1988 | Kullas et al. |
| 4,739,758 A | 4/1988 | Lai et al. |
| 4,744,363 A | 5/1988 | Hasson |
| 4,773,393 A | 9/1988 | Haber et al. |
| 4,790,294 A | 12/1988 | Allred, III et al. |
| 4,795,430 A | 1/1989 | Quinn et al. |
| 4,803,985 A | 2/1989 | Hill |
| 4,841,888 A | 6/1989 | Mills et al. |
| 4,892,244 A | 1/1990 | Fox |
| 4,899,747 A | 2/1990 | Garren et al. |
| 4,905,693 A | 3/1990 | Ravo |
| 4,925,446 A | 5/1990 | Garay et al. |
| 4,927,428 A | 5/1990 | Richards |
| 4,969,474 A | 11/1990 | Schwarz |
| 5,037,021 A | 8/1991 | Mills et al. |
| 5,059,193 A | 10/1991 | Kuslich |
| 5,080,663 A | 1/1992 | Mills et al. |
| 5,084,061 A | 1/1992 | Gau et al. |
| 5,112,310 A | 5/1992 | Grobe |
| 5,129,915 A | 7/1992 | Cantenys |
| 5,146,933 A | 9/1992 | Boyd |
| 5,156,609 A | 10/1992 | Nakao et al. |
| 5,171,233 A | 12/1992 | Amplatz et al. |
| 5,197,649 A | 3/1993 | Bessler et al. |
| 5,220,928 A | 6/1993 | Oddsen et al. |
| 5,222,961 A | 6/1993 | Nakao et al. |
| 5,226,429 A | 7/1993 | Kuzmak |
| 5,234,454 A | 8/1993 | Bangs |
| 5,246,456 A | 9/1993 | Wilkinson |
| 5,248,302 A | 9/1993 | Patrick et al. |
| 5,250,058 A | 10/1993 | Miller et al. |
| 5,250,075 A | 10/1993 | Badie |
| 5,254,126 A | 10/1993 | Filipi et al. |
| 5,259,366 A | 11/1993 | Reydel et al. |
| 5,259,399 A | 11/1993 | Brown |
| 5,261,920 A | 11/1993 | Main et al. |
| 5,263,629 A | 11/1993 | Trumbull et al. |
| 5,284,128 A | 2/1994 | Hart |
| 5,297,536 A | 3/1994 | Wilk |
| 5,301,658 A | 4/1994 | Zhu et al. |
| 5,306,300 A | 4/1994 | Berry |
| 5,309,896 A | 5/1994 | Moll et al. |
| 5,309,927 A | 5/1994 | Welch |
| 5,327,914 A | 7/1994 | Shlain |
| 5,330,486 A | 7/1994 | Wilk |
| 5,330,503 A | 7/1994 | Yoon |
| 5,331,975 A | 7/1994 | Bonutti |
| 5,334,209 A | 8/1994 | Yoon |
| 5,334,210 A | 8/1994 | Gianturco |
| 5,345,949 A | 9/1994 | Shlain |
| 5,346,501 A | 9/1994 | Regula et al. |
| 5,355,897 A | 10/1994 | Pietrafitta et al. |
| 5,358,496 A | 10/1994 | Ortiz |
| 5,376,095 A | 12/1994 | Ortiz |
| 5,382,231 A | 1/1995 | Shlain |
| 5,403,312 A | 4/1995 | Yates et al. |
| 5,403,326 A | 4/1995 | Harrison et al. |
| 5,411,508 A | 5/1995 | Bessler et al. |
| 5,433,721 A | 7/1995 | Hooven et al. |
| 5,437,291 A | 8/1995 | Pasricha et al. |
| 5,449,368 A | 9/1995 | Kuzmak |
| 5,452,837 A | 9/1995 | Williamson, IV et al. |
| 5,458,131 A | 10/1995 | Wilk |
| 5,462,559 A | 10/1995 | Ahmed |
| 5,465,894 A | 11/1995 | Clark et al. |
| 5,467,911 A | 11/1995 | Tsuruta et al. |
| 5,486,183 A | 1/1996 | Middleman et al. |
| 5,489,058 A | 2/1996 | Plyley et al. |
| 5,503,635 A | 4/1996 | Sauer et al. |
| 5,527,319 A | 6/1996 | Green et al. |
| 5,535,935 A | 7/1996 | Vidal et al. |
| 5,542,949 A | 8/1996 | Yoon |
| 5,549,621 A | 8/1996 | Bessler et al. |
| 5,551,622 A | 9/1996 | Yoon |
| 5,555,898 A | 9/1996 | Suzuki et al. |
| 5,558,665 A | 9/1996 | Kieturakis |
| 5,571,116 A | 11/1996 | Bolanos et al. |
| 5,577,654 A | 11/1996 | Bishop |
| 5,578,044 A | 11/1996 | Gordon et al. |
| 5,582,616 A | 12/1996 | Bolduc et al. |
| 5,584,861 A | 12/1996 | Swain et al. |
| 5,588,579 A | 12/1996 | Schnut et al. |
| 5,601,604 A | 2/1997 | Vincent |
| 5,603,443 A | 2/1997 | Clark et al. |
| 5,607,094 A | 3/1997 | Clark et al. |
| 5,624,381 A | 4/1997 | Kieturakis |
| 5,626,588 A | 5/1997 | Sauer et al. |
| 5,639,008 A | 6/1997 | Gallagher et al. |
| 5,649,937 A | 7/1997 | Bito et al. |
| 5,651,769 A | 7/1997 | Waxman et al. |
| 5,655,698 A | 8/1997 | Yoon |
| 5,662,664 A | 9/1997 | Gordon et al. |
| 5,662,667 A | 9/1997 | Knodel |
| 5,667,520 A | 9/1997 | Bonutti |
| 5,676,659 A | 10/1997 | McGurk |
| 5,676,674 A | 10/1997 | Bolanos et al. |
| 5,681,263 A | 10/1997 | Flesch |
| 5,685,868 A | 11/1997 | Lundquist |
| 5,690,656 A | 11/1997 | Cope et al. |
| 5,697,943 A | 12/1997 | Sauer et al. |
| 5,707,382 A | 1/1998 | Sierocuk et al. |
| 5,722,990 A | 3/1998 | Sugarbaker et al. |
| 5,728,178 A | 3/1998 | Buffington et al. |
| 5,735,848 A | 4/1998 | Yates et al. |
| 5,749,893 A | 5/1998 | Vidal et al. |
| 5,755,730 A | 5/1998 | Swain et al. |
| 5,766,216 A | 6/1998 | Gangal et al. |
| 5,776,054 A | 7/1998 | Bobra |
| 5,782,397 A | 7/1998 | Koukline |
| 5,782,844 A | 7/1998 | Yoon et al. |
| 5,788,715 A | 8/1998 | Watson, Jr. et al. |
| 5,792,153 A | 8/1998 | Swain et al. |
| 5,797,931 A | 8/1998 | Bito et al. |
| 5,810,851 A | 9/1998 | Yoon |
| 5,810,855 A | 9/1998 | Rayburn et al. |
| 5,810,882 A | 9/1998 | Bolduc et al. |
| 5,816,471 A | 10/1998 | Plyley et al. |
| 5,820,584 A | 10/1998 | Crabb |
| 5,824,008 A | 10/1998 | Bolduc et al. |
| 5,827,298 A | 10/1998 | Hart et al. |
| 5,833,690 A | 11/1998 | Yates et al. |
| 5,836,311 A | 11/1998 | Borst et al. |

| | | | | | | |
|---|---|---|---|---|---|---|
| 5,839,639 | A | 11/1998 | Sauer et al. | 6,535,764 B2 | 3/2003 | Imran et al. |
| 5,860,581 | A | 1/1999 | Robertson et al. | 6,540,789 B1 | 4/2003 | Silverman et al. |
| 5,861,036 | A | 1/1999 | Godin | 6,551,310 B1 | 4/2003 | Ganz et al. |
| 5,868,141 | A | 2/1999 | Ellias | 6,554,844 B2 | 4/2003 | Lee et al. |
| 5,868,760 | A | 2/1999 | McGuckin, Jr. | 6,558,400 B2 * | 5/2003 | Deem et al. .................. 606/151 |
| 5,876,448 | A | 3/1999 | Thompson et al. | 6,561,969 B2 | 5/2003 | Frazier et al. |
| 5,879,371 | A | 3/1999 | Gardiner et al. | 6,572,629 B2 | 6/2003 | Kalloo et al. |
| 5,887,594 | A | 3/1999 | LoCicero, III | 6,579,301 B1 | 6/2003 | Bales et al. |
| 5,888,196 | A | 3/1999 | Bonutti | 6,592,596 B1 | 7/2003 | Geitz |
| 5,897,534 | A | 4/1999 | Heim et al. | 6,605,037 B1 | 8/2003 | Moll et al. |
| 5,897,562 | A | 4/1999 | Bolanos et al. | 6,626,899 B2 | 9/2003 | Houser et al. |
| 5,904,147 | A | 5/1999 | Conlan et al. | 6,632,227 B2 | 10/2003 | Adams |
| 5,906,625 | A | 5/1999 | Bito et al. | 6,656,194 B1 | 12/2003 | Gannoe et al. |
| 5,910,105 | A | 6/1999 | Swain et al. | 6,663,598 B1 | 12/2003 | Carrillo, Jr. et al. |
| 5,910,149 | A | 6/1999 | Kuzmak | 6,663,639 B1 | 12/2003 | Laufer et al. |
| 5,921,993 | A | 7/1999 | Yoon | 6,663,640 B2 | 12/2003 | Kortenbach |
| 5,927,284 | A | 7/1999 | Borst et al. | 6,675,809 B2 | 1/2004 | Stack et al. |
| 5,928,264 | A | 7/1999 | Sugarbaker et al. | 6,682,520 B2 | 1/2004 | Ingenito |
| 5,935,107 | A | 8/1999 | Taylor et al. | 6,689,062 B1 | 2/2004 | Mesallum |
| 5,938,669 | A | 8/1999 | Klaiber et al. | 6,692,485 B1 | 2/2004 | Brock et al. |
| 5,947,983 | A | 9/1999 | Solar et al. | 6,716,222 B2 | 4/2004 | McAlister et al. |
| 5,964,772 | A | 10/1999 | Bolduc et al. | 6,733,512 B2 | 5/2004 | McGhan |
| 5,964,782 | A | 10/1999 | Lafontaine et al. | 6,736,822 B2 | 5/2004 | McClellan et al. |
| 5,972,001 | A | 10/1999 | Yoon | 6,740,098 B2 | 5/2004 | Abrams et al. |
| 5,972,002 | A | 10/1999 | Bark et al. | 6,740,121 B2 | 5/2004 | Geitz |
| 5,976,161 | A | 11/1999 | Kirsch et al. | 6,746,460 B2 | 6/2004 | Gannoe et al. |
| 5,980,537 | A | 11/1999 | Ouchi | 6,746,489 B2 | 6/2004 | Dua et al. |
| 5,993,464 | A | 11/1999 | Knodel | 6,754,536 B2 | 6/2004 | Swoyer et al. |
| 5,993,473 | A | 11/1999 | Chan et al. | 6,755,849 B1 | 6/2004 | Gowda et al. |
| 6,015,378 | A | 1/2000 | Borst et al. | 6,755,869 B2 | 6/2004 | Geitz |
| 6,030,364 | A | 2/2000 | Durgin et al. | 6,756,364 B2 | 6/2004 | Barbier et al. |
| 6,030,392 | A | 2/2000 | Dakov | 6,764,518 B2 | 7/2004 | Godin |
| 6,042,538 | A | 3/2000 | Puskas | 6,773,440 B2 | 8/2004 | Gannoe et al. |
| 6,044,847 | A | 4/2000 | Carter et al. | 6,773,441 B1 | 8/2004 | Laufer et al. |
| 6,067,991 | A | 5/2000 | Forsell | 6,786,898 B2 | 9/2004 | Guenst |
| 6,074,343 | A | 6/2000 | Nathanson et al. | 6,790,214 B2 | 9/2004 | Kraemer et al. |
| 6,083,241 | A | 7/2000 | Longo et al. | 6,802,868 B2 | 10/2004 | Silverman et al. |
| 6,086,600 | A | 7/2000 | Kortenbach | 6,821,285 B2 | 11/2004 | Laufer et al. |
| 6,113,609 | A | 9/2000 | Adams | 6,830,546 B1 | 12/2004 | Chin et al. |
| 6,119,913 | A | 9/2000 | Adams et al. | 6,835,199 B2 | 12/2004 | McGuckin, Jr. et al. |
| 6,120,513 | A | 9/2000 | Bailey et al. | 6,835,200 B2 | 12/2004 | Laufer et al. |
| 6,136,006 | A | 10/2000 | Johnson et al. | 6,837,848 B2 | 1/2005 | Bonner et al. |
| 6,159,146 | A | 12/2000 | El Gazayerli | 6,840,423 B2 | 1/2005 | Adams et al. |
| 6,159,195 | A | 12/2000 | Ha et al. | 6,845,776 B2 | 1/2005 | Stack et al. |
| 6,165,183 | A | 12/2000 | Kuehn et al. | 6,896,682 B1 | 5/2005 | McClellan et al. |
| 6,179,195 | B1 | 1/2001 | Adams et al. | 6,916,332 B2 | 7/2005 | Adams |
| 6,186,942 | B1 | 2/2001 | Sullivan et al. | 6,926,722 B2 | 8/2005 | Geitz |
| 6,186,985 | B1 | 2/2001 | Snow | 6,966,919 B2 | 11/2005 | Sixto, Jr. et al. |
| 6,197,022 | B1 | 3/2001 | Baker | 6,981,978 B2 | 1/2006 | Gannoe |
| 6,200,318 | B1 | 3/2001 | Har-Shai et al. | 6,991,643 B2 | 1/2006 | Saadat |
| 6,206,822 | B1 | 3/2001 | Foley et al. | 6,994,715 B2 | 2/2006 | Gannoe et al. |
| 6,206,893 | B1 | 3/2001 | Klein et al. | 7,020,531 B1 | 3/2006 | Colliou et al. |
| 6,224,614 | B1 | 5/2001 | Yoon | 7,025,791 B2 | 4/2006 | Levine et al. |
| 6,231,561 | B1 | 5/2001 | Frazier et al. | 7,033,373 B2 | 4/2006 | de al Torre et al. |
| 6,248,058 | B1 | 6/2001 | Silverman et al. | 7,033,378 B2 | 4/2006 | Smith et al. |
| 6,254,642 | B1 | 7/2001 | Taylor | 7,033,384 B2 | 4/2006 | Gannoe et al. |
| 6,273,897 | B1 | 8/2001 | Dalessandro et al. | 7,037,343 B2 | 5/2006 | Imran |
| 6,279,809 | B1 | 8/2001 | Nicolo | 7,037,344 B2 | 5/2006 | Kagan et al. |
| 6,290,674 | B1 | 9/2001 | Roue et al. | 7,063,715 B2 | 6/2006 | Onuki et al. |
| 6,293,923 | B1 | 9/2001 | Yachia et al. | 7,074,229 B2 | 7/2006 | Adams et al. |
| 6,302,917 | B1 | 10/2001 | Dua et al. | 7,083,629 B2 | 8/2006 | Weller et al. |
| 6,312,437 | B1 | 11/2001 | Kortenbach | 7,083,630 B2 | 8/2006 | DeVries et al. |
| 6,328,689 | B1 | 12/2001 | Gonzalez et al. | 7,087,011 B2 | 8/2006 | Cabiri et al. |
| 6,338,345 | B1 | 1/2002 | Johnson et al. | 7,097,650 B2 | 8/2006 | Weller et al. |
| 6,352,543 | B1 | 3/2002 | Cole | 2001/0014800 A1 | 8/2001 | Frazier et al. |
| 6,358,197 | B1 | 3/2002 | Silverman et al. | 2001/0020190 A1 | 9/2001 | Taylor |
| 6,379,366 | B1 | 4/2002 | Fleischman et al. | 2001/0037127 A1 | 11/2001 | De Hoyos Garza |
| 6,387,104 | B1 | 5/2002 | Pugsley, Jr. et al. | 2002/0022851 A1 | 2/2002 | Kalloo et al. |
| 6,398,795 | B1 | 6/2002 | McAlister et al. | 2002/0035361 A1 | 3/2002 | Houser et al. |
| 6,416,535 | B1 | 7/2002 | Lazarus | 2002/0040226 A1 | 4/2002 | Laufer et al. |
| 6,423,087 | B1 | 7/2002 | Sawada | 2002/0047036 A1 | 4/2002 | Sullivan et al. |
| 6,432,040 | B1 | 8/2002 | Meah | 2002/0058967 A1 | 5/2002 | Jervis |
| 6,447,533 | B1 | 9/2002 | Adams | 2002/0072761 A1 | 6/2002 | Abrams et al. |
| 6,460,543 | B1 | 10/2002 | Forsell | 2002/0077661 A1 | 6/2002 | Saadat |
| 6,475,136 | B1 | 11/2002 | Forsell | 2002/0078967 A1 | 6/2002 | Sixto, Jr. et al. |
| 6,478,791 | B1 | 11/2002 | Carter et al. | 2002/0082621 A1 | 6/2002 | Schurr et al. |
| 6,491,707 | B2 | 12/2002 | Makower et al. | 2002/0143346 A1 | 10/2002 | McGuckin, Jr. et al. |
| 6,494,888 | B1 | 12/2002 | Laufer et al. | 2002/0165589 A1 | 11/2002 | Imran et al. |
| 6,506,196 | B1 | 1/2003 | Laufer | 2002/0183768 A1 | 12/2002 | Deem et al. |

| | | |
|---|---|---|
| 2002/0193816 A1 | 12/2002 | Laufer et al. |
| 2003/0040804 A1 | 2/2003 | Stack et al. |
| 2003/0040808 A1 | 2/2003 | Stack et al. |
| 2003/0065340 A1 | 4/2003 | Geitz |
| 2003/0065359 A1 | 4/2003 | Weller et al. |
| 2003/0093117 A1 | 5/2003 | Saadat |
| 2003/0109892 A1 | 6/2003 | Deem et al. |
| 2003/0109931 A1 | 6/2003 | Geitz |
| 2003/0109935 A1 | 6/2003 | Geitz |
| 2003/0120265 A1 | 6/2003 | Deem et al. |
| 2003/0120285 A1 | 6/2003 | Kortenbach |
| 2003/0120289 A1 | 6/2003 | McGuckin, Jr. et al. |
| 2003/0132267 A1 | 7/2003 | Adams et al. |
| 2003/0158563 A1 | 8/2003 | McClellan et al. |
| 2003/0158601 A1 | 8/2003 | Silverman et al. |
| 2003/0171760 A1 | 9/2003 | Gambale |
| 2003/0208209 A1 | 11/2003 | Gambale et al. |
| 2003/0216754 A1 | 11/2003 | Kraemer et al. |
| 2003/0225312 A1 | 12/2003 | Suzuki et al. |
| 2004/0006351 A1 | 1/2004 | Gannoe et al. |
| 2004/0009224 A1 | 1/2004 | Miller |
| 2004/0010271 A1 | 1/2004 | Kortenbach |
| 2004/0024386 A1 | 2/2004 | Deem et al. |
| 2004/0037865 A1 | 2/2004 | Miller |
| 2004/0039452 A1 | 2/2004 | Bessler |
| 2004/0044354 A1 | 3/2004 | Gannoe et al. |
| 2004/0049209 A1 | 3/2004 | Benchetrit |
| 2004/0059349 A1 | 3/2004 | Sixto, Jr. et al. |
| 2004/0059354 A1 | 3/2004 | Smith et al. |
| 2004/0059358 A1 | 3/2004 | Kortenbach et al. |
| 2004/0082963 A1 | 4/2004 | Gannoe et al. |
| 2004/0087977 A1 | 5/2004 | Nolan et al. |
| 2004/0088008 A1 | 5/2004 | Gannoe et al. |
| 2004/0089313 A1 | 5/2004 | Utley et al. |
| 2004/0092892 A1 | 5/2004 | Kagan et al. |
| 2004/0092974 A1 | 5/2004 | Gannoe et al. |
| 2004/0097989 A1 | 5/2004 | Molina Trigueros |
| 2004/0107004 A1 | 6/2004 | Levine et al. |
| 2004/0116949 A1 | 6/2004 | Ewers et al. |
| 2004/0122456 A1 | 6/2004 | Saadat et al. |
| 2004/0122473 A1 | 6/2004 | Ewers et al. |
| 2004/0122526 A1 | 6/2004 | Imran |
| 2004/0133147 A1 | 7/2004 | Woo |
| 2004/0133238 A1 | 7/2004 | Cerier |
| 2004/0138525 A1 | 7/2004 | Saadat |
| 2004/0138526 A1 | 7/2004 | Guenst |
| 2004/0138529 A1 | 7/2004 | Wiltshire et al. |
| 2004/0138531 A1 | 7/2004 | Bonner et al. |
| 2004/0138682 A1 | 7/2004 | Onuki et al. |
| 2004/0147958 A1 | 7/2004 | Lam et al. |
| 2004/0148021 A1 | 7/2004 | Cartledge et al. |
| 2004/0148034 A1 | 7/2004 | Kagan et al. |
| 2004/0158331 A1 | 8/2004 | Stack et al. |
| 2004/0162568 A1 | 8/2004 | Saadat |
| 2004/0167546 A1 | 8/2004 | Saadat et al. |
| 2004/0172141 A1 | 9/2004 | Stack et al. |
| 2004/0181242 A1 | 9/2004 | Stack et al. |
| 2004/0193190 A1* | 9/2004 | Liddicoat et al. ............ 606/153 |
| 2004/0194157 A1 | 9/2004 | Meguid |
| 2004/0194790 A1 | 10/2004 | Laufer et al. |
| 2004/0210243 A1* | 10/2004 | Gannoe et al. ............... 606/151 |
| 2004/0215180 A1 | 10/2004 | Starkebaum et al. |
| 2004/0220682 A1 | 11/2004 | Levine et al. |
| 2004/0225183 A1 | 11/2004 | Michlitsch et al. |
| 2004/0225194 A1 | 11/2004 | Smith et al. |
| 2004/0225305 A1 | 11/2004 | Ewers et al. |
| 2004/0236357 A1 | 11/2004 | Kraemer et al. |
| 2004/0249362 A1 | 12/2004 | Levine et al. |
| 2005/0010162 A1 | 1/2005 | Utley et al. |
| 2005/0021681 A1 | 1/2005 | Oommen |
| 2005/0033328 A1 | 2/2005 | Laufer et al. |
| 2005/0038415 A1 | 2/2005 | Rohr et al. |
| 2005/0038462 A1 | 2/2005 | Lubock |
| 2005/0049718 A1 | 3/2005 | Dann et al. |
| 2005/0055038 A1* | 3/2005 | Kelleher et al. ............... 606/151 |
| 2005/0055039 A1 | 3/2005 | Burnett et al. |
| 2005/0075622 A1 | 4/2005 | Levine et al. |
| 2005/0075653 A1 | 4/2005 | Saadat et al. |
| 2005/0080438 A1 | 4/2005 | Weller et al. |
| 2005/0080444 A1 | 4/2005 | Kraemer et al. |
| 2005/0085787 A1 | 4/2005 | Laufer |
| 2005/0096673 A1 | 5/2005 | Stack et al. |
| 2005/0096750 A1 | 5/2005 | Kagan et al. |
| 2005/0119671 A1 | 6/2005 | Reydel et al. |
| 2005/0119674 A1 | 6/2005 | Gingras |
| 2005/0143760 A1 | 6/2005 | Imran |
| 2005/0148818 A1 | 7/2005 | Mesallum |
| 2005/0149067 A1 | 7/2005 | Takemoto et al. |
| 2005/0149114 A1 | 7/2005 | Cartledge et al. |
| 2005/0177176 A1 | 8/2005 | Gerbi et al. |
| 2005/0192599 A1 | 9/2005 | Demarais |
| 2005/0192601 A1 | 9/2005 | Demarais |
| 2005/0194038 A1 | 9/2005 | Brabec et al. |
| 2005/0194294 A1 | 9/2005 | Oexle et al. |
| 2005/0194312 A1 | 9/2005 | Niemeyer et al. |
| 2005/0195925 A1 | 9/2005 | Traber |
| 2005/0195944 A1 | 9/2005 | Bartels et al. |
| 2005/0196356 A1 | 9/2005 | Leinen et al. |
| 2005/0197540 A1 | 9/2005 | Liedtke |
| 2005/0197622 A1 | 9/2005 | Blumenthal et al. |
| 2005/0197684 A1 | 9/2005 | Koch |
| 2005/0198476 A1 | 9/2005 | Gazsi et al. |
| 2005/0203547 A1 | 9/2005 | Weller et al. |
| 2005/0203548 A1 | 9/2005 | Weller et al. |
| 2005/0228415 A1 | 10/2005 | Gertner |
| 2005/0228504 A1 | 10/2005 | Demarais |
| 2005/0256533 A1 | 11/2005 | Roth et al. |
| 2005/0256587 A1 | 11/2005 | Egan |
| 2006/0020247 A1 | 1/2006 | Kagan et al. |
| 2006/0020254 A1 | 1/2006 | Hoffmann |
| 2006/0020276 A1 | 1/2006 | Saadat et al. |
| 2006/0036267 A1 | 2/2006 | Saadat et al. |
| 2006/0106288 A1 | 5/2006 | Roth et al. |
| 2006/0111735 A1 | 5/2006 | Crainich |
| 2006/0122462 A1 | 6/2006 | Roth et al. |
| 2006/0142787 A1 | 6/2006 | Weller et al. |
| 2006/0151568 A1 | 7/2006 | Weller et al. |
| 2007/0233161 A1 | 10/2007 | Weller et al. |

FOREIGN PATENT DOCUMENTS

| | | |
|---|---|---|
| EP | 0 174 843 A1 | 3/1986 |
| EP | 0 246 999 A1 | 11/1987 |
| EP | 0 540 010 A2 | 5/1993 |
| EP | 0668057 A2 | 8/1995 |
| EP | 1728475 A2 | 12/2006 |
| JP | 63302863 A | 9/1988 |
| JP | 63277063 A | 11/1988 |
| JP | 63279854 | 11/1988 |
| JP | 01049572 A | 2/1989 |
| JP | 04297219 | 10/1992 |
| WO | WO 94/18893 A1 | 9/1994 |
| WO | WO 99/17662 A1 | 4/1999 |
| WO | WO 99/53827 A1 | 10/1999 |
| WO | WO 00/32137 A1 | 6/2000 |
| WO | WO 00/39708 A1 | 7/2000 |
| WO | WO 00/48656 A1 | 8/2000 |
| WO | WO 00/78227 A1 | 12/2000 |
| WO | WO 00/78229 A1 | 12/2000 |
| WO | WO 01/66018 A1 | 9/2001 |
| WO | WO 01/67964 A2 | 9/2001 |
| WO | WO 01/85034 A1 | 11/2001 |
| WO | WO 02/24080 A2 | 3/2002 |
| WO | WO 02/35980 A2 | 5/2002 |
| WO | WO 02/39880 A2 | 5/2002 |
| WO | WO 02/071951 A1 | 9/2002 |
| WO | WO 02/091961 A1 | 11/2002 |
| WO | WO 02/096327 A2 | 12/2002 |
| WO | WO 03/007796 A2 | 1/2003 |
| WO | WO 03/017882 A2 | 3/2003 |
| WO | WO 03/078721 A2 | 9/2003 |
| WO | WO 03/086247 A1 | 10/2003 |
| WO | WO 03/088844 A1 | 10/2003 |
| WO | WO 03/094785 A1 | 11/2003 |
| WO | WO 03/099140 A1 | 12/2003 |
| WO | WO 03/105563 A2 | 12/2003 |
| WO | WO 03/105671 A2 | 12/2003 |
| WO | WO 2004/009269 A2 | 1/2004 |
| WO | WO 2004/014237 A1 | 2/2004 |

| | | |
|---|---|---|
| WO | 2004/019788 A2 | 3/2004 |
| WO | WO 2004/017863 A2 | 3/2004 |
| WO | WO 2004/019787 A2 | 3/2004 |
| WO | WO 2004/019826 A1 | 3/2004 |
| WO | WO 2004/037064 A2 | 5/2004 |
| WO | WO 2004/049911 A2 | 6/2004 |
| WO | WO 2004/058102 A2 | 7/2004 |
| WO | WO 2004/060150 A1 | 7/2004 |
| WO | WO 2004/087014 A2 | 10/2004 |
| WO | WO 2004/103189 A1 | 12/2004 |
| WO | WO 2005/023118 A1 | 3/2005 |
| WO | WO 2005/037152 A1 | 4/2005 |
| WO | WO 2005/058239 A2 | 6/2005 |
| WO | WO 2005/060882 A1 | 7/2005 |
| WO | 2005/092210 A1 | 10/2005 |
| WO | 2005092210 A1 | 10/2005 |
| WO | WO 2006/078781 A1 | 7/2006 |
| WO | 2006/112849 A1 | 10/2006 |

OTHER PUBLICATIONS

Benjamin, S.B., *Small Bowel Obstruction and the Garren-Edwards Bubble, Lessons to be Learned*? Abstracts Submitted to A/S/G/E 1987, Division of Gastroenterology, Department of Medicine, Georgetown University Hospital, Washington, D.C.

Boyle, Thomas M., M.D., et al., Small Intestinal Obstruction Secondary to Obturation by a Garren Gastric Bubble, *The American Journal of Gastroenterology*, vol. 82, No. 1, pp. 51-53, 1987.

Büchler, M.W., M.D. et al., A Technique for Gastroplasty as a Substitute for the Esophagus: Fundus Rotation Gastroplasty, *Journal of the American College of Surgeons*, vol. 182, pp. 241-245, Mar. 1996.

Cass, O.W., et al., *Long-Term Follow-Up of Patients With Percutaneous Endoscopic Gastrostomy (PEG)*, Abstracts Submitted to A/S/G/E 1987, Department of Medicine, Hennepin County Medical Center, Minneapolis, MN 55415.

Chang, Craig G. M.D., et al.. Gastro-Clip® Gastroplasty: A Very Long-Term Complication, *Obesity Surgery*, 14, © FD-Communications Inc.. 2004.

Clark, Charlene, R.N., The Gastric Bubble: Medicine, Magic or Mania? *SGA Journal*, vol. 9, No. 2, pp. 45-47, Fall 1986.

Cummings, David E., M.D., et al., Plasma Ghrelin Levels After Diet-Induced Weight Loss or Gastric Bypass Surgery, *New England Journal of Medicine*, vol. 346, No. 21, pp. 1623-1630, May 23, 2002.

Davenport, Horace W., Ph.D., D.Sc., *Physiology of the Digestive Tract: An Introductory Text*, 3d Ed., Cover and Table of Contents.

DeMeester, Tom T., M.D., Evolving Concepts of Reflux: The Ups and Downs of the LES, *Canadian Journal of Gastroenterology*, vol. 16, No. 5, pp. 327-331, 2002.

De Waele, B., M.D., et al., Intragastric Balloons for Preoperative Weight Reduction, *Obesity Surgery*, vol. 10, pp. 58-60, 2000.

Edell, Steven L., et al., Radiographic Evaluation of the Garren Gastric Bubble, *American Journal of Radiology*, vol. 145, pp. 49-50, Jul. 1985.

Endo Gia *Universal, Single UseStapler and Endo GIA Roticulator*, Brochure, 8 pages, Undated.

Filipi, Charles J. M.D., et al., Transoral, Flexible Endoscopic Suturing for Treatment of GERD: A Multicenter Trial, *Gastrointestinal Endoscopy*,. vol. 53, No. 4, pp. 416-422, 2001.

Gray, Henry, R.R.S., Anatomy of the Human Body, *The Digestive System*, Thirtieth American Edition, pp. 1466-1467 (Undated).

Guidant, Internet, Axius™ Vacuum 2 Stabilizer Systems, Internet Website—www.guidant.com/products/axius_vacuum.shtml, 8 pages, visited May 27, 2003.

Gukovsky-Reicher, S., M.D. et al., *Expandable Metal Esophageal Stents: Efficacy and Safety. Review of Current Literature Data and of 53 Stents Placed at Harbor-UCLA Medical Center*, www.medscape.com/viewarticle/423508_print pp. 1-20, Medscape General Medicine 4(1), 2003 © 2002 Medscape, downloaded Oct. 9, 2006.

Hepworth, Clive C. FRCS et al., Mechanical Endoscopic Methods of Haemostasis for Bleeding Peptic Ulcers: A Review, *Bailliere's Clinical Gastroenterology*, vol. 14, No. 3 pp. 467-476, 2000.

Ikeda, Y. et al., New Suturing Device for Transanal Endoscopic Microsurgery, *Blackwell Science Ltd*. p. 1290, 1997.

Johnson & Johnson[SM] Gateway Endopath 3mm, 5mm and 10 mm Diameter Endoscopic Instruments, Internet Website—www.inigateway.com/home.ihtml?loc=USENG&page=viewContent&parentId-0900 . . . , 3 pages, visited May 29, 2003.

Kirby, Donald F., Incomplete Small Bowel Obstruction by the Garren-Edwards Gastric Bubble Necessitating Surgical Intervention, *The American Journal of Gastroenterology*, vol. 82, No. 3, pp. 251-253, 1987.

Nieben, Ole Gyring, et al., Intragastric Balloon as an Artificial Bezoar for Treatment of Obesity, *The Lancet*, pp. 198-199, Jan. 23, 1982.

Percival, Walter L., M.D., "The Balloon Diet": A Noninvasive Treatment for Morbid Obesity. Preliminary Report of 1908 Patients, *The Canadian Journal of Surgery*, vol. 27, No. 2, pp. 135-136.

Power Medical Interventions Digital and Wireless Medical Technology, Product Innovation: SurgASSIST™ , Internet Website—www/pmi2.com/access_flexibility.asp, 6 pages, visited May 29, 2003.

Snowden Pencer, Diamon-Flex Angled Snake Retractor, Appendix F.f, Undated.

Stoltenberg, P.H., et al., *Intragastric Balloon Therapy of Obesity: A Randomized Double-Blind Trial*, Abstracts of Papers 1985, Scott & White Clinic, Texas A&M College of Medicine, Temple, Texas.

Swain, C. Paul, M.D. et al., An Endoscopic Sewing Machine, *Gastrointestinal Edoscopy*, vol. 32, No. 1 pp. 36-38 1986.

Swain, C. Paul, M.D., Endoscopic Sewing and Stapling Machines, *Endoscopy* pp. 205-210, © Georg Thieme Verlag Stuttgart, New York, 1997.

Swain, C. Paul, M.D. et al., An Endoscopic Stapling Device: The Development of a New Flexible Endoscopically Controlled Device for Placing Multiple Transmural Staples in Gastrointestinal Tissue, *Gastrointestinal Endoscopy*, vol. 35, No. 4, pp. 338-339, 1989.

Swain, C. Paul, M.D., Endoscopic Suturing, *Bailliere's Clinical Gastroenterology*, Bailliere's Tindall,, vol. 13 No. 1, pp. 97-108, 1999.

Taylor, T. Vincent, et al., Gastric Balloons for Obesity, *The Lancet*, Abstract, Mar. 27, 1982.

Vandenplas, Y., et al., Intragastric Balloons in Adolescents With Morbid Obesity, *European Journal of Gastroenterology & Hepatology*, vol. 11, No. 3, pp. 243-245, 1999.

Villar, Hugo V., M.D., et al., Mechanisms of Satiety and Gastric Emptying After Gastric Partitioning and Bypass, *Surgery*, pp. 229-236, Aug. 1981.

Wullstein, C., et al., Compression Anastomosis (AKA-2) in Colorectal Surgery: Results in 442 Consecutive Patients, *British Journal of Surgery 2000*, pp. 1071-1075.

Gukovsky-Reicher, S. , M.D. et al., "Expandable Metal Esophageal Stents: Efficacy and Safety", Review of Current Literature Data and of 53 Stents Placed at Harbor-UCLA Medical Center, www.medscape.com/viewartcle, 20 pgs. downloaded Aug. 24, 2002.

Taylor, T. V., et al., "Gastric Baloons for Obesity", The Lancet, Mar. 27, 1982, p. 750.

* cited by examiner

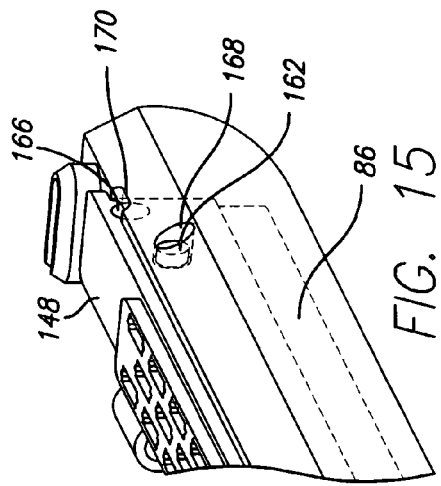
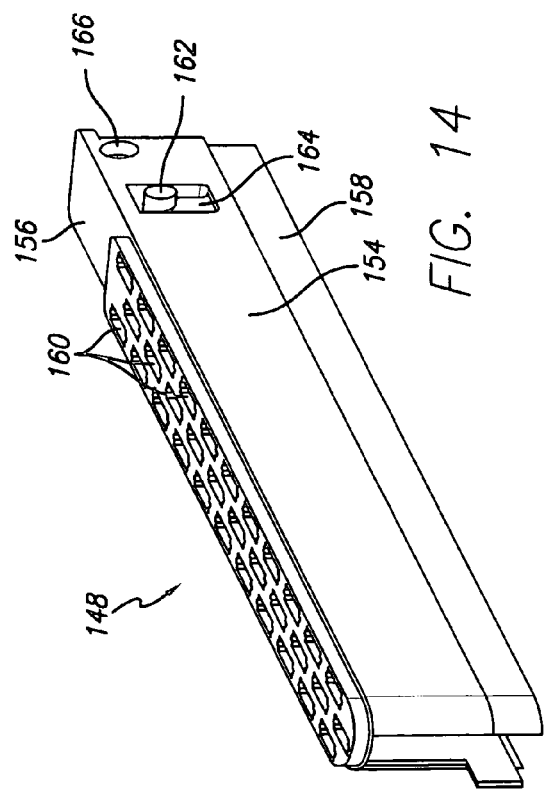
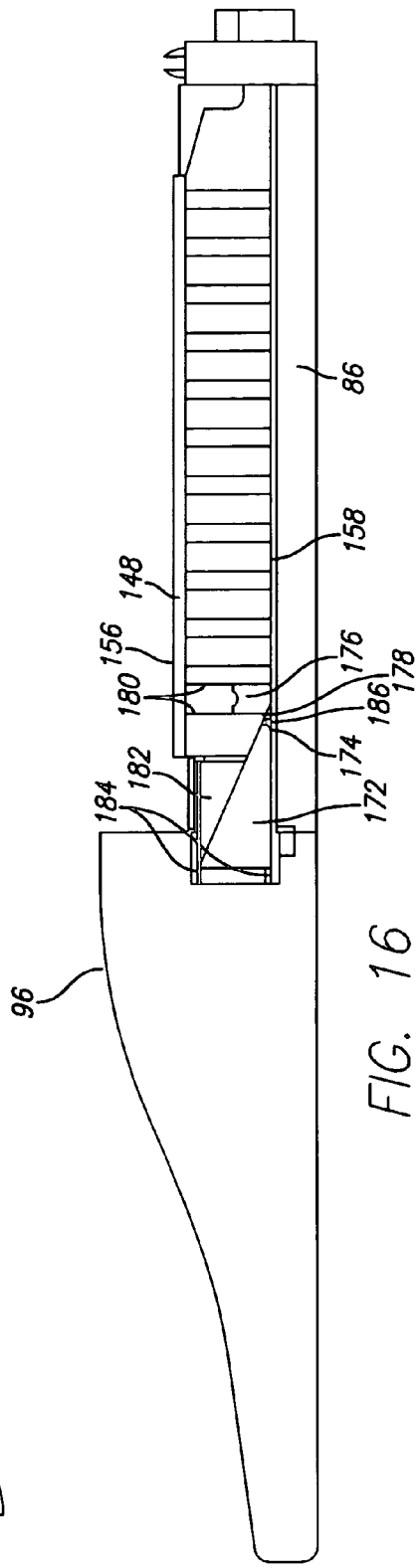

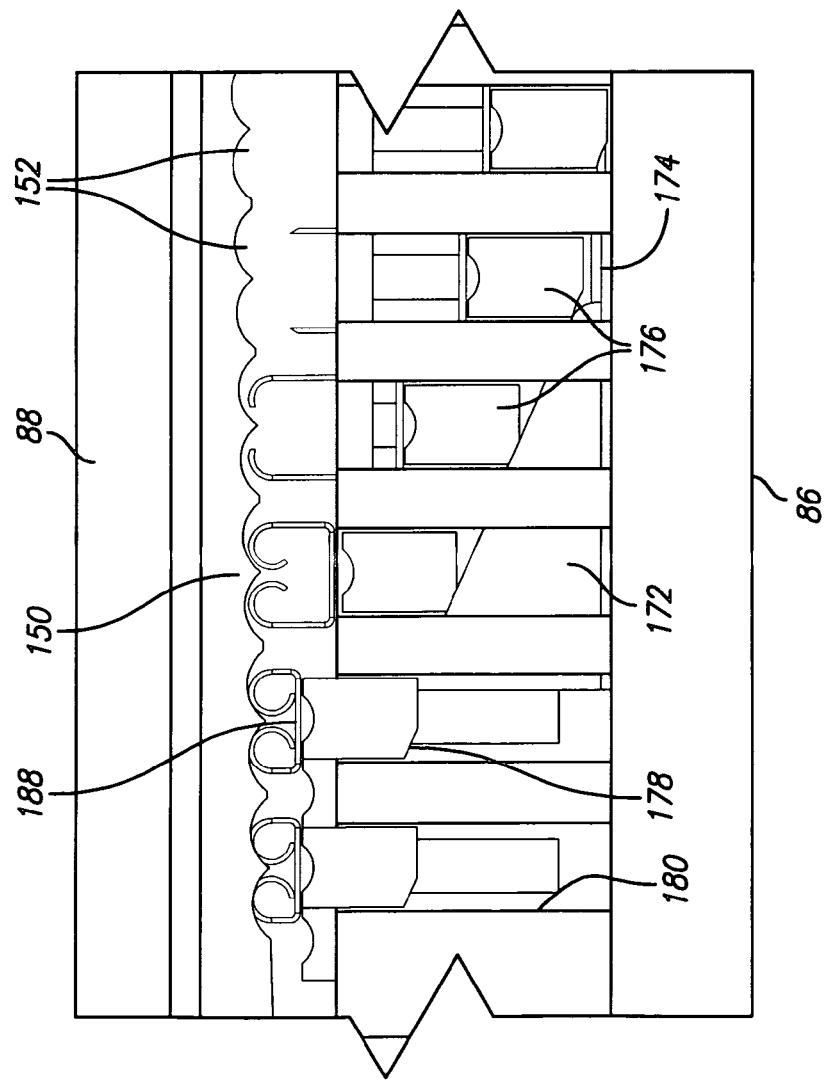
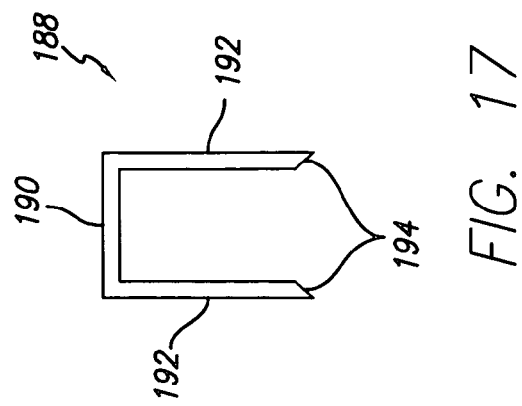
FIG. 16A
FIG. 17

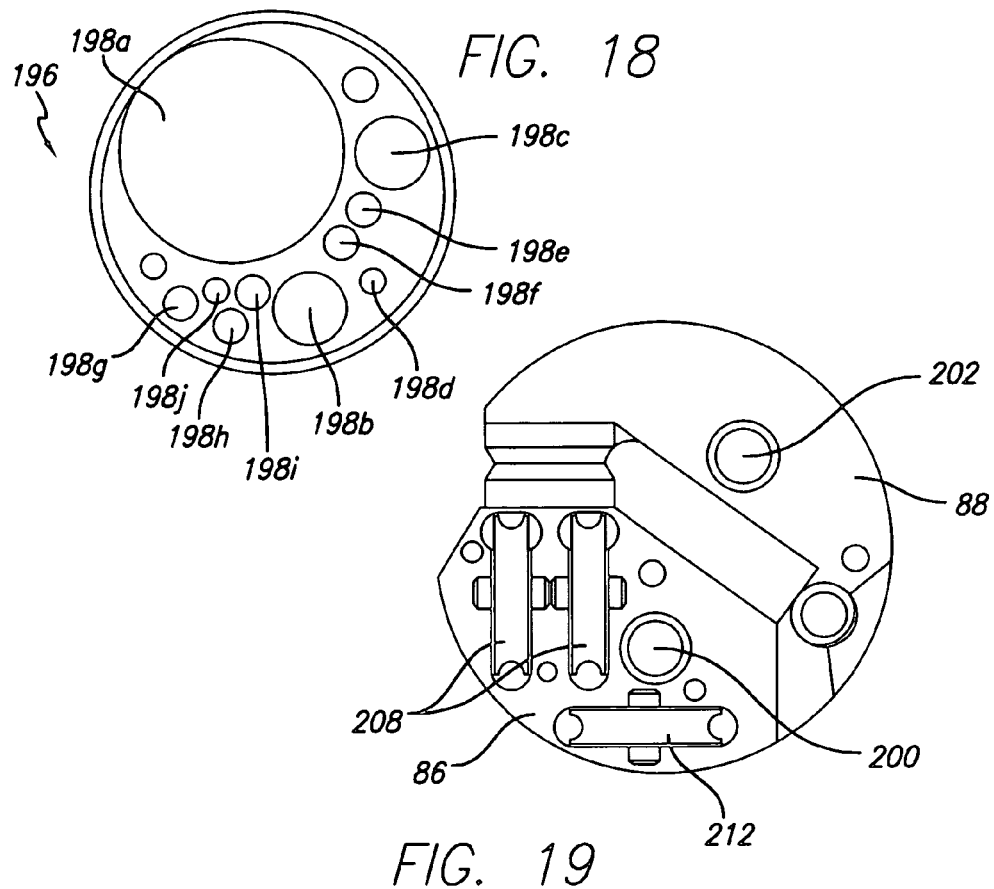
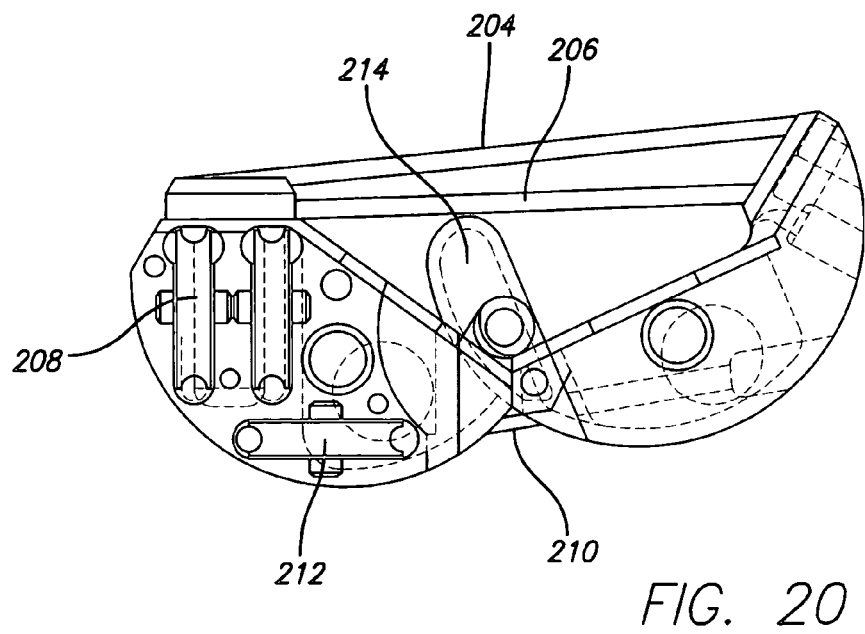

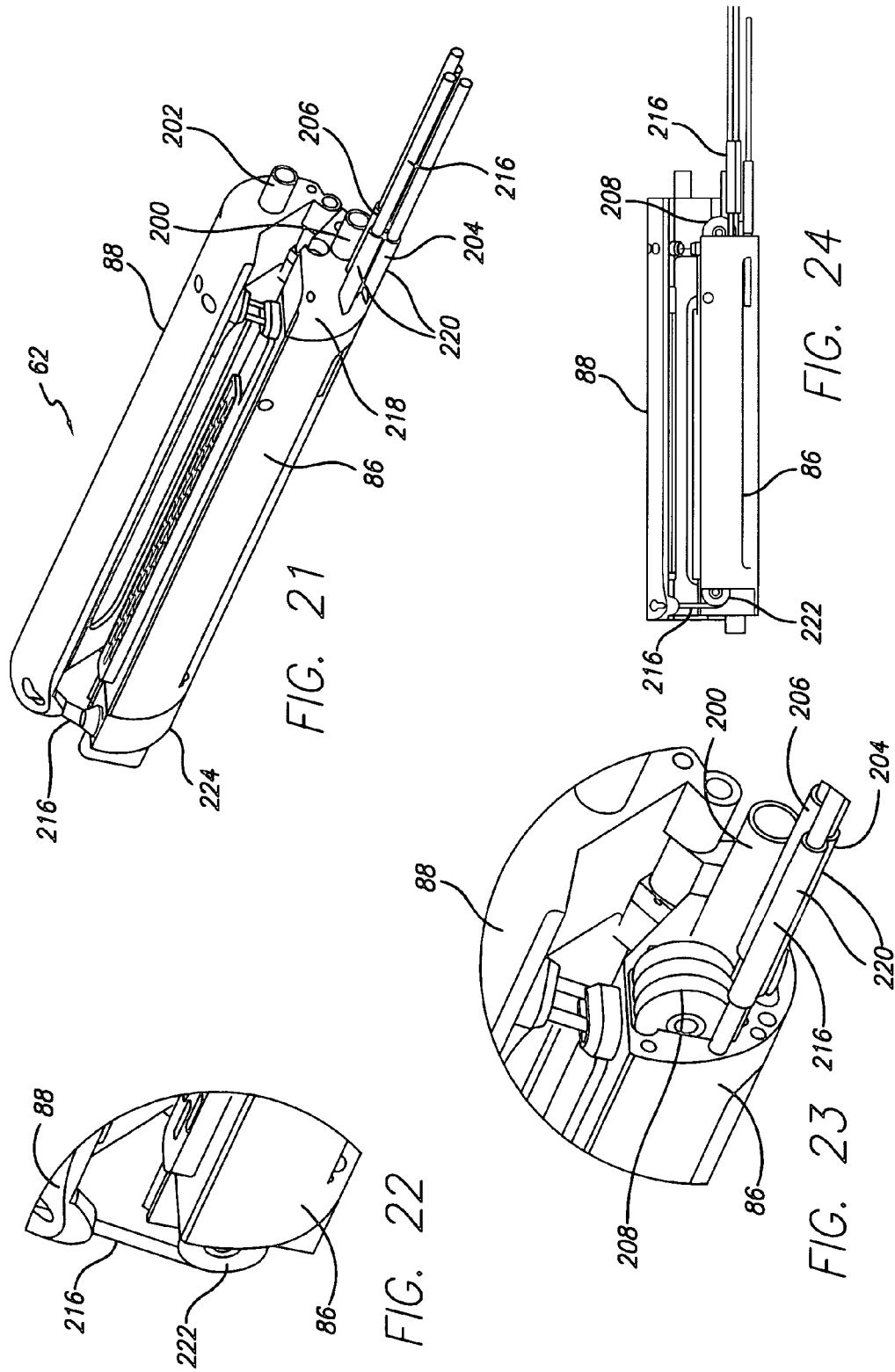

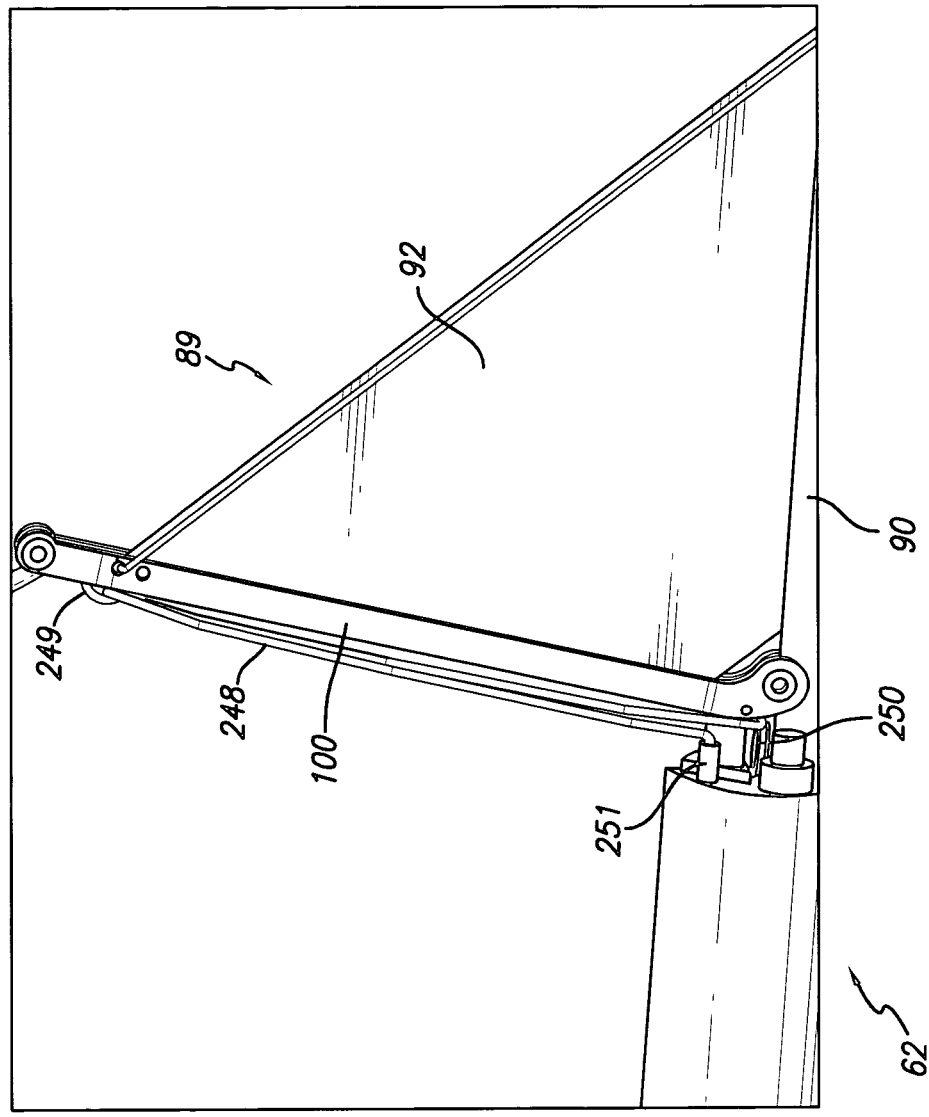

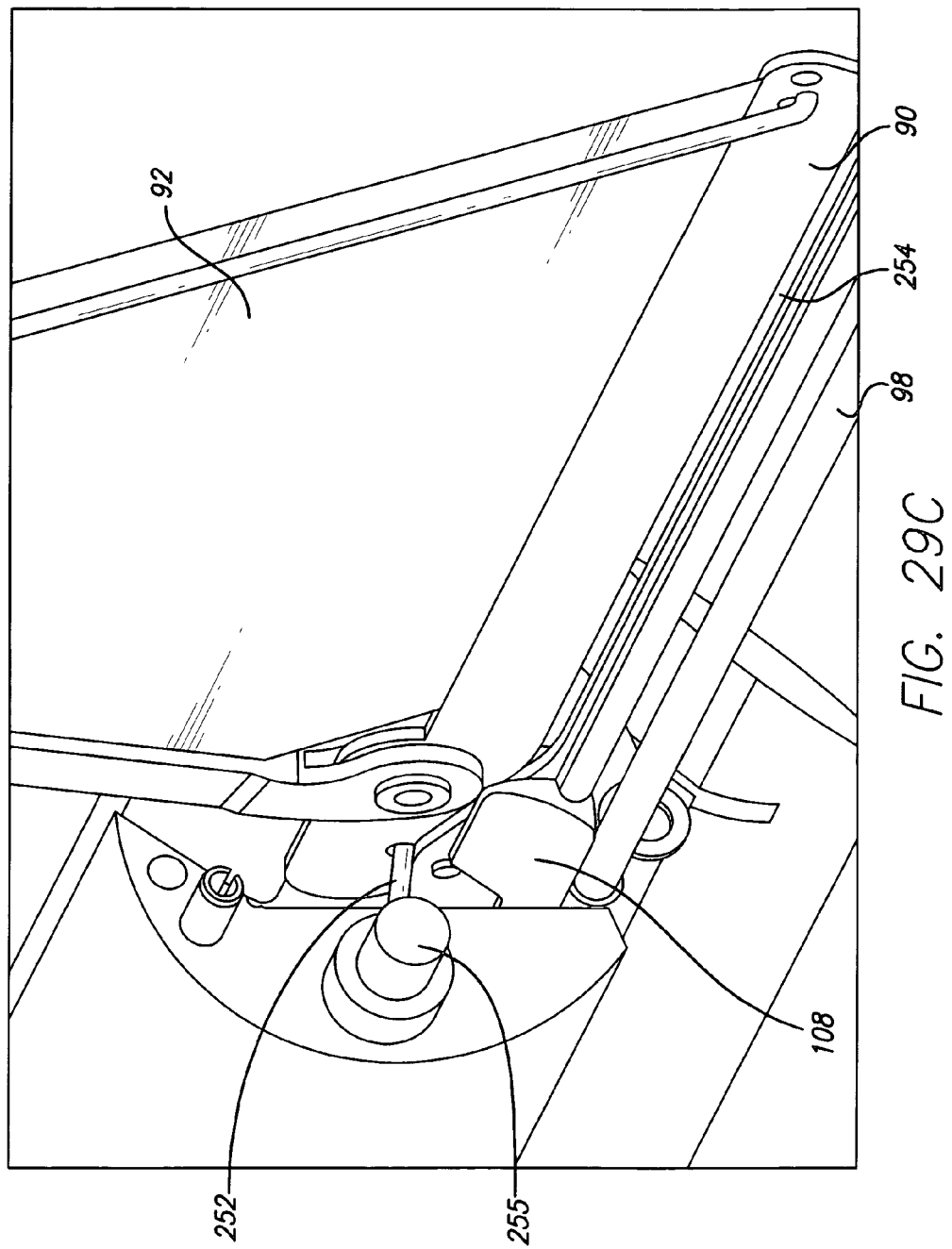

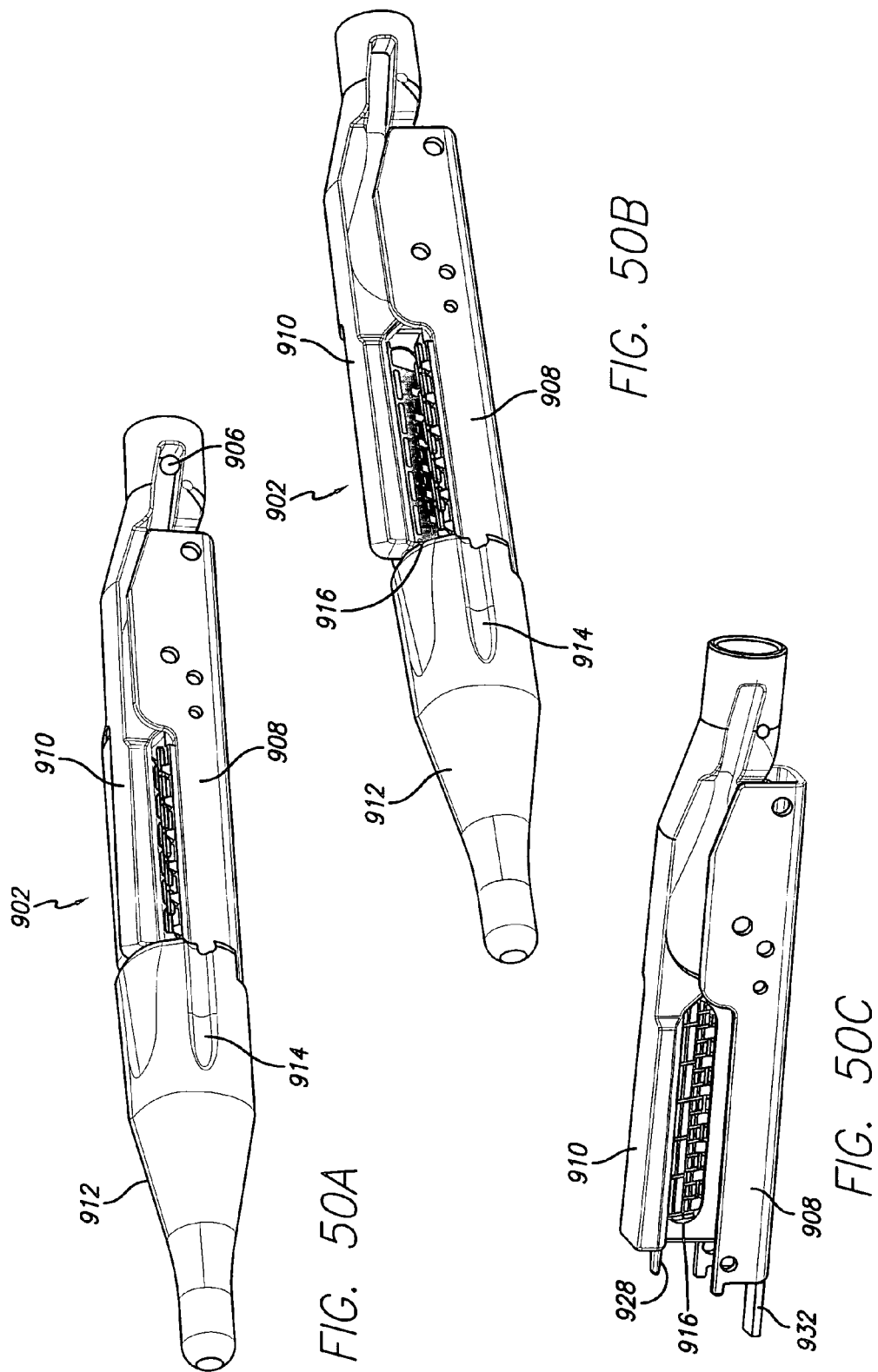

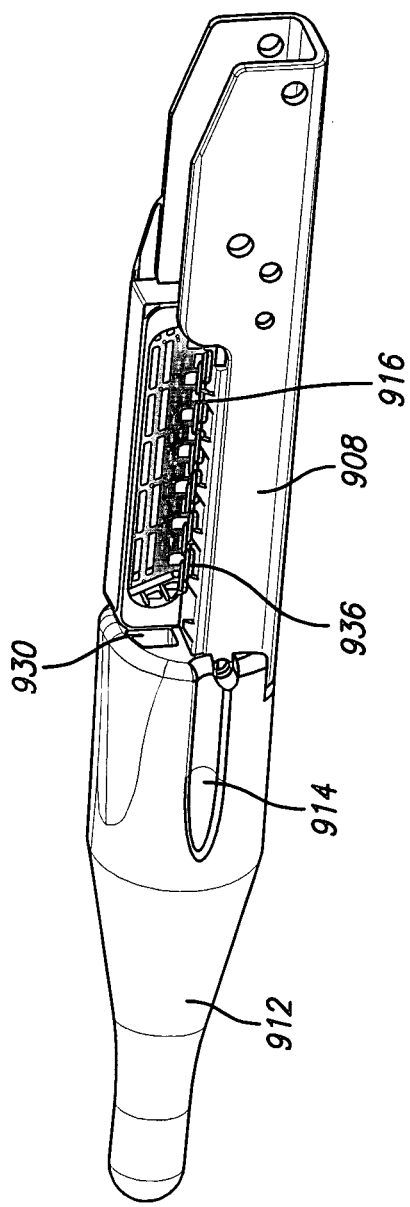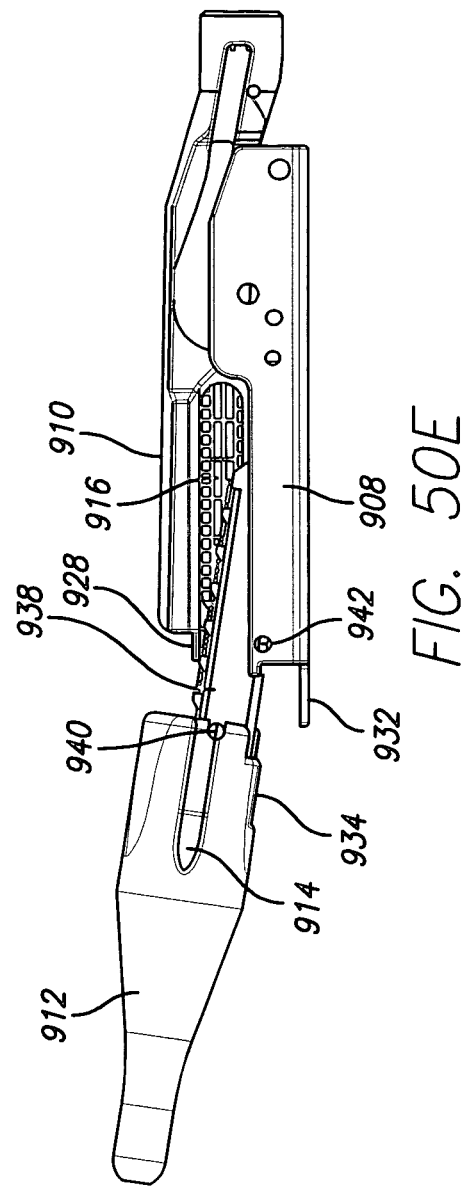

DEVICES AND METHODS FOR PLACEMENT OF PARTITIONS WITHIN A HOLLOW BODY ORGAN

CROSS-REFERENCE TO RELATED APPLICATION

This application is a continuation-in-part of application Ser. No. 11/324,135 filed on Dec. 29, 2005, now U.S. Pat. No. 8,252,009, which is a continuation-in-part of application Ser. No. 10/797,303, filed on Mar. 9, 2004, both of which are herein incorporated by reference.

BACKGROUND OF THE INVENTION

1. Field of the Invention

The present invention relates generally to medical devices and methods. More particularly, it relates to devices and methods for creating a partition within a hollow body organ, particularly a stomach, intestinal tract, or other region of the gastrointestinal tract, and affixing the tissue.

2. General Background and State of the Art

In cases of severe obesity, patients may currently undergo several types of surgery either to tie off or staple portions of the large or small intestine or stomach, and/or to bypass portions of the same to reduce the amount of food desired by the patient, and the amount absorbed by the gastrointestinal tract. The procedures currently available include laparoscopic banding, where a device is used to "tie off" or constrict a portion of the stomach, vertical banded gastroplasty (VBG), or a more invasive surgical procedure known as a Roux-En-Y gastric bypass to effect permanent surgical reduction of the stomach's volume and subsequent bypass of the intestine.

Typically, these stomach reduction procedures are performed surgically through an open incision and staples or sutures are applied externally to the stomach or hollow body organ. Such procedures can also be performed laparoscopically, through the use of smaller incisions, or ports, through trocars and other specialized devices. In the case of laparoscopic banding, an adjustable band is placed around the proximal section of the stomach reaching from the lesser curve of the stomach around to the greater curve, thereby creating a constriction or "waist" in a vertical manner between the esophagus and the pylorus. During a VBG, a small pouch (approximately 20 cc in volume) is constructed by forming a vertical partition from the gastroesophageal junction to midway down the lesser curvature of the stomach by externally applying staples, and optionally dividing or resecting a portion of the stomach, followed by creation of a stoma at the outlet of the partition to prevent dilation of the outlet channel and restrict intake. In a Roux-En-Y gastric bypass, the stomach is surgically divided into a smaller upper pouch connected to the esophageal inflow, and a lower portion, detached from the upper pouch but still connected to the intestinal tract for purposes of secreting digestive juices. A resected portion of the small intestine is then anastomosed using an end-to-side anastomosis to the upper pouch, thereby bypassing the majority of the intestine and reducing absorption of caloric intake and causing rapid "dumping" of highly caloric or "junk foods."

Although the outcome of these stomach reduction surgeries leads to patient weight loss because patients are physically forced to eat less due to the reduced size of their stomach, several limitations exist due to the invasiveness of the procedures, including time, use of general anesthesia, time and pain associated with the healing of the incisions, and other complications attendant to major surgery. In addition, these procedures are only available to a small segment of the obese population (morbid obesity, Body Mass Index>40) due to their complications, leaving patients who are considered obese or moderately obese with few, if any, interventional options.

In addition to surgical procedures, certain tools exist for securing tissue such as the stapling devices used in the above-described surgical procedures and others such as in the treatment of gastroesophageal reflux disease (GERD). These devices include the GIA® device (Gastrointestinal Anastomosis device manufactured by Ethicon Endosurgery, Inc. and a similar product by USSC), and certain clamping and stapling devices as described in U.S. Pat. Nos. 5,403,326; 5,571,116; 5,676,674; 5,897,562; 6,494,888; and 6,506,196 for methods and devices for fundoplication of the stomach to the esophagus for the treatment of gastroesophageal reflux disease (GERD). In addition, certain tools, such as those described in U.S. Pat. Nos. 5,788,715 and 5,947,983, detail an endoscopic suturing device that is inserted through an endoscope and placed at the site where the esophagus and the stomach meet. Vacuum is then applied to acquire the adjacent tissue, and a series of stitches are placed to create a pleat in the sphincter to reduce the backflow of acid from the stomach up through the esophagus. These devices can also be used transorally for the endoscopic treatment of esophageal varices (dilated blood vessels within the wall of the esophagus).

There is a need for improved devices and procedures. In addition, because of the invasiveness of most of the surgeries used to treat obesity and other gastric disorders such as GERD, and the limited success of others, there remains a need for improved devices and methods for more effective, less invasive hollow organ restriction procedures.

SUMMARY OF THE INVENTION

A device for tissue acquisition and fixation is described that may be utilized for creating a partition within a hollow body organ, such as the stomach, esophageal junction, and other portions of the gastrointestinal tract for performing a gastroplasty. Generally, the device may be advanced in a minimally invasive manner within a patient's body, e.g., transorally, endoscopically, percutaneously, etc., to create one or several divisions or plications within the hollow body organ. Such divisions or plications can form restrictive barriers within the organ, or can be placed to form a pouch, or gastric lumen, smaller than the remaining stomach volume to essentially act as the active stomach such as the pouch resulting from a surgical Roux-En-Y gastric bypass procedure. Examples of placing and/or creating divisions or plications may be seen in further detail in U.S. Pat. No. 6,558,400; U.S. patent application Ser. No. 10/188,547 filed Jul. 2, 2002; and U.S. patent application Ser. No. 10/417,790 filed Apr. 16, 2003, each of which is incorporated herein by reference in its entirety.

The device may be advanced within a body through a variety of methods, e.g., transorally, transanally, endoscopically, percutaneously, intraperitoneal surgically (natural orifice transvisceral endoscopic surgery), etc., to create one or several divisions or plications within a hollow body organ, e.g., to create a gastric lumen or partition to reduce the effective active area of the stomach (e.g., that which receives the initial food volume), performed from within the stomach cavity. The smaller gastric lumen created may be about 18 mm in diameter and about 70 cm in length with a volume of about 10 cc to about 100 cc, for example about 10 cc to about 25 cc, and may be achieved in a minimally invasive procedure completely from within the stomach cavity. Moreover, the device is configured such that once acquisition of the tissue is accomplished, manipulation of the acquired tissue is unnecessary as the device is able to automatically configure the acquired tissue into a desired configuration.

The device may generally include a first acquisition member and a second acquisition member in apposition to one another along a first longitudinal axis, wherein optionally, at least one of the acquisition members is adapted to adhere tissue thereto such that the tissue is positioned between the first and second acquisition members, and optionally wherein at least one of the acquisition members is movable relative to the first longitudinal axis between a delivery configuration and a deployment configuration. Moreover, the system may also include a septum, or a separator, removably positioned between the first and second acquisition members, wherein at least one of the acquisition members is movable relative to the septum between a delivery configuration and a deployment configuration.

A handle may be located at a proximal end of an elongate body or member and used to manipulate the device advanced within the hollow body organ as well as control the opening and closing/clamping of the acquisition members onto the tissue. The elongate body may include a series of links, or be formed from an extrusion fabricated with one or more various lumens to accommodate the various control mechanisms of the acquisition device. Similarly, the control mechanisms may be grouped together and sheathed in a thin skin sheath, such as a heat shrink or spirally wound adhesive backed tape. A working lumen may extend entirely through the elongate member and may be sized to provide access to the distal end for various surgical tools, such as an endoscope or other visualization device, and/or therapeutic devices such as snares, excisional tools, biopsy tools, etc. once the distal end of the assembly is positioned within the hollow body organ. The acquisition members may be joined to the elongate body via a passive or active hinge member, adaptable to position the assembly. The acquisition members may generally include a cartridge member placed longitudinally in apposition to an anvil member. The cartridge member may contain one or several fasteners, e.g., staples, clips, anchors, etc., which may be actuated via controls located proximally on the handle assembly. Moreover, the septum or tissue barrier may be removably positioned between the cartridge member and anvil member and used to minimize or eliminate cross acquisition of the tissue into the cartridge member and/or anvil member.

Methods of placing a partition from within a hollow body organ using the device disclosed herein generally includes positioning a first acquisition member and a second acquisition member adjacent to a region of tissue within the hollow body organ, wherein the first and second acquisition members are in apposition to one another along a first longitudinal axis, adhering tissue from the region to each of the first and second acquisition members, and securing the adhered tissue between the first and second acquisition members. Such a method may also involve pivoting at least one of the acquisition members about the longitudinal axis to an open or closed configuration, and still another method involves pivoting at least one of the members about the transverse axis. Another method may also include moving a septum or tissue barrier relative to the first and second acquisition member to control the length of the region of tissue acquired by the acquisition members, or removing the septum from between the first acquisition member and the second acquisition member.

Methods are also disclosed of placing a partition from within a first and a second organ. A tissue treatment device having first and second regions for releasably adhering tissue from the organs can be used to fasten the adhered tissue between the first and second regions of the tissue treatment device. In one embodiment, tissue from the gastroesophageal junction ("GEJ"), including the lower esophageal sphincter, along with tissue from the stomach is acquired with the tissue treatment device. The tissue treatment device forms one or more plications beginning at the GEJ and ending in the stomach cavity to form a pouch or an extension of the esophagus into the stomach cavity.

While the device is in a delivery configuration, the components of the distal working portion of the device (the cartridge member and anvil member) are disposed such that the cartridge and anvil are directly positioned into apposition about the septum. Once desirably positioned, one or both of the cartridge member and anvil member may be rotated about a pivot or translationally moved in parallel to one another. Then, portions of the stomach wall may be acquired by, or drawn within their respective openings. The configuration of the cartridge member and anvil member and the positioning of the device within the stomach are such that this tissue acquisition procedure also enables the devices to be self-adjusting with respect to the acquired tissue. Alternatively, the cartridge and anvil members may close to within a fixed distance, i.e. a fixed distance clamp gap. Moreover, the device is configured such that portions of the stomach wall are automatically positioned for fixation upon being acquired and the tissue becomes automatically adjusted or tensioned around the perimeter of the distal working portion of the device in the stomach and within the distal working portion inner volume, to achieve the desired resulting geometry (e.g., small gastric pouch or restrictive partition or baffle). Because of the manner in which the tissue is acquired, the tissue intimately surrounds the cartridge member and anvil member to define or calibrate the subsequent volume of the resulting gastric lumen. Thus, the gastric volume may be somewhat controlled by adjusting the volume of the cartridge member and anvil member, or the use of accessory devices such as a scope or balloon. As a result, once the desired volume is known and incorporated in the device, the user can achieve a controlled acquisition and without intraprocedural adjustments or positioning requirements.

The septum may act effectively as a barrier between the openings to facilitate the acquisition of the tissue to their respective openings while minimizing or eliminating cross acquisition of the tissue into the cartridge member and/or anvil member. In other alternatives, the septum may be omitted from the device and acquisition of the tissue may be accomplished by sequentially activating vacuum forces within the openings. Once the tissue has been acquired, the septum may be removed from between the cartridge member and anvil member by translating the septum distally or proximally of the cartridge member and anvil member or left within the stomach for later removal. Alternatively, the septum may rotate, collapse, be ejected up and out from between the jaws. In one alternative, the septum includes a sail that can be extended between the cartridge member and anvil member after being delivered to the stomach, and then collapsible between the cartridge member and anvil member for removal from the stomach.

The cartridge member of the tissue treatment device may be re-loadable with a removable staple cartridge after forming a plication within the cavity. This allows the same tissue treatment device to form multiple plications within the cavity. A method of treating a stomach cavity may include forming a first plication within the stomach cavity using staples from a first removable staple cartridge, which is easily removed from the cartridge member. A second removable staple cartridge is then inserted into the cartridge member, and a second plication is formed within the stomach cavity using staples from the second removable staple cartridge.

Another method of forming a plication within the stomach cavity may include clamping the cartridge member and the anvil member together and then reevaluating the folds of tissue acquired before firing staples into acquired tissue. This method helps to ensure that the desired tissue is acquired by the tissue treatment device, and that there are no folds or pleats present in the acquired tissue. After inserting the tissue treatment device transorally to the stomach cavity, stomach tissue is acquired at a target region for treatment with the tissue treatment device. The cartridge member and anvil member of the tissue treatment device are then clamped together grasping the acquired target tissue, and the stomach cavity can be insufflated to inspect the acquired target tissue with an endoscope. If the inspection reveals that the tissue acquired is not the targeted tissue or that there are folds or pleats within the acquired tissue, the acquired tissue can be released from the tissue treatment device and re-acquired. If the inspection reveals the acquired tissue would form a desired sleeve, then the stomach cavity can be desufflated once again, and the cartridge member and the anvil member may be unclamped into an open configuration, to fully acquire the tissue. The tissue treatment device may include a barrier such as a septum, in which case the barrier would be moveable between the cartridge and anvil member to control the length of tissue secured, or removed from between the cartridge member and the anvil member to fasten the full length of the cartridge and anvil working surface. After which, the cartridge member and anvil member are clamped together and the stomach cavity is again insufflated to inspect the acquired tissue. If the inspection reveals a desired formation between the folds of acquired tissue, the cartridge member and anvil member are fully clamped together and the acquired tissue is plicated to form a gastric sleeve within the stomach cavity and the GEJ.

Another method involves lightly clamping the cartridge member and the anvil member together and then reevaluating the folds of tissue acquired before firing staples into acquired tissue. After inserting the tissue treatment device transorally to the stomach cavity, stomach tissue is acquired at a target region for treatment with the tissue treatment device. The cartridge member and anvil member of the tissue treatment device are then lightly clamped together grasping the acquired target tissue, and the stomach cavity can be insufflated to inspect the acquired target tissue with an endoscope. If the inspection reveals that the tissue acquired is not the targeted tissue or that there are folds or pleats within the acquired tissue, the acquired tissue can be released from the tissue treatment device and re-acquired. If the inspection reveals the acquired tissue would form a desired sleeve, then the stomach cavity can be desufflated once again, and the cartridge member and the anvil member may be fully clamped and the acquired tissue is plicated to form a gastric sleeve at least partially within the stomach cavity. The tissue treatment device may include a barrier such as a septum, in which case the barrier would be moveable between the cartridge and anvil member to control the length of tissue secured, or removed from between the cartridge member and the anvil member to fasten the full length of the cartridge and anvil working surface.

A system for reducing the volume of the stomach cavity may include the tissue treatment device for forming a plication at least partially within the stomach cavity and a restrictor device to further restrict the stomach cavity. When forming a sleeve along the lesser curve of the stomach with the tissue treatment device, the restrictor device may be used to acquire tissue between an anvil member and a cartridge member to form a single fold plication within the sleeve. The restrictor device may have a vacuum pod located between the anvil and cartridge member to acquire the desired tissue. A distal outlet of the sleeve can be reduced by placing a plication with the restrictor device near the distal outlet. Further, the tissue treatment device may form multiple continuous plications within the stomach cavity. In the event that unwanted stomas are form between the multiple plications, the restrictor device can be used to close those unwanted stomas.

BRIEF DESCRIPTION OF THE DRAWINGS

FIG. 5 shows a tissue treatment device of the gastroplasty device with jaws opened and a wire retractor and sail extended.

FIG. 13 shows a backside perspective view of the tissue treatment device with the distal tip removed for clarity.

FIG. 14 shows a perspective view of a removable staple cartridge.

FIG. 15 shows a perspective view of the removable staple cartridge positioned within a cartridge member of the tissue treatment device.

FIG. 16 shows a partial cross-sectional side elevational view of the removable staple cartridge positioned within the cartridge member of the tissue treatment device.

FIG. 16A shows partial cross-sectional side elevational view of staples being fired from the staple cartridge and crimped against an anvil.

FIG. 17 depicts a round wire staple.

FIG. 18 shows a planar view of an end ring that is connected to a distal end of the flexible elongated member.

FIG. 19 shows a partial cross-sectional view of the tissue treatment device in a closed position.

FIG. 20 shows a partial cross-sectional view of the tissue treatment device in an open position.

FIGS. 21 through 24 show another embodiment of a tissue treatment device having a distal clamping wire passed around a distal vertical pulley.

FIGS. 28A through 28C depict an embodiment of a Kevlar rope connected to the distal end of the tissue treatment device to assist in closing the jaws of the tissue treatment device.

FIGS. 29A through 29C depict an embodiment of a stainless steel cable connected to the distal end of the tissue treatment device to assist in closing the jaws of the tissue treatment device.

FIG. 50A shows a stapler assembly of the stapler restrictor in a closed configuration.

FIG. 50B shows the stapler assembly of the stapler restrictor in an open configuration.

FIG. 50C shows the stapler assembly of the stapler restrictor with a rubber tip and removable staple cartridge removed.

FIG. 50D shows the stapler assembly of the stapler restrictor with an anvil member removed.

FIG. 50E shows the removable staple cartridge and rubber tip being loaded into a cartridge member of the stapler assembly.

DETAILED DESCRIPTION OF THE EMBODIMENTS

Figure 1:
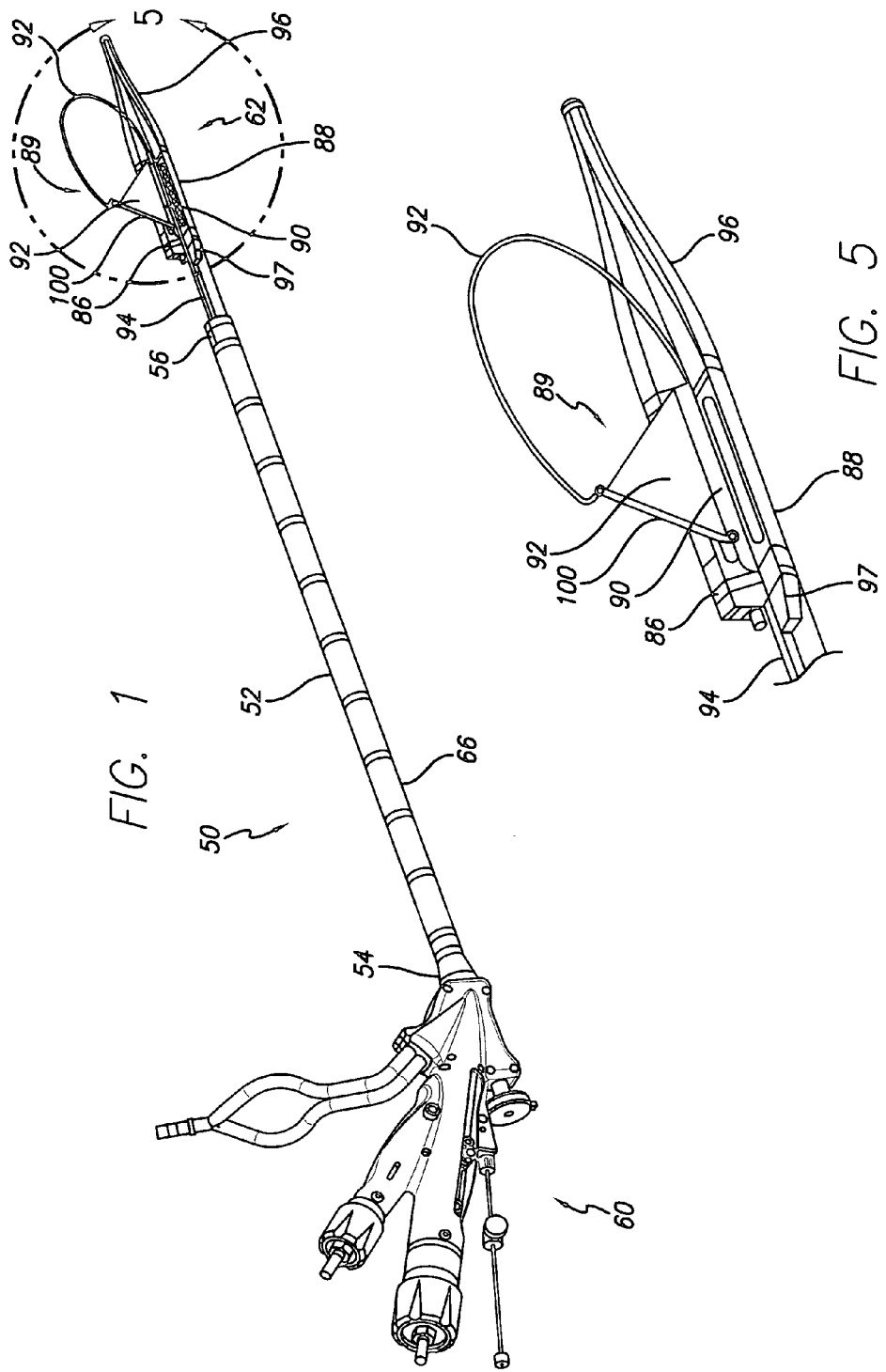
FIG. 1 shows a perspective view of one embodiment of a gastroplasty device.

A gastroplasty device for tissue acquisition and fixation, and methods of use are described. In general, the gastroplasty device described herein may be utilized for creating a partition within a hollow body organ or two hollow body organs, such as the stomach, esophageal junction, and/or other portions of the gastrointestinal tract. The gastroplasty device may be advanced within a body through a variety of methods, e.g., transorally, transanally, endoscopically, percutaneously, etc., to create one or several divisions or plications within the hollow body organ, e.g., to create a gastric lumen within the stomach. Further, the gastroplasty device may be assisted through the use of laparoscopic guidance, in particular, visualization of the external surface of the hollow body organ to assist in placement of the device, or within the organ cavity to monitor the procedure. Similarly, the device of the present invention may be used in conjunction with other laparoscopic procedures, or may further be modified by an additional step or procedure to enhance the geometry of the partition. For example, upon placement of a partition of the present invention, it may be desirable to perform a secondary step either transorally, or laparoscopically, to achieve the desired gastroplasty geometry, such as the placement of a single fold or plication within the gastric lumen or pouch as described in U.S. patent application Ser. No. 10/188,547, which was filed Jul. 2, 2002 and is incorporated by reference herein in its entirety, to further restrict the movement of food through the pouch, or the laparoscopic placement of a band, clip, ring or other hollow reinforcement member at the outlet of the gastric lumen such as is done in a VBG, or lap-band procedure to reinforce or narrow the outlet of the lumen.

The gastroplasty device described here, allows for the creation of a smaller gastric lumen to be achieved in a minimally invasive surgical procedure completely from within the stomach cavity and gastroesophageal junction. Moreover, the devices described herein are configured such that once acquisition of the tissue is accomplished, any manipulation of the acquired tissue may be unnecessary as the device is able to automatically configure the acquired tissue into a desired configuration whereby the geometry of the devices approximates the resulting tissue geometry at the time of acquisition. In operation, the perimeter of the device, and any openings therein, form the template or mold cavity around and into which tissue flows, thereby creating a tissue structure that approximates the geometry of the mold. That is, as the device is configured such that portions of the stomach wall are automatically positioned for fixation upon being acquired, and the tissue becomes automatically adjusted or tensioned around the perimeter of the distal working portion of the device in the stomach and within the distal working portion inner volume, to achieve the desired resulting geometry (e.g., small gastric pouch, restrictive partition or baffle, or extension of esophagus). Because of the manner in which the tissue is acquired, the tissue intimately surrounds the cartridge member and anvil member to define or calibrate the subsequent volume of the resulting gastric lumen. Thus, the gastric volume may be predetermined by adjusting the volume of the cartridge member and anvil member. Subsequent manipulation of the tissue may be performed, if desired, to effect certain configurations or further restrict the pouch; however, this manipulation may be omitted entirely.

One embodiment of a gastroplasty assembly 50 is shown in FIG. 1. Assembly 50 includes an elongate tubular member 52 having a proximal end 54 and a distal end 56 with a lumen 58 defined within the elongate member. As shown in FIG. 1, a handle assembly 60 is connected at the proximal end of the elongate member, and a tissue treatment device or working member 62 is attached at the distal end of the elongate member. The tissue treatment device is used to form either single or dual fold plications within a stomach cavity and the gastroesophageal junction.

The elongate tubular member 52 may have a circular or elliptical cross-sectional area. Alternatively, the cross-sectional area may take on any number of different cross-sectional configurations, e.g., hexagonal, octagonal, etc., provided that it presents an atraumatic surface to the tissue surfaces within the body. In the embodiment shown, the elongate member is a flexible shaft including a series of links 64 that increase the flexibility of the elongate member, and hence increase the ease in which the device is handled and operated. The lumen 58 may extend entirely through the tubular member and may be sized to provide access to the distal end 56 for various surgical tools or therapies once the distal end of assembly 50 is positioned within a hollow body organ, and in particular may be useful to place an endoscope or other visualization tool for real time visualization during the procedure. Alternatively, a fiberscope or other type of visualization tool may be integrated within the elongate member. Examples of useful scopes may be the Olympus GIF P140, the Fujinon EG 25PE, and the like. An optional separate thin walled oversheath or liner 66, may also be placed over the acquisition device, including the links of the elongate member, to assist in placement, or may be placed over a guide wire or obturator down the esophagus prior to placement of the gastroplasty device and removed with the gastroplasty device once the procedure is complete. The oversheath or liner may be made of a thin wall polymer such as polyolefin, polytetrafluoroethylene (PTFE), expanded PTFE (ePTFE), silicone and the like, having a wall thickness preferably between about 0.001" and about 0.025". This liner can serve to guide the gastroplasty device, as well as help to limit trauma to the esophagus and other delicate structures.

Figure 2:
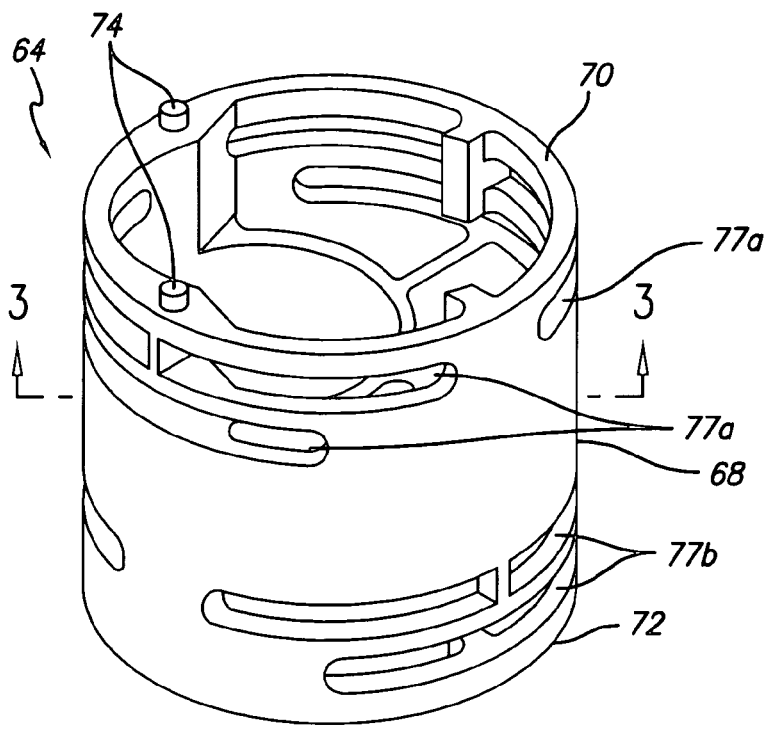
FIG. 2 shows a perspective view of a link used to form an elongated tubular member for the gastroplasy device.

FIG. 2 shows a perspective view of a single link member 64 having a circular body 68 with a first end 70 and a second end 72. The circular body defines at least a portion of the lumen 58. Alignment points are disposed on the circular body in order to properly join multiple links together to form the lumen. In one embodiment, the first end of the link includes at least two radial pins 74 and the second end includes at least two radial holes 76 (shown in FIG. 3) that complement the radial pins from an adjacent link when multiple links are joined together. The radial pins (and radial holes) are shown to be positioned less than 90° from each other around the end of the link, however, the radial pins (and radial holes) can be positioned from near 0° to 180° from each other around the end of the link. The pins and complementary holes can be any shape, such as circular, oval or any polygonal shape. As shown in FIG. 2, there are a plurality of slots 77 cut or formed within the circular body of the link that allow the elongate tubular member 52 to flex. In this embodiment, one set of slots is positioned adjacent the first end and a second set of slots is positioned adjacent the second end, wherein the second set of slots are offset from the position of the first set of slots.

Figure 3:
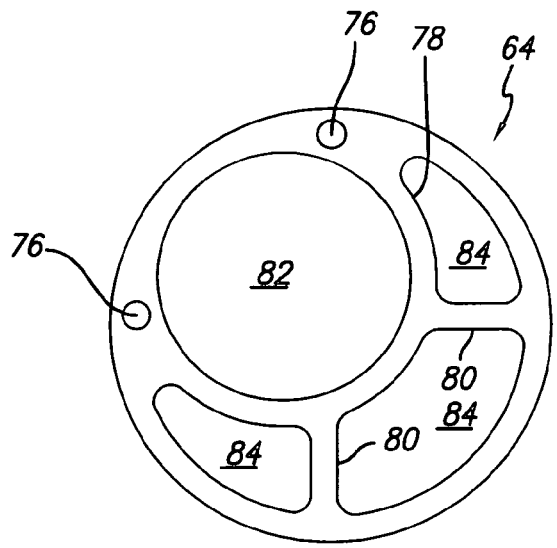
FIG. 3 shows a cross-sectional view taken along line 3-3 of FIG. 2.

Referring now to FIG. 3, which is a cross-sectional view taken along line 3-3 of FIG. 2, one embodiment of the internal cavity of the link 64 is shown to include an inner arch 78 and dividers 80 that divide the lumen 58 into an endoscope lumen 82 and a three working lumens 84. In one embodiment, only an inner arch is present with no dividers so that there is only an endoscope lumen and one working lumen. It has also been contemplated that the no divisions exist in the lumen of the link. The endoscope lumen is sized such that an endoscope may pass there through. In an exemplary embodiment, the inner arch and dividers are formed within every link, although the inner arch and dividers will only extend along a portion of the link's length, for example, only between the first set of slots 77a and the second set of slots 77b. Alternatively, the inner arch and dividers are only formed within every other sliding link in the chain that forms that elongate member 52 to help increase its flexibility. The working lumens 84 provide passages for various cables for controlling the opening and closing of tissue treatment device 62 as well as additional cables for actuating deployment of fasteners/staples from within the staple cartridge of the tissue treatment device. Moreover, the working lumens may be used for the passage of vacuum tubes connected to vacuum pods formed within the tissue treatment device, and for the passage of retractor wires and septum wire (used to remove septum from the tissue treatment device). These passages provided by the working lumens prevent gross movements of the cables and coil pipes, and also keep the endoscope free from entanglement. The working lumens within the elongated member allow small movements of the cables and coil pipes which may be important during bending of the shaft.

Figure 4:
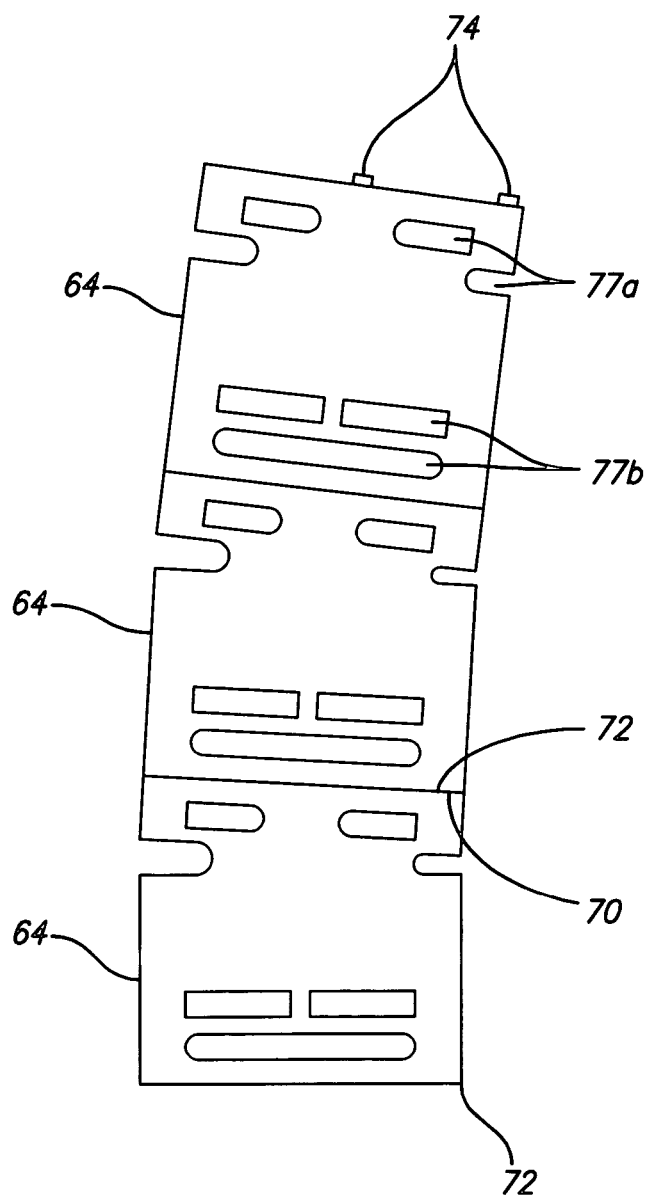
FIG. 4 shows multiple links used to form the elongated tubular member joined together.

As shown in FIG. 4, three links 64 are shown joined together and bending or flexing at the slots 77 formed in the circular body 68 of the links. The links are attached or coupled together by inserting the radial pins 74 of one link into the radial holes 76 of an adjoining link and the adjoined links are glued together across the flat registration planes at the end of the link members. It has been contemplated that the links could be bonded together mechanically using a dovetail joint to create attachment between each link. The design of the links allow them to transmit torque along the length of the elongate member 52. Several links are attached to one another depending on the desired length of the elongate member. Typically, the length of the elongate member is determined by the anatomic length of a patient such that the distal end of the device reaches into the patient's stomach while the proximal end extends out of the patient's mouth for a length sufficient to enable the user to manipulate the controls of the device, approximately 30 cm-110 cm long, for example approximately 50 cm-70 cm. Also, the diameter of the elongate member is less than about 60 Fr, and more preferable equal to or less than about 54 Fr. In one embodiment, the liner 66 is a polyethylene tape wrapped around the outer surface of the joined links to limit trauma to the esophagus and other delicate structures, while still allowing the elongate member to flex while limiting extensibility of the shaft. Other materials that may be used as coverings may include silicone, urethanes, or other polymers. In a further embodiment, such coatings may be sprayed on or applied as a coating or sheath, rather than wound as tape. However, it has also been contemplated that the elongated member may be formed using braided, molded, or slotted material, such as any metal or polymer. The elongated member may even be formed with a polymer that does not includes links.

Referring to FIGS. 1 and 5, the tissue treatment device 62 attached to the distal end 56 of the elongate member 52 includes a working portion with a cartridge member or jaw 86 placed longitudinally in apposition to anvil member or jaw 88. The length of the jaws is preferably about 70 mm, but may range between about 40 mm and about 100 mm. Also, the diameter of the jaws when in the closed configuration is about 16 mm, but may be any diameter less than about 22 mm. When the tissue treatment device is in use, the tissue of the stomach wall (including, in some instances, the muscular tissue layers) are adjusted or tensioned around the perimeter of the distal working portion, and within the distal working portion inner volume, to achieve a desired resulting geometry (e.g., small gastric pouch or restrictive partition or baffle). Thus, the gastric pouch volume may be predetermined by adjusting the volume of the tissue treatment device, inner or outer profile. Typically, the volume of the pouch formed within the stomach is about 10 cc-22 cc if one plication is used, or about 20 cc-50 cc if two plications are used to form a longer pouch within the stomach. Cartridge member 86 may contain one or several fasteners, e.g., staples, clips, anchors, etc., which may be actuated via controls located proximally on handle assembly 60. A septum 89 may be removably positioned between the cartridge member and the anvil member while connecting member or pin 94 may connect the treatment device to the elongate tubular member. The septum acts as a tissue barrier between the jaws of the device in one embodiment includes a base 90 attached to a sail. An atraumatic distal tip 96 can also be attached to the distal end of the tissue treatment device to limit trauma to the esophagus and stomach cavity. In this embodiment, the atraumatic distal tip is a split flexible tip that opens and closes with the jaws of the tissue treatment device to protect the stomach tissue from the septum when it is translated distally out from the jaws. Further, it is preferred that the distal tip is about 4 inches in length, however, a length of between 2 to 5 inches is desirable to prevent the tip and the tissue treatment device from becoming caught in the folds of tissue found in the stomach. An atraumatic proximal tail 97 is also shown disposed on the proximal end of the anvil member. The cartridge member may also include an atraumatic proximal tail as well. The proximal tail is formed of a soft plastic and helps prevent trauma to the patient when the device is moved proximally within a newly formed pouch or completely removed from the stomach cavity. There is also a retractor wire 98 attached to a mast or sail arm 100 that extends the sail 92 above the base 90. It has also been contemplated that the sail can be raised by a spring loaded sail arm that extends when the jaws of the device are opened. Also, the sail may be raised by a pull-wire that is attached to the sail arm at one end and to handle assembly at the other. To raise the sail, the user would pull the pull-wire proximal to move the hinged sail arm and extend the sail. Another embodiment of the tissue treatment device including a retractor wire and sail is described in more detail with reference to FIGS. 76-80 of U.S. patent application Ser. No. 11/282,320, which was filed on Nov. 17, 2005, and is hereby incorporated by reference in its entirety.

Figure 6:
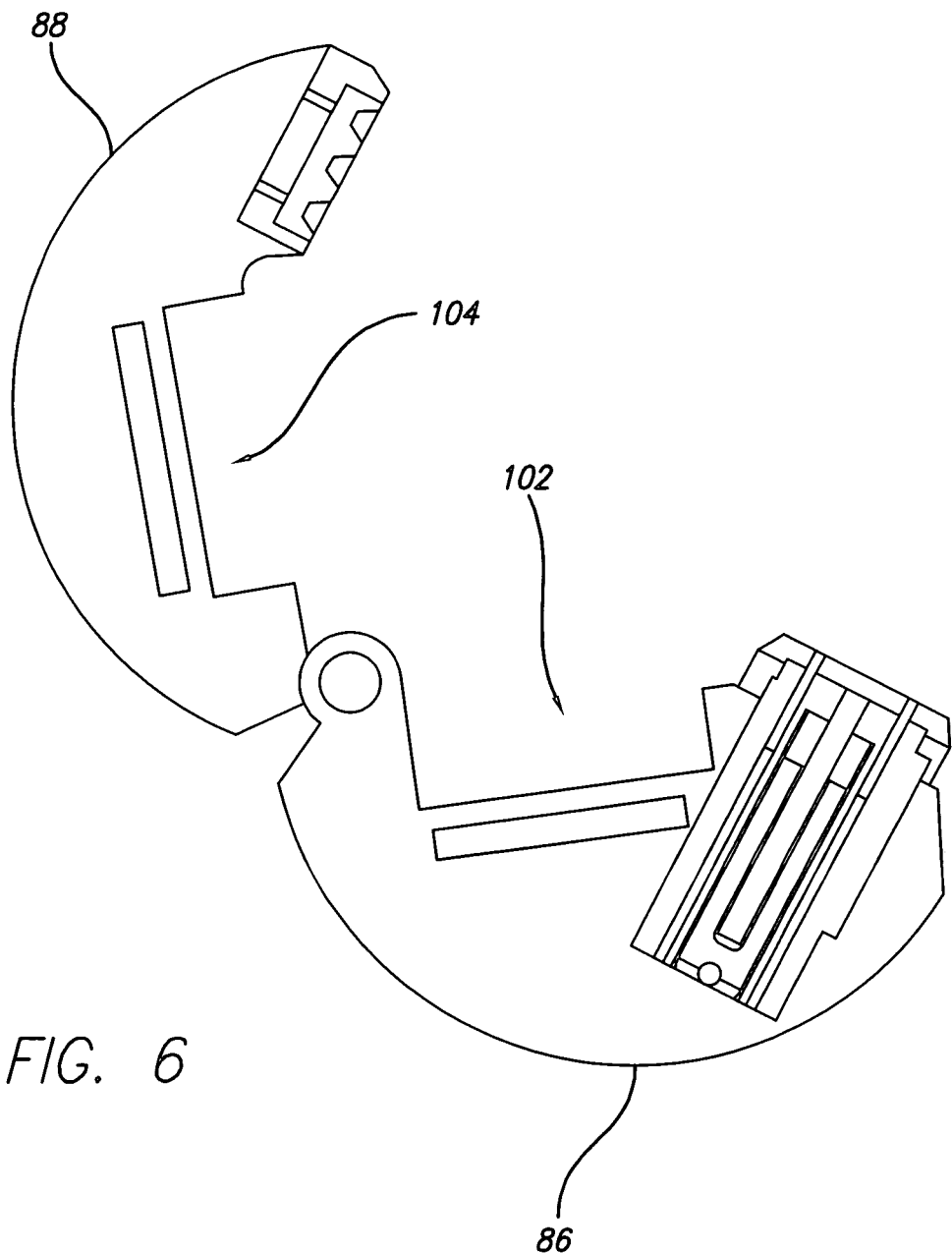
FIG. 6 shows a partial cross-sectional view of the tissue treatment device.
Figure 7:
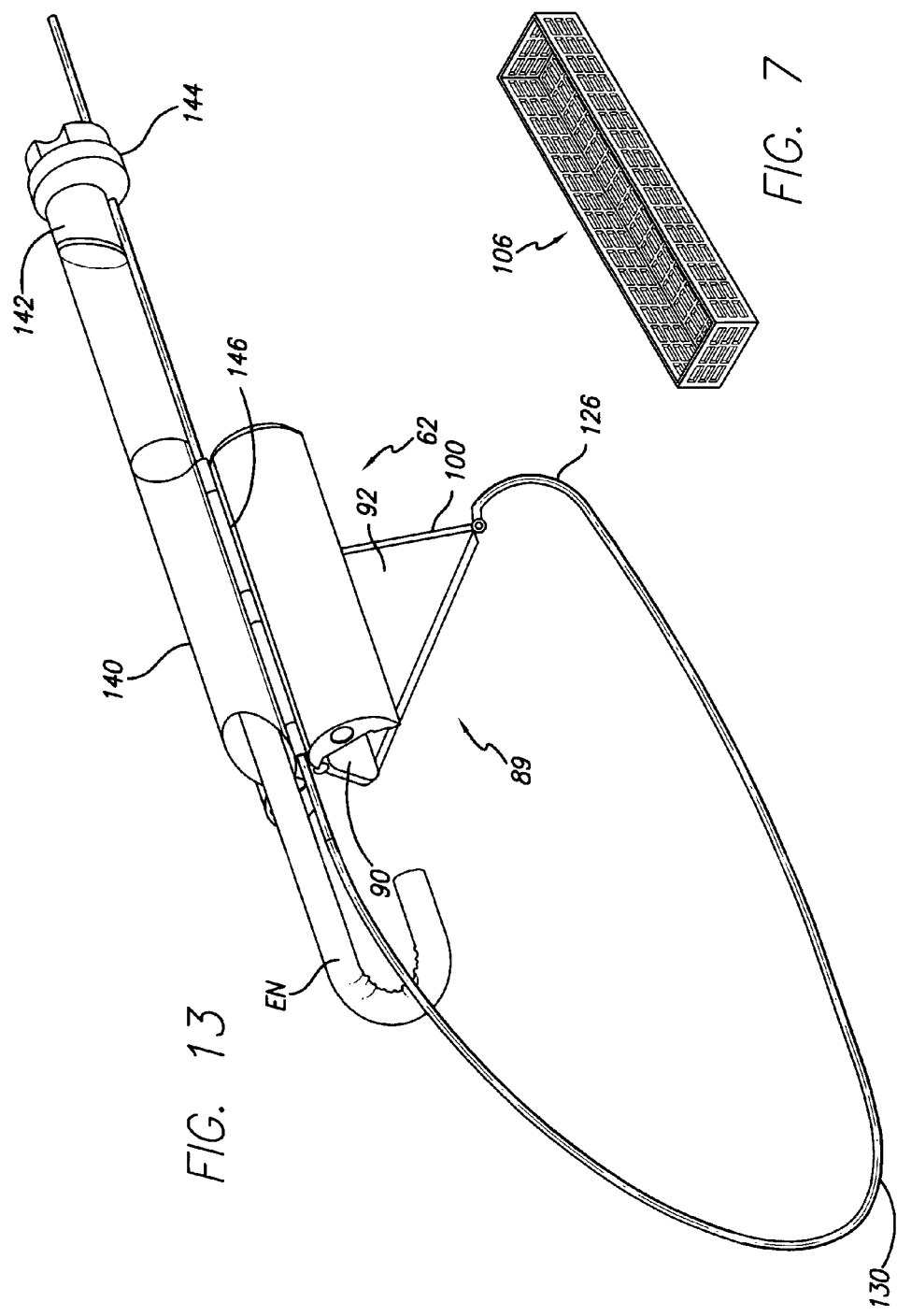
FIG. 7 shows a variation of a basket that may be disposed within a vacuum pod of the tissue treatment device.

As shown in FIG. 6, which is a cross-sectional view of the cartridge and anvil members 86 and 88 alone for clarity, both members of the tissue treatment device 62 define openings or vacuum pods 102 and 104, respectively, along a portion of the length or the entire length of each of the members. One or both of these openings may be connected via tubing through elongate member 52 to vacuum ports located at the handle assembly 60. Alternatively, a central vacuum lumen may supply both ports, or may bifurcate at the proximal or distal end of elongate member. Targeted tissue can be sucked into these openings when a vacuum is applied. To prevent tissue from becoming caught or snagged onto the edges of the openings, baskets 106 with holes can be placed within each opening. Further, the baskets maintain a plenum within the vacuum openings allowing the vacuum to flow to all areas of the vacuum pod. One embodiment of the basket is shown in FIG. 7 that has rows of three openings per side, and with each individual opening measuring about 0.070 inch in width and about 0.060 inch in height. However, baskets with any number of rows of openings per side and with a variety of sizes have also been contemplated. Also, to prevent "snagging" of tissue, the outside of the tissue treatment device is designed to be as smooth as possible. This allows tissue to "flow" around the device and into the openings. It may also be desired to effect the outside shape so that the acquisition slows the flow of certain tissue to acquire more of a particular target tissue, i.e. slow the flow of mucosa layer into the pod to allow more of the serosa layer to be gathered.

Detailed views of one embodiment of the tissue treatment device 62 with the septum 89 are shown in FIGS. 5 and 8 through 12. The cartridge member 86 and anvil member 88 may be both or singularly articulatable relative to one another or relative to elongate member 52. A hinge longitudinally positioned between cartridge member and anvil member may be configured to enable the device to be pivoted into an open configuration for the acquisition of tissue and a closed or deployment configuration for delivery or advancement of the device into the hollow body organ. In one embodiment, the retractor wire 98 extends from the proximal end 54 of the elongate member to the tissue treatment device and through the hinge that pivots the members 86 and 88. In an alternative embodiment, the wire retractor extends through a strap that is attached to the backside of the tissue treatment device.

Figure 8:
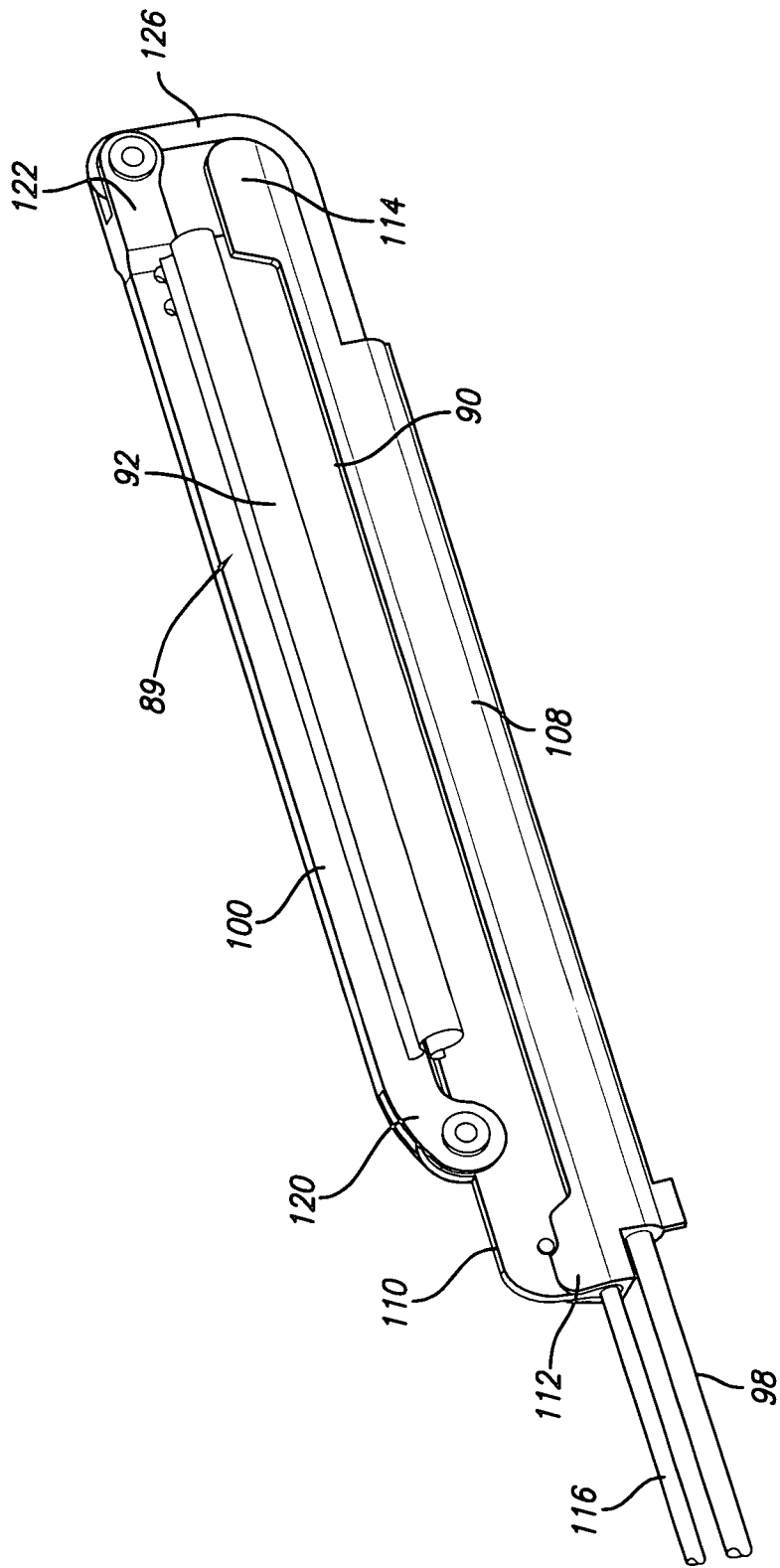
FIG. 8 shows a variation of a septum including sail that may be positioned between the jaws of the tissue treatment device in a retracted or delivery configuration.
Figure 9:
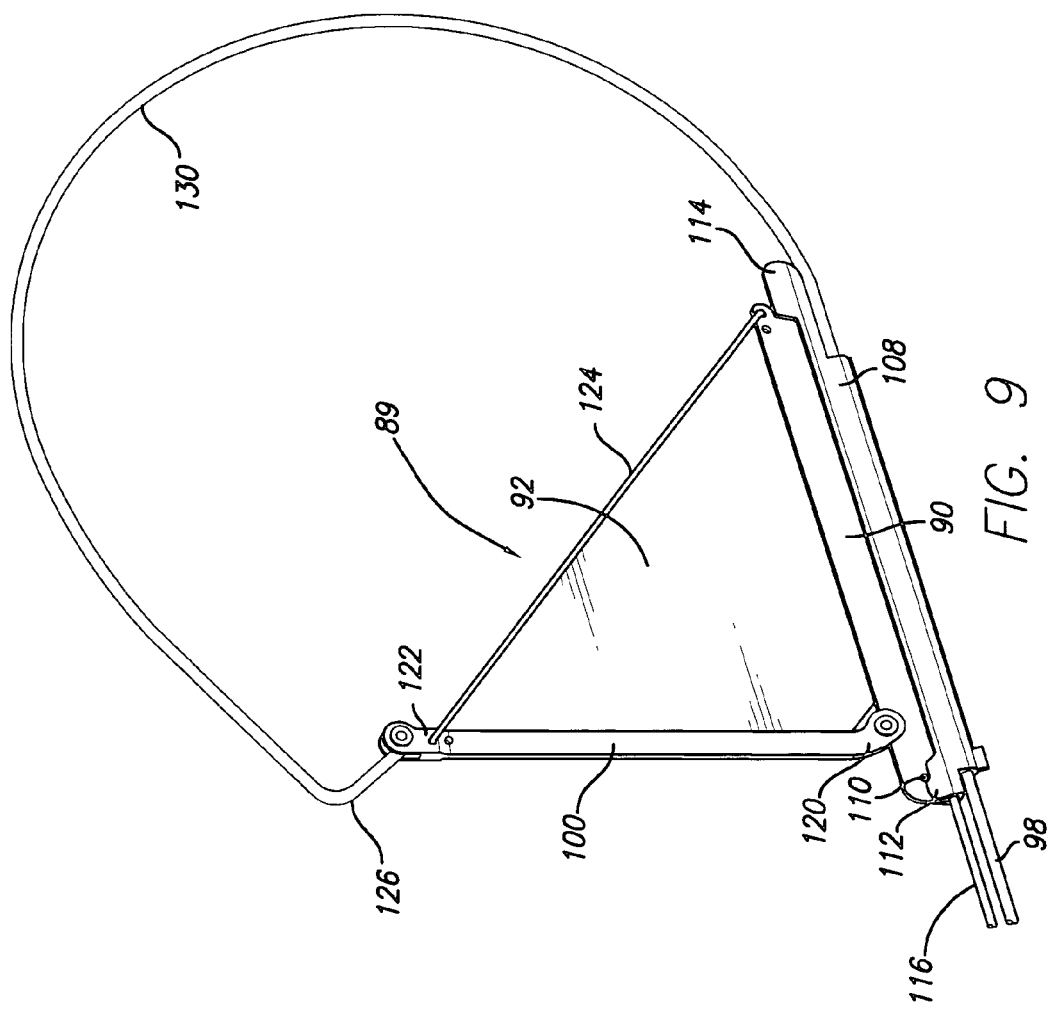
FIG. 9 shows the septum and sail of FIG. 8 with the retractor wire extended and the sail raised.
Figure 10:
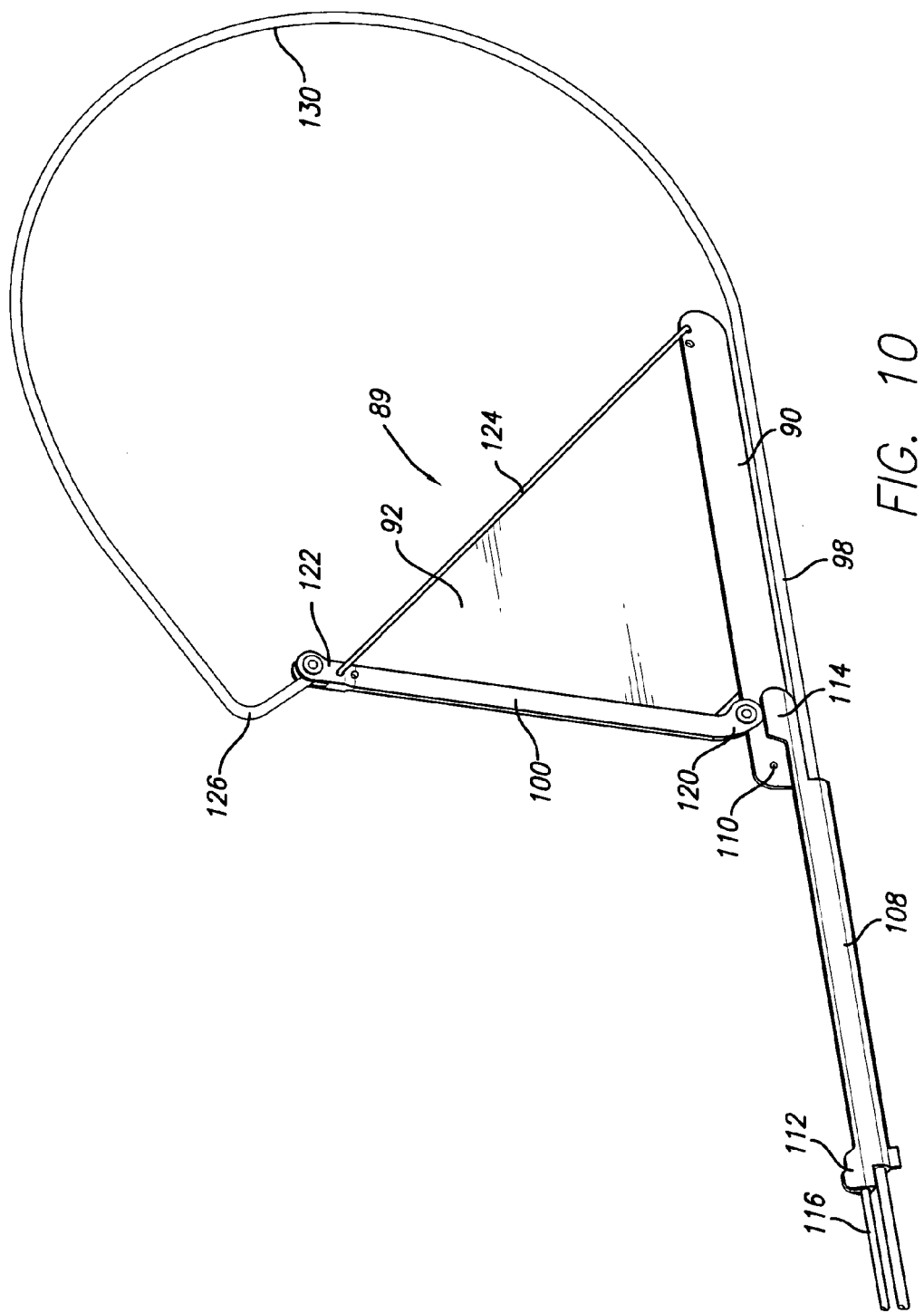
FIG. 10 shows the extended retractor wire and sail of FIG. 9 with the septum moved distally on a septum rail.

FIGS. 8 through 10 show the operation of the sliding septum 89 including the base 90 and the sail 92. For ease of reference, these figures are shown without members 86 and 88 of the tissue treatment device. The base 90 of the septum is slidably positioned within a septum rail 108 that is disposed between the cartridge member 86 and anvil member 88 on the hinge that joins these two members. Alternatively the sliding septum by be attached to a wire instead of a rail to translates the septum within and out of the tissue treatment device. A stop 110 disposed on the proximal end of the septum prevents the base of the septum from sliding completely off of the septum rail. The stop comes into contact with a proximal ridge 112 of the septum rail when the septum is fully positioned with the septum rail (see FIG. 8), and the stop comes into contact with a distal ridge 114 of the septum rail when the septum is pushed distally along the rail (see FIG. 10). A septum wire 116 attached to the proximal end of the base of the septum runs through the elongate tubular member 52 to the handle assembly 60 where a user can manipulate the wire to move the septum along the rail. One edge of the sail 92, which in this embodiment is triangular shaped, is attached to the base of the septum while another edge of the sail is connected to the sail arm or mast 100. The sail arm is composed of stainless steel or other rigid material such as a polymer, and a first end 120 is attached at to the base of the septum with a rivet, or other connector, and a second end 122 of the sail arm is connected to a first end 126 of the retractor wire 98 that is curved. As shown in FIG. 9, a sail wire 124 is attached to the remaining edge of the triangular sail, with one end tied to the distal end of the septum and the other end of the sail wire being tied to the sail arm near the second end of the sail arm. In another embodiment, the sail wire may not be used, or an alternative may be used such as a flexible tape.

Figure 11:
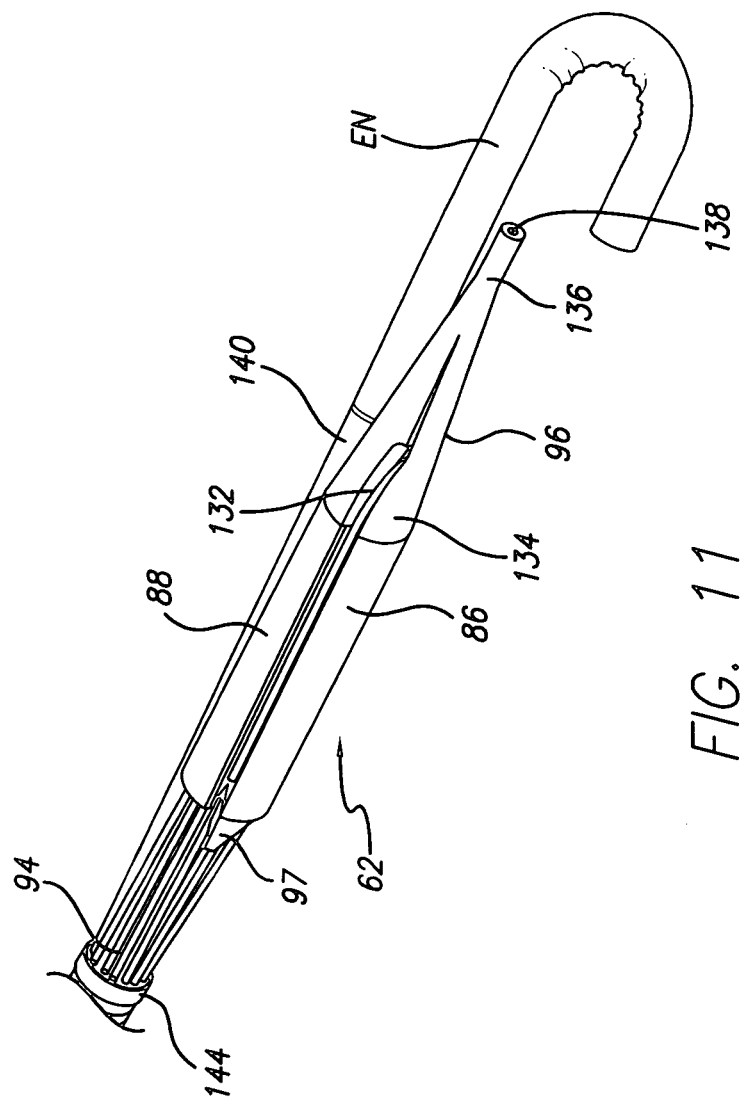
FIG. 11 shows the tissue treatment device of the gastroplasty device in a delivery configuration with an endoscope alongside.

With the first end 126 of the retractor wire 98 secured to the tissue treatment device 62, the remaining portion of the retractor wire passes through the hinge and the septum rail 108 and then through the elongate member 52, where a second end 128 of the retractor wire is positioned at the proximal end 54 of the device 50. When the tissue treatment device 62 is in the delivery position with the jaws 86 and 88 closed as shown in FIG. 11, the first end 126 of the wire retractor 98 rests inside a slit 132 formed in the split flexible tip 96 and the sail 92 is in a collapsed position so that it is folded between jaws 86 and 88. FIG. 8 illustrates how the septum is positioned within the tissue treatment device in the delivery position. To extend the retractor wire as shown in FIG. 9, the user manipulates the second end of the retractor wire and pushes it distally so that a loop of excess wire 130 extends from the tissue treatment device since the first end of the retractor wire is attached to the sail arm 100. The extended retractor wire manages tissue within the stomach cavity by blocking unwanted tissue away from the tissue treatment device. Typically the retractor wire is deployed to retract the greater curvature of the stomach, but it can also assist in smooth out the mucosal tissue surface and assist in physically positioning the treatment device against the stomach wall. Any amount of excess wire can be used since the sail arm is rigid and prevents the sail from collapsing.

In some embodiments, the retractor wire 98 is a nitinol wire, although any material, including stainless steel or a comparatively stiff polymer, can be used to form the wire structure. It is preferred that the retractor has a diameter of 0.052 inch, although different diameters can be used, such as between about 0.045 inch to about 0.075 inch. Extending the retractor wire raises the sail 92 by moving the sail arm 100 away from the tissue treatment device 62 and the base 90 of the septum 89. Targeted tissue is drawn into vacuum pods 102 and 104 located in the cartridge member 86 and the anvil member 88 when a vacuum is created, and the extended sail 92 acts as a barrier to prevent tissue from crossing over from one pod to the other. This helps to ensure that the plication or staple line formed in the stomach cavity is continuous without any stomas or holes. For example, in FIG. 45, the septum rail can be advanced a short distance distally, to accommodate tissue acquisition of the GEJ region of the stomach so that a complete plication is performed, and there is not communication between the remnant stomach and the pouch or lumen, at the level of the GEJ.

The sail 92 may be formed of any flexible material, for example polyethylene tape including polyethylene film with an acrylic adhesive, that is wrapped around and secured to the sail wire 124, which in one embodiment may be a Kevlar aramid line. Other materials that can be used to form the sail include any plastic or flexible material, for example the sail element may be cut from a sheet of material, or molded to a particular shape. Such other materials may include polyester (e.g., DACRON® from E. I. du Pont de Nemours and Company, Wilmington, Del.), polypropylene, polytetrafluoroethylene (PTFE), expanded PTFE (ePTFE), nylon, or silicone.

Figure 12:
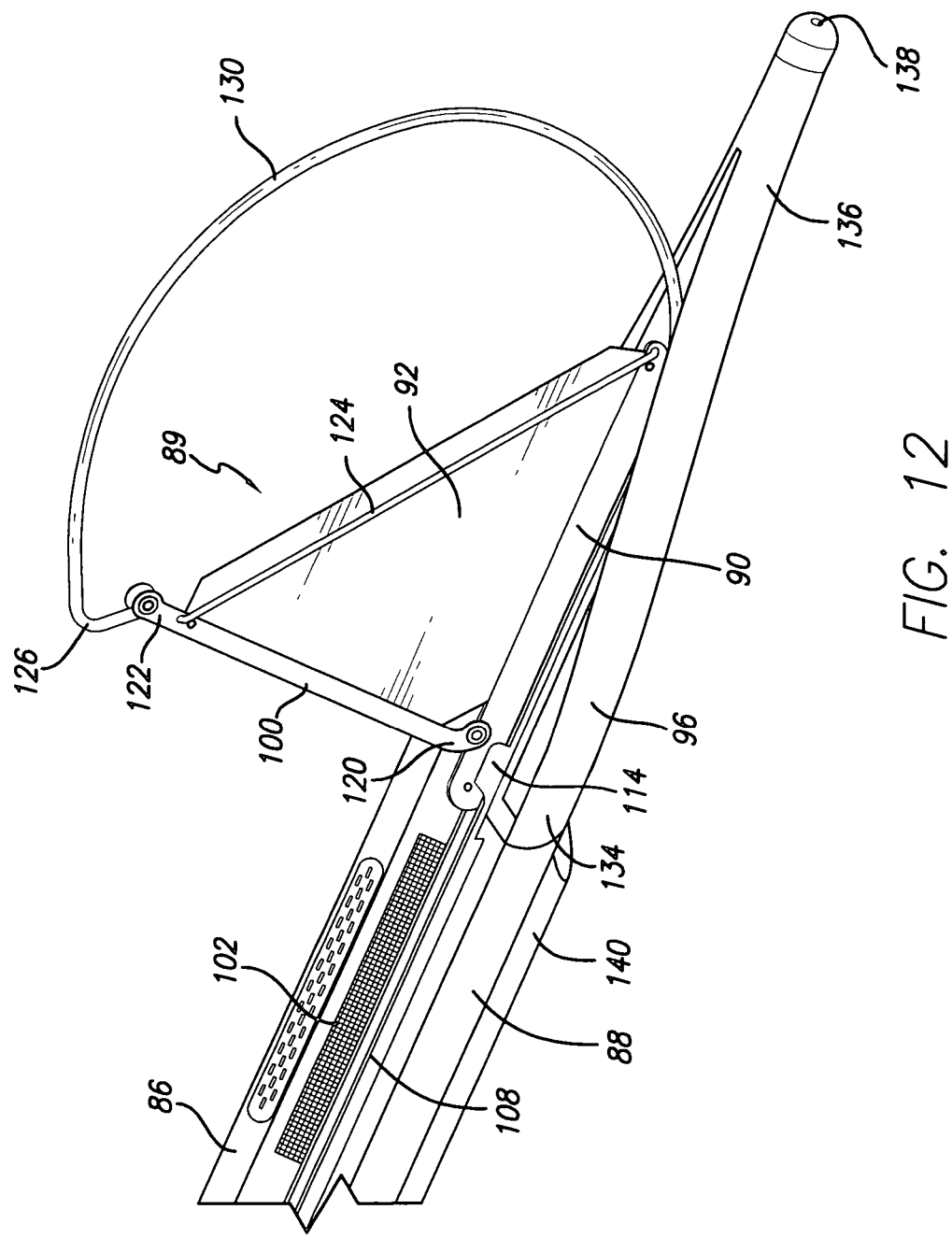
FIG. 12 shows the tissue treatment device of FIG. 11 with the jaws opened, the sail and retractor wire extended, and the septum moved distally on the septum rail such that the septum is positioned within a slit of a split flexible tip attached to the distal end of the tissue treatment device.

As shown in FIGS. 5, 11, and 12 the split flexible tip 96 includes a cylindrical body with a proximal end 134 and a distal end 136. The split 132 is formed at the proximal end of the cylindrical body and is wide enough to house the first end 126 of the retractor wire 98 when the device is in its delivery configuration (FIG. 11). The cylindrical body includes a progressive taper towards the distal end for insertion through the esophagus. Also, the cylindrical body may include a guide wire lumen 138 so the device can track along a guide wire that has been positioned within the stomach cavity. The proximal end of the split flexible tip can be attached to the distal end of the tissue treatment device 62 with an adhesive and/or mechanically with pins or a post extending from the tissue treatment device. If adhesive is used, the surface area at the cross section of the proximal end of the cylindrical body should be nearly as large as the surface area of the ends of the jaws 86 and 88. The split 132 allows the split flexible tip to open and close with the tissue treatment device, and provides a space for the retractor wire to extend through. Further, as shown in FIG. 12, when the septum 89 is advanced distally along the septum rail 108 to allow the jaws 86 and 88 to form a staple line within the acquired tissue, the base 90 of the septum stays within slit 132, and therefore, the flexible tip protects the stomach tissue from the rigid base when it is moved distally. Alternatively the septum itself may be formed of a flexible material to be atraumatic and facilitate bending. In order for the split flexible tip to open and close and be atraumatic to the tissue of the patient, it is formed of a flexible elastomeric material, such as silicone or urethane.

As best shown in FIG. 13, an endoscope shroud or sleeve 140 is attached to the backside of the tissue treatment device 62. The shroud provides a passageway for an endoscope EN, and the passageway starts from the distal end 56 of the flexible tubular member 52 and ends along the backside of the tissue treatment device. It is possible for the shroud to extend any length along the tissue treatment device, and it may even extend past the distal end of the tissue treatment device. In one embodiment, the tubular structure of the shroud is formed by layers of tape, such as polyester tape including polyester film with an acrylic adhesive, although any flexible material may be used to form the shroud. Other materials include polyethylene tape including polyethylene film with an acrylic adhesive, or polyimide tubing. In some embodiments the shroud may be molded or formed over a mandrel and then attached to the tissue treatment device. It is preferable that the shroud surface be smooth and flexible to be atraumatic to the esophagus when passed to the treatment area. A collar 142 is attached to an end ring 144 located at the distal end of the tubular member, and the proximal end of the shroud is attached to or wrapped around the collar as shown in FIG. 13. In one embodiment, the collar includes a beveled end, which allows the treatment device to be more easily introduced down the patient's esophagus. The shroud is then attached to the tissue treatment device by being wrapped around a strap 146 attached to the backside of the tissue treatment device that may also provide a passageway for the retractor wire in some embodiments. In other embodiments that do not include the strap, the shroud can be adhesively attached to the tissue treatment device. In use, the shroud tube lumen directs the endoscope EN around the jaws of the tissue treatment device for real-time viewing of the procedure. Also, the shroud 140 cradles or contains the endoscope to prevent the scope from torqueing or extending out of the insertion plane or extending into the lesser curve of the stomach organ which would affect the placement of the tissue treatment device, or in a variety of directions that may impact the resulting geometry of the gastroplasty or pouch.

In one embodiment, the cartridge member 86 may contain a removable staple cartridge 148 containing fasteners while the anvil member 88 may have an anvil 150 with dimples, such that the position and number of dimples in the anvil correspond to the number and position of fasteners within the removable staple cartridge. The removable cartridge, which is shown in FIG. 14, is removable so that during a procedure, more than one staple line may be formed within the stomach cavity using the same gastroplasty assembly 50. Referring to FIG. 14, the staple cartridge includes a staple housing 154 that stores the staples, with a top end 156 and a bottom end 158.

The top end includes staple apertures 160 where the staples are ejected from the cartridge and into the acquired tissue. To lock the removable cartridge into the cartridge member, the housing may include a locking pin 162 attached to a flexing beam 164 that is attached to the housing. There is also a lift shelf 166 disposed within the housing that provides an area to grab and lift the staple cartridge out of the cartridge member with a pair of forceps or other tool.

Referring now to FIG. 15, the removable cartridge 148 is locked in position within the cartridge member 86. As shown, the cartridge member includes a lock hole 168 that receives the flexible locking pin 162 of the removable cartridge. The cartridge member also includes a lift clearance 170 that provides access to the lift shelf 166 of the removable cartridge. To remove a dispensed cartridge from the cartridge member, an instrument can be inserted through the lock hole to press or move the locking pin away from and out of the lock hole. At the same time, another instrument can be inserted into the lift shelf to pry the cartridge out of the cartridge member. A full cartridge may then be placed into the cartridge member so that the locking pin snaps into position within the lock hole.

To deploy the staples housed within the cartridge 148, a wedge 172 may be pulled proximally through the cartridge member via a staple actuation wire 174. The actuation wire may be manipulated at the handle assembly 60, as will be described below, when staples are to be deployed into the tissue. In one embodiment, the wedge is a double blade wedge (see FIG. 25) and as the wedge is pulled proximally, the wedge engages a staple pusher 176 that is disposed over corresponding staples. As best shown by the staple apertures 160 in FIG. 14, in this embodiment the staple cartridge includes three rows of eleven staples for a total of thirty-three staples in each cartridge. The outer rows of staples are aligned with one another while the middle row of staples is staggered. A single staple pusher is configured to engage multiple staples in adjacent rows, and in one embodiment, one staple pusher engages one row of three staples. Depending on the length of the desired staple line, more or less pushers may be employed. For example, staple cartridges may include 6 to 20 pushers. FIG. 16 shows the wedge coming in contact with the most distal staple pusher. Pushers may be designed so that staples contact the anvil at different times optimizing the required force to fire the staples. Alternatively, the spacing may be derived from tissue healing properties. Or a combination of the two may effect the design of the pushers. FIG. 16A shows in more detail the wedge engaging multiple staple pushers to fire the staples against the anvil 150. The wedge in this embodiment includes a slope, typically between 15° to 30°, for example between 20° to 23°, however this angle may vary. Alternatively, the wedge may contain multiple slopes, for example a slope and then a flattened portion. Also, the staple pusher includes a complementary sloped surface 178 for slidingly engaging the sloped surface of the wedge. As the wedge engages the sloped surface of the staple pusher, the staple pusher is pushed towards the housed staples as the pusher is guided via one or more guides 180 to fire the staples.

Referring to FIG. 16, the wedge 172 is disposed within a wedge insert 182, which is near the distal end of the cartridge member 86. The wedge insert includes guides 184 that the wedge follows when it is initially pulled proximally to fire the staples. Before the device is activated and the staples are fired into tissue, the wedge is stored along the wedge insert where it does not engage or begin to push the stapler pusher 176 toward the staples. While the wedge is in this starting position, it is also held in place during handling by a shear pin 186 that is molded into the staple cartridge 148. The shear pin ensures that the wedge does not begin to contact the staples in the cartridge. In one embodiment, to move the wedge proximally out of the wedge insert and past the shear pin, sufficient force is translated down the staple actuation wire 174 to the wedge to break the shear pin away from the staple cartridge so that the wedge is free to move proximally along the cartridge member. If after firing the staples of one staple cartridge and the tissue treatment device 62 is to be reloaded with another staple cartridge, the staple cartridge is removed as described above and the wedge is manually pushed distally along the cartridge member until it is positioned back into its starting position within the wedge insert. It is important that the wedge is pushed back to the starting position, otherwise, when another cartridge is loaded into the device staples may be pre-fired due to the position of the wedge. Then, another staple cartridge is loaded into the cartridge member, and the shear pin molded into this staple cartridge will hold the wedge in its starting position during handling.

A staple 188 is shown in FIG. 17 and exemplifies one embodiment of a staple that is used in this embodiment of the removable staple cartridge 148. The staple is formed of a round wire and includes a base 190 with two legs 192 each having a chisel point 194. However, other types of wire may be used to form the staple, such as flat wire or a wire with any cross-sectional shape. The staple may include notches for preferential bending into a desired configuration with reduced force. It is desirable that the staple is formed of titanium, however, other rigid material may be used such as stainless steel. In this embodiment, the diameter of the wire used to form the staple is about 0.009 inch, but may be smaller or larger, e.g., between about 0.007 inch to about 0.012 inch. Further, the length of the staple in this embodiment is about 5.3 mm, however, the length of the staple may range from about 3.5 mm to about 6.0 mm, or more preferably between 4.8 mm and 5.8 mm. The width of the staple's base is between 2 mm and 4 mm, and more preferably is about 3 mm.

The tissue treatment device 62 is connected to the distal end 56 of the elongate member 52 by connecting member 94 that is attached to an end ring 196 disposed at the distal end of the elongate member. A cross-sectional view of the end ring is shown in FIG. 18 and shows several apertures 198 disposed through the end ring to provide a passageway for the endoscope, vacuum tubes and various wires. In one embodiment, the apertures are designated as follows: aperture 198a is a passageway for the endoscope, aperture 198b is a passageway for the cartridge member vacuum tube, aperture 198c is a passageway for the anvil member vacuum tube, aperture 198d engages the connecting member 94 that is attached to the tissue treatment device, aperture 198e is a passageway for the septum wire 116, aperture 198f is a passageway for the retractor wire 98, aperture 198g is a passageway for the opening cable (discussed below), aperture 198h is a passageway for the outer clamping cable (discussed below), aperture 198i is a passageway for the inner clamping cable (discussed below), and aperture 198j is a passageway for the staple actuation wire 790. In other embodiments, the apertures may be rearranged in any design and additional apertures may be disposed through the end ring for additional wires.

Each of members 86, 88 may have openings to allow for the routing and passage of clamping cables through the device for enabling cartridge member 86 and anvil member 88 to be clamped together and opened. FIGS. 19 and 20 show partial cross-sectional views taken along the tissue treatment device 62 with the vacuum tubing and cables routed through the device. As shown, cartridge vacuum tube 200 and anvil vacuum tube 202 may be routed through elongate member 52 into a proximal end of each cartridge member 86 and anvil member 88 for fluid connection with respective openings

102, 104. Outer clamping cable 204 and inner clamping cable 206 may be passed through elongate member 52 around vertical pulleys 208 in the cartridge member and across to the anvil member where the ends may be held in the anvil member with ball crimps. To clamp cartridge member and anvil member closed, the cables 204 and 206 are pulled proximately using the handle assembly 60. The closed configuration of the tissue treatment device is shown in FIG. 19. Opening cable 210 may be passed through elongate member 52 around the horizontal pulley 212 in the cartridge member and around an open cam 214 to the anvil member, where the end is held in the anvil member with a ball crimp. Cartridge and anvil members may be opened with respect to one another by pulling or tensioning the opening cable proximately using the handle assembly. This open configuration is shown in FIG. 20.

Referring now to FIGS. 21 through 24, another embodiment of a tissue treatment device 62 is shown to include a distal clamping cable 216 to help close or clamp the cartridge and anvil members 86, 88 together. In the embodiment shown, a proximal end of the distal clamping cable is attached at the handle 60 and a distal end of the distal clamping cable is attached to the distal end of the tissue treatment device. As shown in FIG. 21, cartridge vacuum tube 200 and anvil vacuum tube 202 may be routed through elongate member 52 into a proximal end cap 218 of each cartridge member and anvil member for fluid connection with respective openings 102, 104. Proximal outer clamping cable 204 and proximal inner clamping cable 206 may be passed through elongate member and around proximal vertical pulleys 208 in the cartridge member and across to the anvil member where the ends may be held in the anvil member with ball crimps. FIG. 23 shows the proximal end of the tissue treatment device with the proximal end cap removed showing the proximal vertical pulleys, and the proximal inner and outer clamping cables 204, 206 including coil pipes 220. In this embodiment, the distal clamping cable is also passed through the elongate member into the tissue treatment device and around a distal vertical pulley 222 housed within a distal end cap 224 of the cartridge member and across to the anvil member where the end may be held in the anvil member with a ball crimp. FIG. 22 shows the distal end of the tissue treatment device with the distal end cap removed to show the distal vertical pulley. To clamp the cartridge member and anvil member closed, cables 200, 202, and 216 are pulled proximately by the user at the handle assembly. While the proximal cables provide a clamping force at the proximal end of the tissue treatment device, the distal cable provides a clamping force at the distal end of the tissue treatment device to provide a more even clamping force across the entire length of the tissue treatment device. In this embodiment, the proximal opening cable 210 may be passed through elongate member around the proximal horizontal pulley 212 as discussed above.

In another embodiment, one of the proximal clamping cables 204 or 206 can be re-routed to the distal vertical pulley 222 to become the distal clamping cable 216. This embodiment still provides a clamping force at the distal end of the tissue treatment device without having to add an additional cable to the system. Providing a clamping force at the distal end of the tissue treatment device 62 helps compensate for any deflection of the jaws caused by the acquisition of tissue.

Figure 25A:
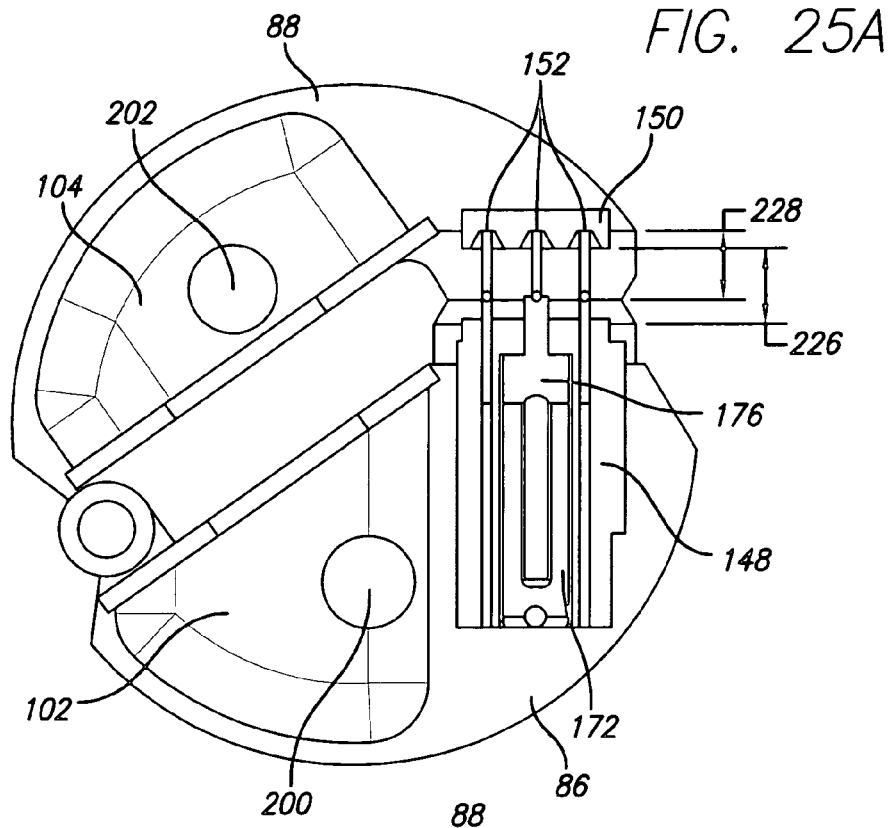
FIG. 25A shows a partial cross-sectional view of the tissue treatment device in a closed position with the anvil member aligned with the cartridge member.

A cross-section view of one embodiment of the tissue treatment device 62 is shown in FIG. 25A detailing the alignment of the dimples 152 of the anvil 150 with the staple apertures 160 of the staple cartridge 148. This figure also shows the double-blade wedge 172, which preferably has a height of about 0.230 inch, and the staple pusher 176, which preferably has a height of about 0.128 inch. The staple cartridge has a depth of about 0.282 inch in one embodiment and about 0.272 inch in another embodiment. A clamp gap of the device, designated as line 226, which is the distance between the staple apertures of the staple cartridge and the contact edge of the anvil, is about 0.070 inch and more preferable about 0.090 inch. Also, a closed staple height is designated as line 228 and is the height of the staple after it has been fired from the cartridge and crimped by the anvil. In one embodiment the closed staple height is about 0.070 inch, and in another more defined embodiment, the closed staple height is 0.095 inch. The cross-section of the dimples are shown to have a cross-sectional shape with tapered side-walls and a flat bottom. However, it has been contemplated that the cross-sectional shape of the dimples may have any shape, including V or U shapes. Further, the depth or pocket of the dimples may vary between about 0.010 inch to about 0.030 inch, and it is preferred that the pocket of the dimple be about 0.020 inch.

Figure 25B:
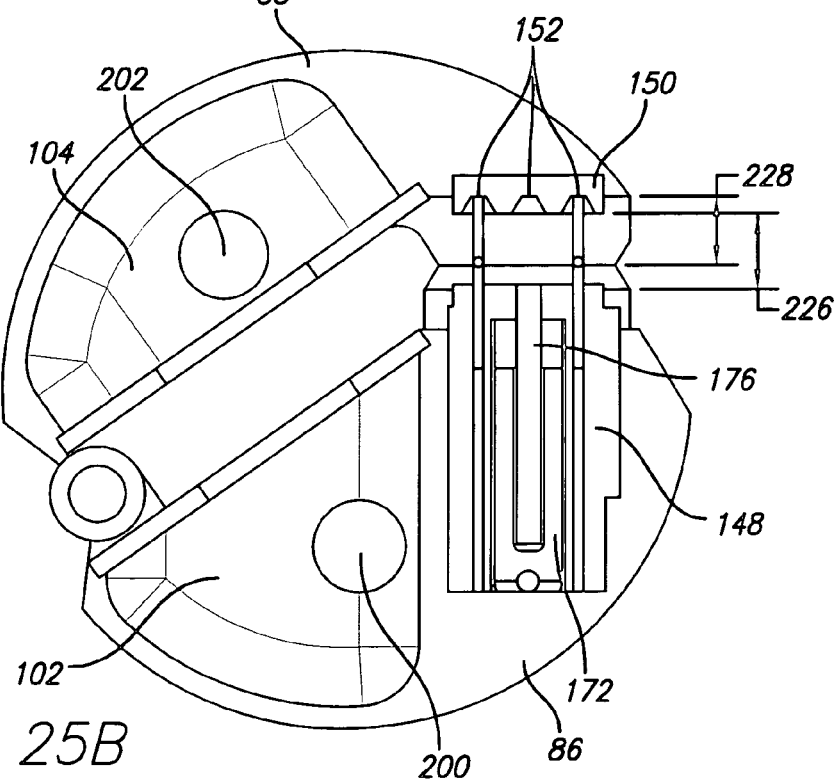
FIG. 25B shows a partial cross-sectional view of the tissue treatment device in a closed position with the anvil member off-set from the cartridge member.

In the embodiment shown in FIG. 25A, the dimples 152 are in-line with the staple apertures 160 when the jaws are fully closed so that when the staples are ejected from the staple cartridge, the chisel points or ends of the staple legs will hit the center of the dimples. However, it is possible that when tissue is acquired by the tissue treatment device, the anvil member 88 may be prevented by the tissue positioned within the tissue treatment device from fully clamping against the cartridge member 86. This may cause a misalignment so that the chisel points of the staple legs will not be centered within the dimples of the anvil when the staples are fired into the acquired tissue. In one embodiment shown in FIG. 25B, the anvil member is offset about 0.010 inch outboard from the cartridge member to compensate for the incomplete jaw closure when tissue is acquired. Alternatively or in addition, the anvil member may be angled with respect to the longitudinal axis of the jaws to minimize deflect of the distal end of the jaws. As shown in FIG. 25B, with the jaws 86, 88 completely closed, the chisel points of the staple legs hit the sides of the dimples because the anvil member is offset in this figure. However, as one skilled in the art can recognize, when the jaw closure is incomplete because of the acquired tissue positioned between the cartridge and anvil members, the staples fired into the tissue will meet near the middle of the dimples due to the anvil being offset. It has also been contemplated that the anvil 150 can be repositioned on the anvil member to compensate for the incomplete jaw closure as well.

During a procedure, when the tissue treatment device 62 acquires tissue between the jaws or cartridge and anvil members 86 and 88, it is desired to achieve parallel jaw closure along the length of the jaws from the proximal end to the distal end of the jaws to help ensure a successful staple line is placed within the acquired tissue. One method of ensuring parallel jaw closure is to have both distal and proximal clamp cables as described with reference to FIGS. 21 through 24. In this embodiment, the distal clamp cable 216 provides a clamping force at the distal end while the proximal clamping cables 204 and 206 provide a clamping force a the proximal end of the jaws.

Figure 26:
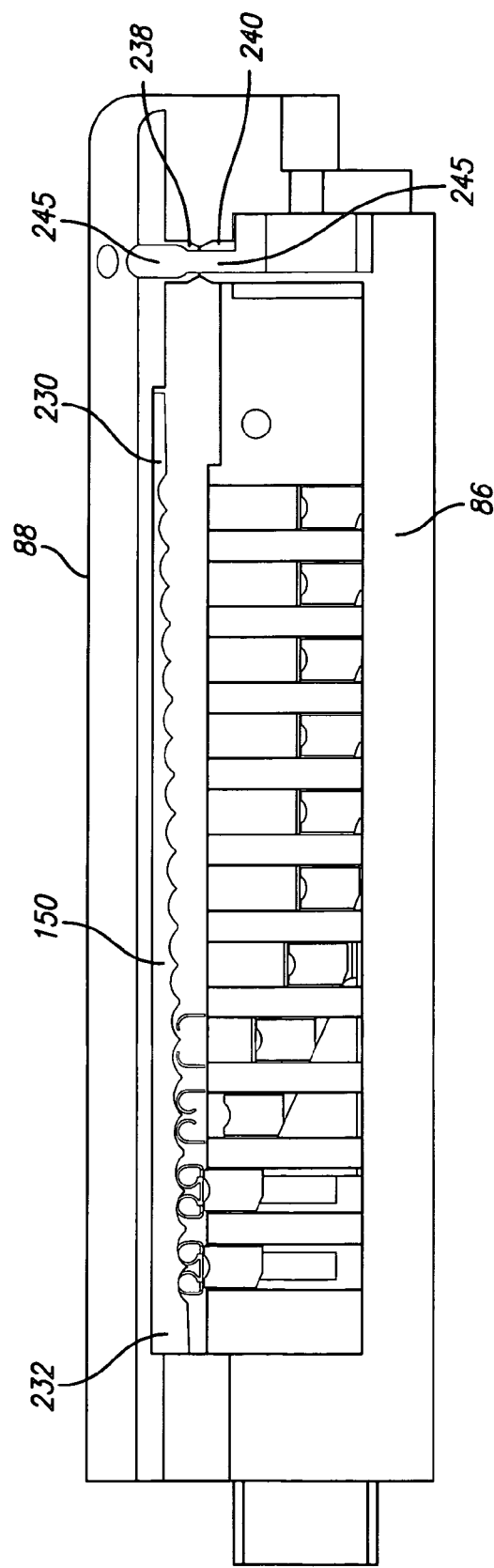
FIG. 26 shows a partial cross-sectional view of an embodiment of the tissue treatment device having a tapered anvil.

In another embodiment where only proximal clamping cables are provided to clamp the jaws or cartridge and anvil members 86 and 88, the distal end of the anvil member may deflect or twist in relation to the proximal end of the anvil member when the tissue treatment device 62 closes after acquiring tissue. If the distal end of the anvil member deflects away from the cartridge member, then during the firing of the staples, the staples at the distal end of the staple cartridge may not be fully crimped against the anvil 150 of the anvil member. To compensate for the possible deflection of the anvil member, FIG. 26 depicts the anvil in one embodiment being tapered from a proximal end 230 to a distal end 232 giving the anvil a wedge shape. In other words, the distal end of the anvil has a greater thickness than the proximal end, thereby keeping the anvil's surface parallel to the surface of the cartridge member even though the distal end of the anvil member may deflect or twist in relation to the proximal end when the jaws of the tissue treatment device are clamped together after acquiring tissue. As an example, the proximal end of the anvil may have a thickness of about 0.030 inch, and the anvil may taper up to the distal end of the anvil having a thickness of about 0.048 inch.

Figure 27A:
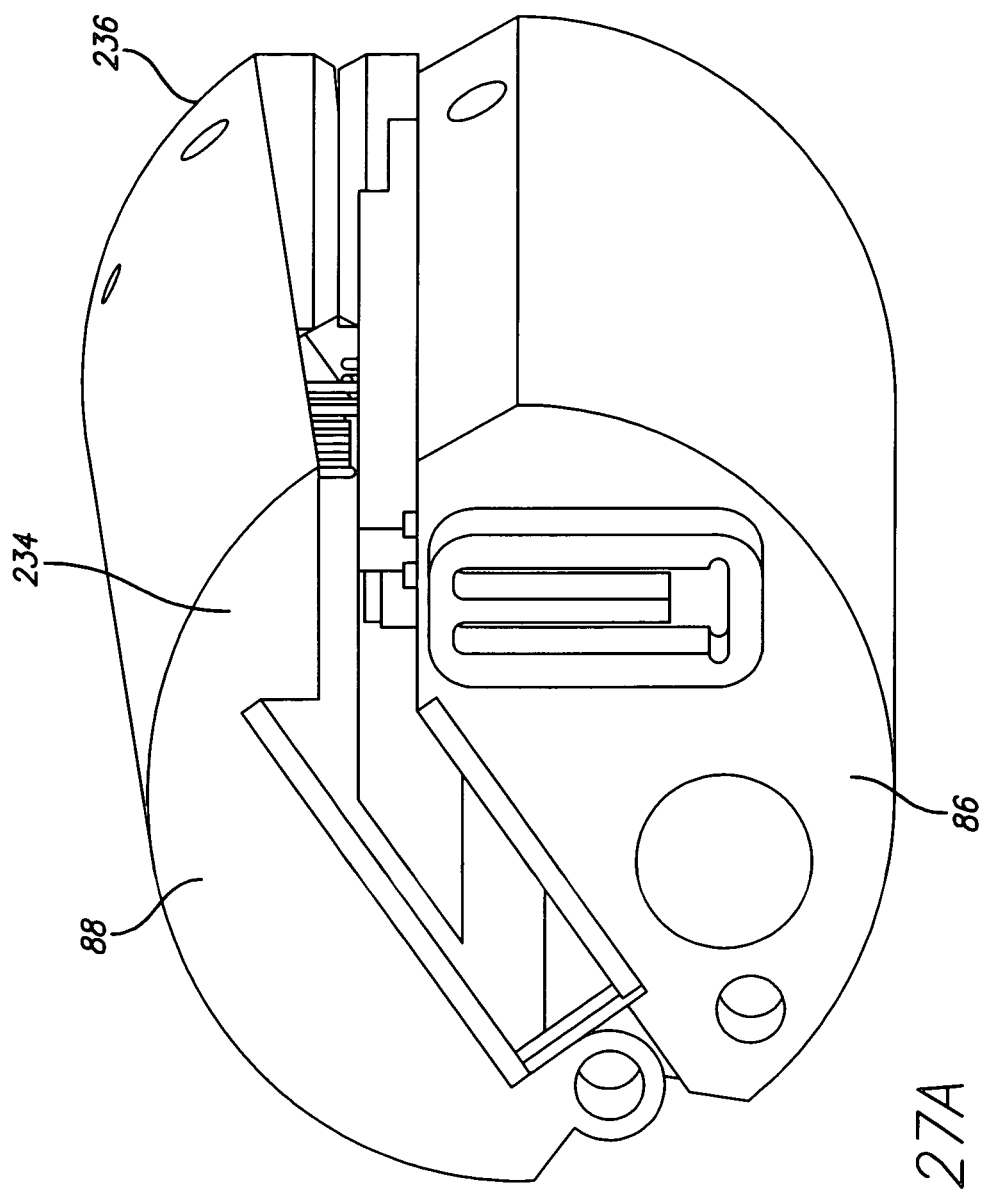
FIG. 27A shows another embodiment of the tissue treatment device having a bent or twisted anvil member.

In another embodiment, the anvil member 88 may be prebent or twisted to compensate for any deflection caused by the clamping of tissue acquired within the tissue treatment device. As shown in FIG. 27A, the anvil member has been twisted so that when the tissue treatment device 62 is in its closed position, a distal end 234 of the anvil member is located closer to the cartridge member 86 than a proximal end 236 of the anvil member. This twist in the anvil member helps keep the anvil's surface parallel to the surface of the cartridge member when acquired tissue between the jaws of the tissue treatment device deflects the distal end of the anvil member away from the cartridge member.

Figure 27B:
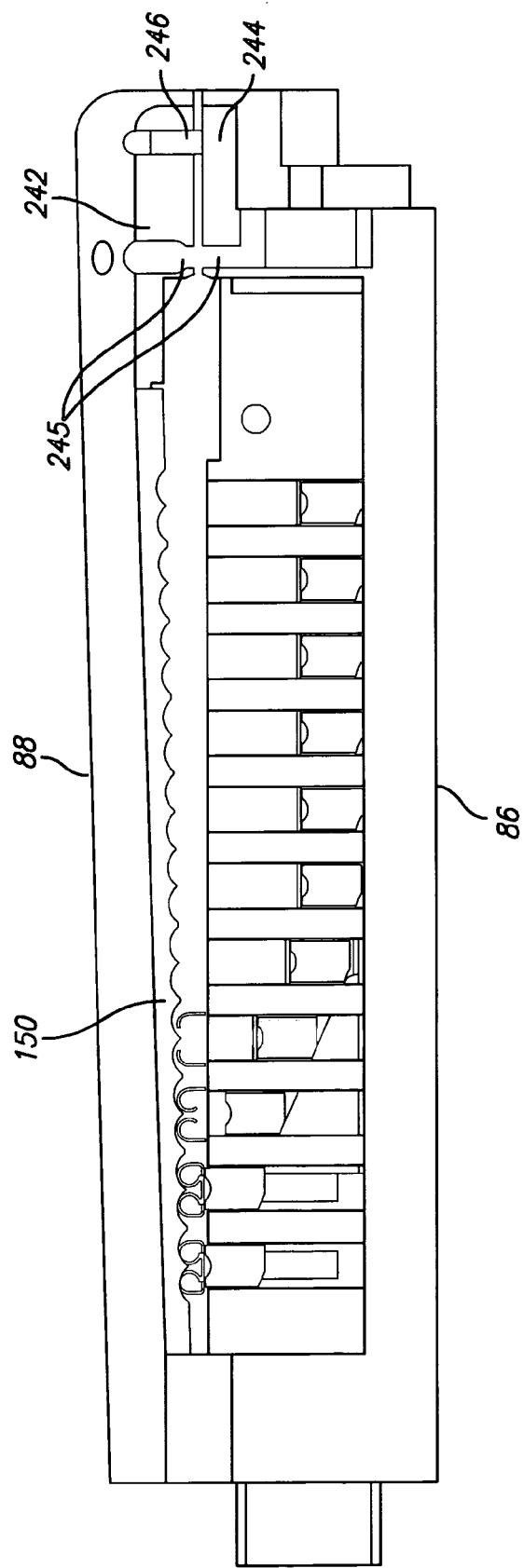
FIG. 27B shows a partial cross-sectional view of an embodiment of the tissue treatment device having a wide stop and a pin at its proximal end to pinch the distal end of the device when it is closed.

In another embodiment, stops can be disposed on the proximal end of the tissue treatment device 62 to more heavily bias the distal end of the anvil member 88 towards the cartridge member. FIG. 26 shows one embodiment where an anvil stop 238 and a cartridge stop 240 are disposed opposite one another at the proximal end of the tissue treatment device to prevent the anvil member from fully closing against the cartridge member. This is done to provide an optimal distance between the cartridge member and the anvil so that the staple is crimped into an ideal B-shape. If the stops 238 and 240 are removed, the staple may become crimped too tightly and may not be able to hold a fold of tissue together without tearing out of the tissue. The outer clamping cables (not shown in FIG. 26) may pass through a lumen 245 of the stops. In another embodiment shown in FIG. 27B, a wide anvil stop 242 is disposed on the proximal end of the anvil member and a wide cartridge stop 244 is disposed on the proximal end of the cartridge member opposite the wide anvil stop. There is also an adjustable screw or a stationary pin 246 disposed within the wide anvil stop, that extends partially past the surface of the wide anvil stop. When the jaws 86 and 88 are clamped together, the pin in the wide anvil stop comes into contact with the surface of the wider cartridge stop, and as the clamping cables continue to apply force to close the jaws, a lever action is created that biases the distal end of the anvil member to pinch against the distal end of the cartridge member as shown in FIG. 27B. This action created by the wide stops helps to compensate for deflection of the distal end of the jaws when tissue is acquired with the tissue treatment device, as further described below.

It has also been contemplated that to help compensate the deflection caused by tissue between the cartridge and anvil members 86 and 88, the embodiment including the wide stops 242 and 244 (FIG. 27B) can be combined with the embodiment having the twisted anvil member (FIG. 27A), and/or the embodiment with the tapered anvil (FIG. 26). Further, these embodiments or combination of embodiments may be used in combination with the embodiment of the tissue treatment device that includes distal clamping cables (FIGS. 21-24).

Figure 28A:
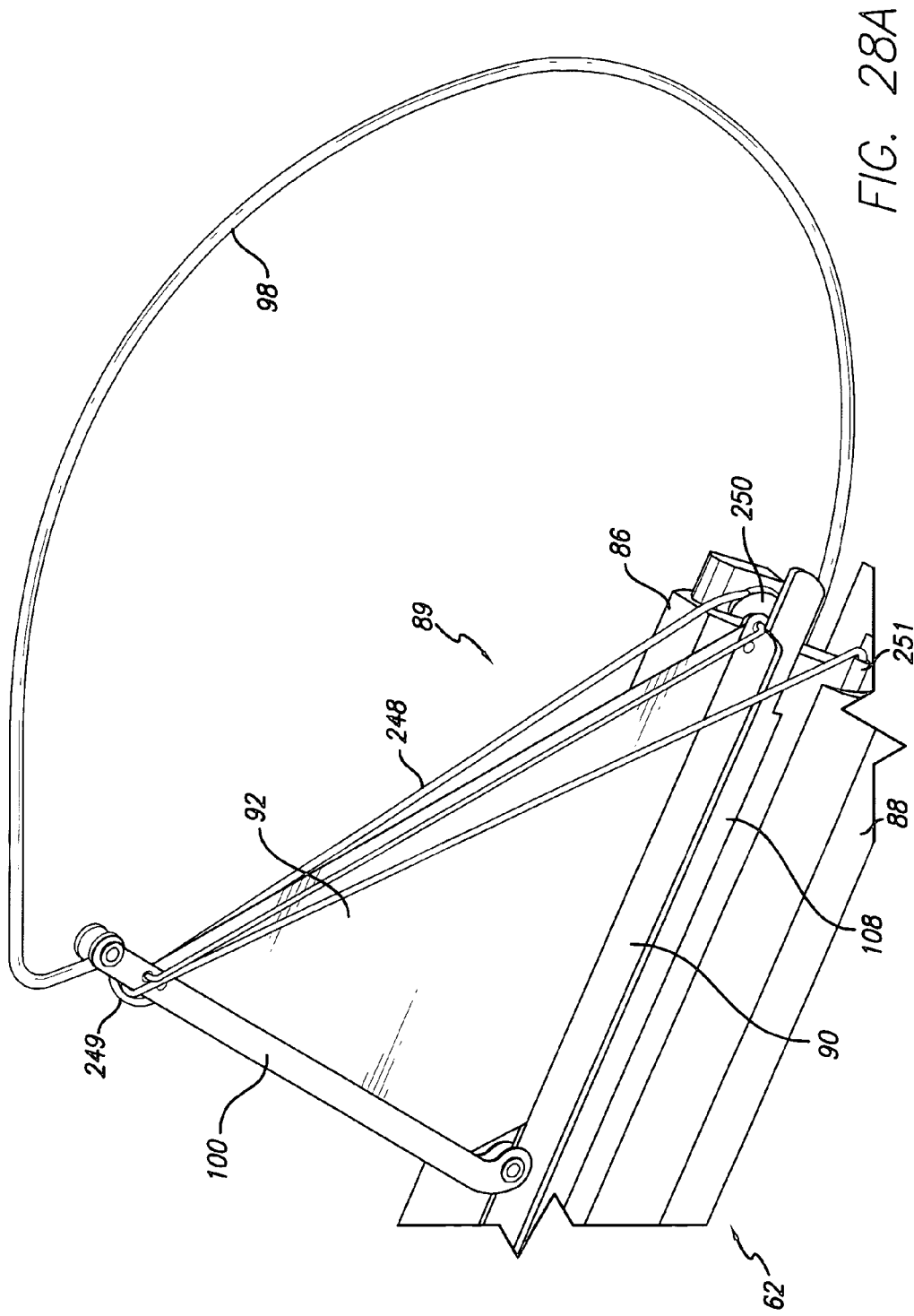
Figure 28C:
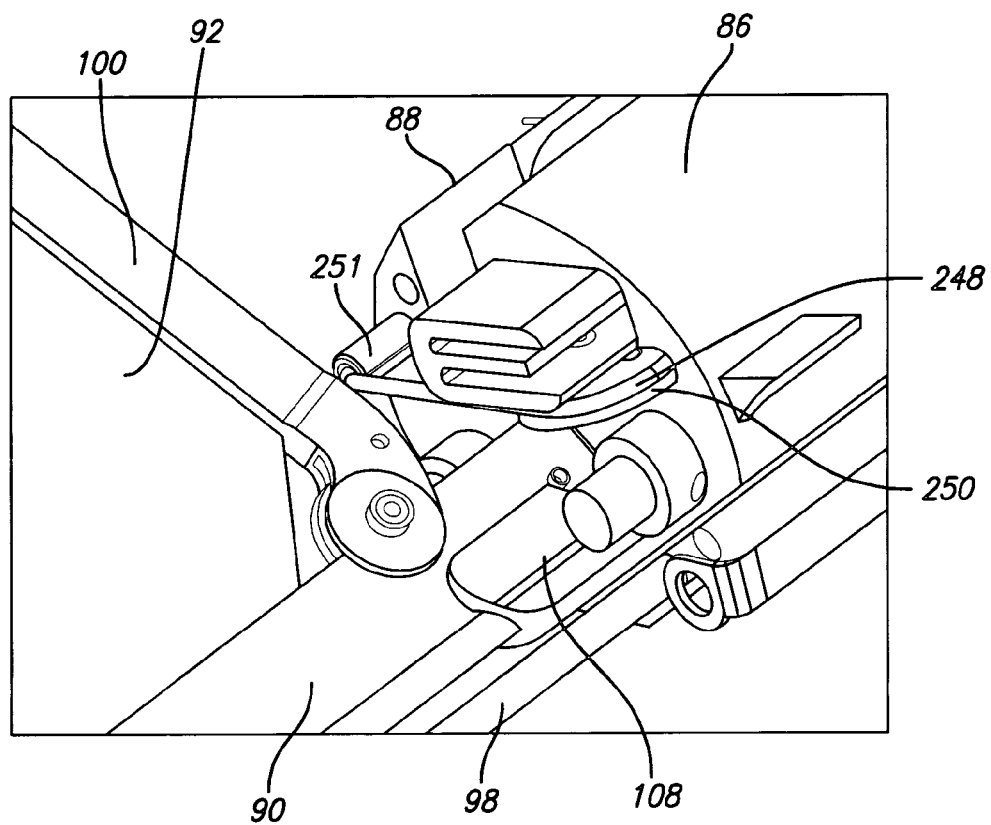

Another embodiment is shown in FIGS. 28A through 28C, where a wire is connected to the distal end of the jaws 86 and 88 to assist the proximal clamping cables 204 and 206 in closure of the tissue treatment device 62. Referring to FIG. 28A, a Kevlar rope 248 is shown attached to a spring clip 249 on the back side of the sail arm 100. The Kevlar rope runs from the handle assembly 60, through the length of the elongate member 52, through the cartridge member 86, around a pulley 250 disposed on the distal end of the cartridge member, through the spring clip, and into the distal end of the anvil member where it is attached with a knot or ball crimp 251. The Kevlar rope may be formed of any other flexible wire. In this embodiment, when loading the septum 89 in the jaws initially, slack is left in the Kevlar rope and the jaws are closed with the device in a delivery configuration. Then, when the device is in the desired position within the stomach and the jaws are opened, the septum is advanced along the septum rail 108 and the sail 92 is raised by advancing the retractor wire 98. The initial slack in the Kevlar rope allows these movements without putting tension on the rope. In practice, the septum is then pulled back between the jaws as shown in FIG. 28A. As shown in FIG. 28B, after the targeted tissue is vacuum-acquired and the septum moved to the distal end of the septum rail, the jaws are closed using the proximal clamping cables as previously described. At this point tension is applied to the Kevlar rope by pulling an end of the Kevlar rope located at the handle assembly, which releases the rope from the spring clip as shown in FIG. 28C. The septum including the sail arm are distal to the Kevlar rope at this point. Further tension is applied to the Kevlar rope to assist the closure of the jaws at the distal end. After completion of stapling, tension on the Kevlar rope is released and the jaws are opened to fully release the tissue. The retractor wire is then pulled proximally to collapse the sail and the septum is then moved proximally along the septum rail so that it is positioned between the jaws. During this procedure, slack in the Kevlar rope prevents the sail arm from rubbing on the Kevlar rope. The jaws are then fully closed with the septum inside, and the device is withdrawn from the stomach cavity. With the Kevlar rope being activated after the proximal clamp cables, usually more than 50% of the total clamping force comes from the proximal end of the jaws. This embodiment assists in assuring a complete closure or clamping of the device against folds of tissue that are acquired between the jaws of the device. The jaws may close to distal stops to prevent over-clamping at the distal end.

Figure 29A:
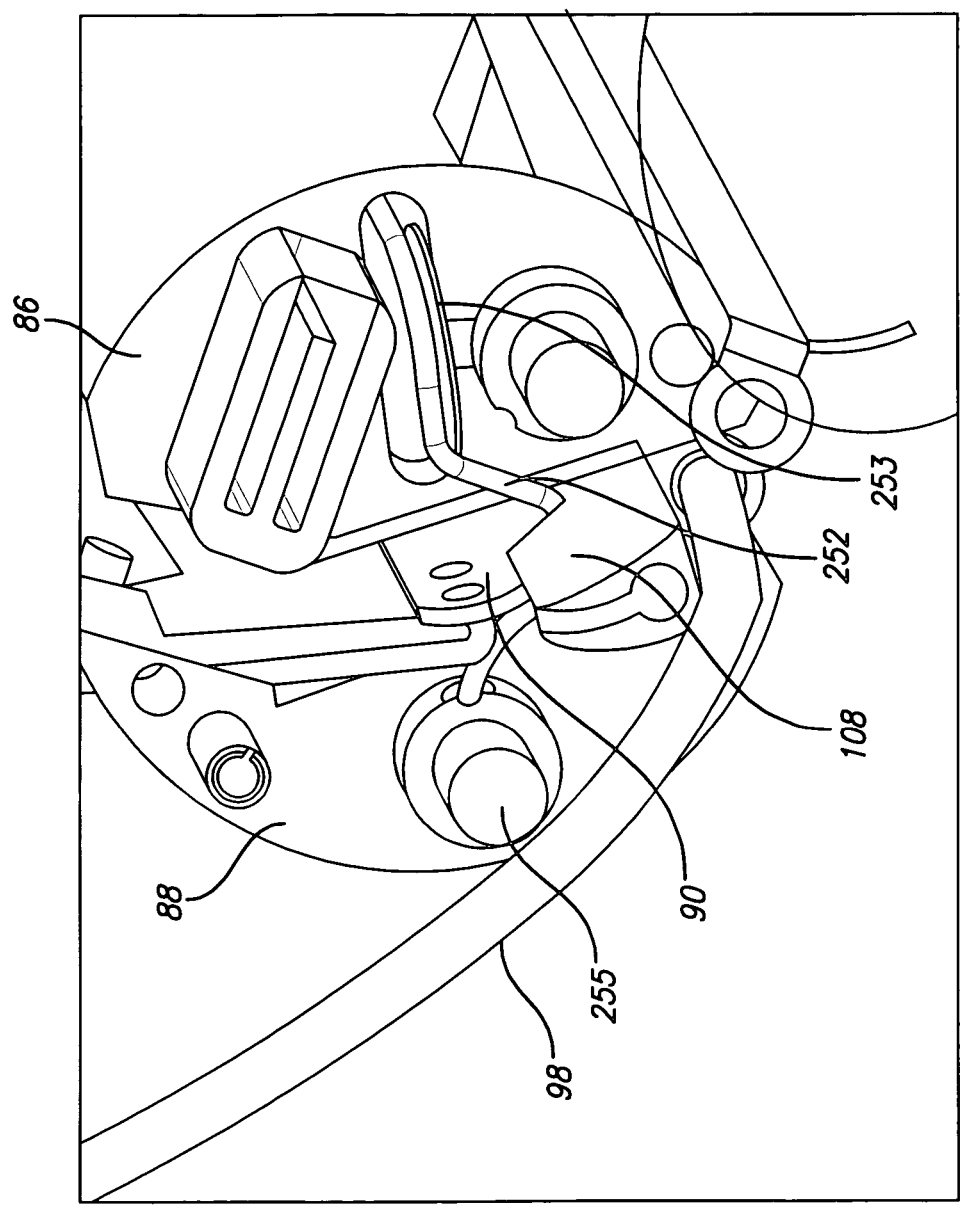
Figure 29B:
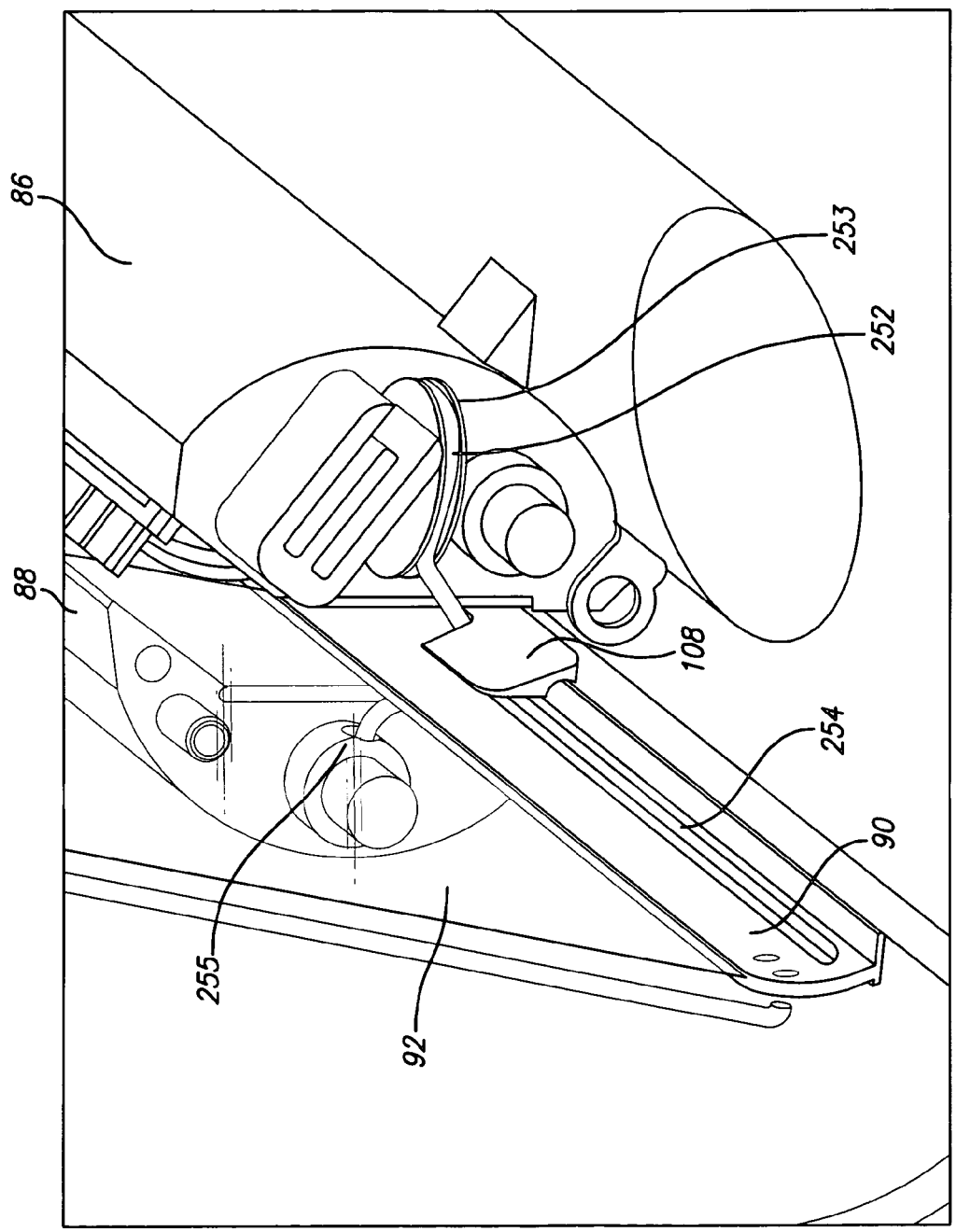

Referring now to FIGS. 29A through 29C, another embodiment of a cable connected to the distal end of the jaws 86 and 88 is shown to assist the proximal clamping cables 204 and 206 in completely closing the tissue treatment device 62. In this embodiment, a stainless steel cable 252 is routed from the handle assembly 60, through the elongate member 52 and the cartridge member 86, around a pulley 253 disposed within the distal end of the cartridge member, and through a slot 254 disposed within the base 90 of the septum 89 to the anvil member 88 where the cable is attached with a ball crimp 255. While the septum is in any position but fully extended distally past the jaws of the device, the slot is relatively close to the hinge between the jaws as shown in FIG. 29A, which prevents the cable from being aligned horizontally between the pulley and the ball crimp. When the device is delivered to the stomach cavity, and before tissue is clamped between the jaws, there is no tension on the stainless steel cable. After the tissue is acquired and the septum is moved distally along the septum rail 108, the cable slides through the slot of the base as shown in FIG. 29B. When the septum is at the distal end of the septum rail as shown in FIG. 29C, the cable is positioned within a through hole 256 located at a proximal end of the slot within the base of the septum. The slot of the base is raised at the proximal end of the septum so that the through hole is aligned with the cable as shown in FIG. 29C. After applying at least 50% of the total intended force on the proximal end of the device with the proximal clamping cables 204 and 206, tension is applied on the stainless steel cable by pulling a proximal end of the cable proximally at the handle assembly. With the through hole of the proximal raised portion of the slot aligned with the stainless steel cable, no force is applied on the septum and the cable provides additional force to fully clamp the jaws against the acquired tissue. Upon completion of the stapling process, tension on the stainless steel cable is fully released and jaws are opened to release the acquired tissue. When pulling the septum back to its proximal position within the septum rail, the cable slides along the slot to the distal end of the base as shown in FIG. 29A, and any slack in the cable is collected under endoscopic view without applying significant force to the cable. The jaws are closed and the device may be removed from the stomach cavity. Using the steel cable to clamp the distal end of the jaws helps to ensure the jaws are fully closed before firing staples into the acquired tissue.

Figure 30:
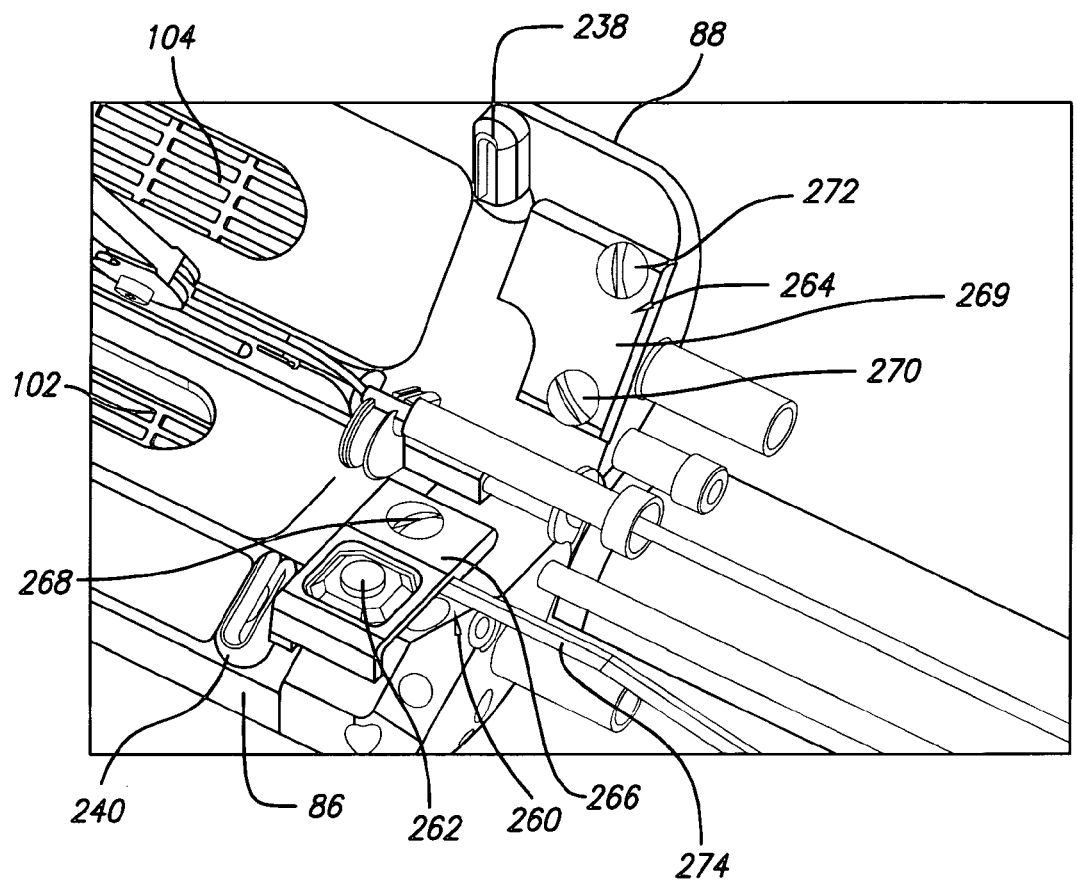
FIG. 30 shows the proximal end of the tissue treatment device having an electrical switch for detecting closure of the jaws.

Several embodiments of the tissue treatment device 62 have also been contemplated that detect complete closure of the jaws 86 and 88 at that handle assembly 60. These detection mechanisms, may be optical, electrical, mechanical, tactile, pressure measurements and the like. In one embodiment depicted in FIG. 30, an electrical switch 260 is disposed at the proximal end of the tissue treatment device and trips when the jaws reach a certain distance between them or when they are fully closed. The electrical switch includes a push-button switch 262 disposed on one jaw, in this embodiment the cartridge member 86, and a pusher 264 disposed on the other jaw, in this embodiment the anvil member 88. The push-button switch is attached to a frame 266 that is attached to the cartridge member with a fastener, such as a screw 268. On the anvil member, the pusher includes a metal plate 269 attached to the anvil member with an inner screw 270. An outer screw 272 that is adjustable is attached to the metal plate and the anvil member. The distance of tripping the push-button switch is adjustable with the outer screw of the pusher, and the pusher is designed to actuate the switch at a distance between about 0.000 inch to about 0.040 inch. Also, the electric switch is designed to allow the jaws to continue to move towards each other while the push-button switch continues to be in the electrically "closed" position. Other types of switches other than a push-button type can be used. Once the push-button switch is tripped, electrical wires 274, which provide an electric current to the switch, send a signal back to the handle assembly 60 where an indicator, such as an LED light, indicates to the user that the jaws of the device are closed. Further, the electrical switch may also be disposed on the distal end of the tissue treatment device, or one electrical switch can be attached to the proximal end while a second electrical switch can be attached to the distal end of the tissue treatment device.

Figure 31:
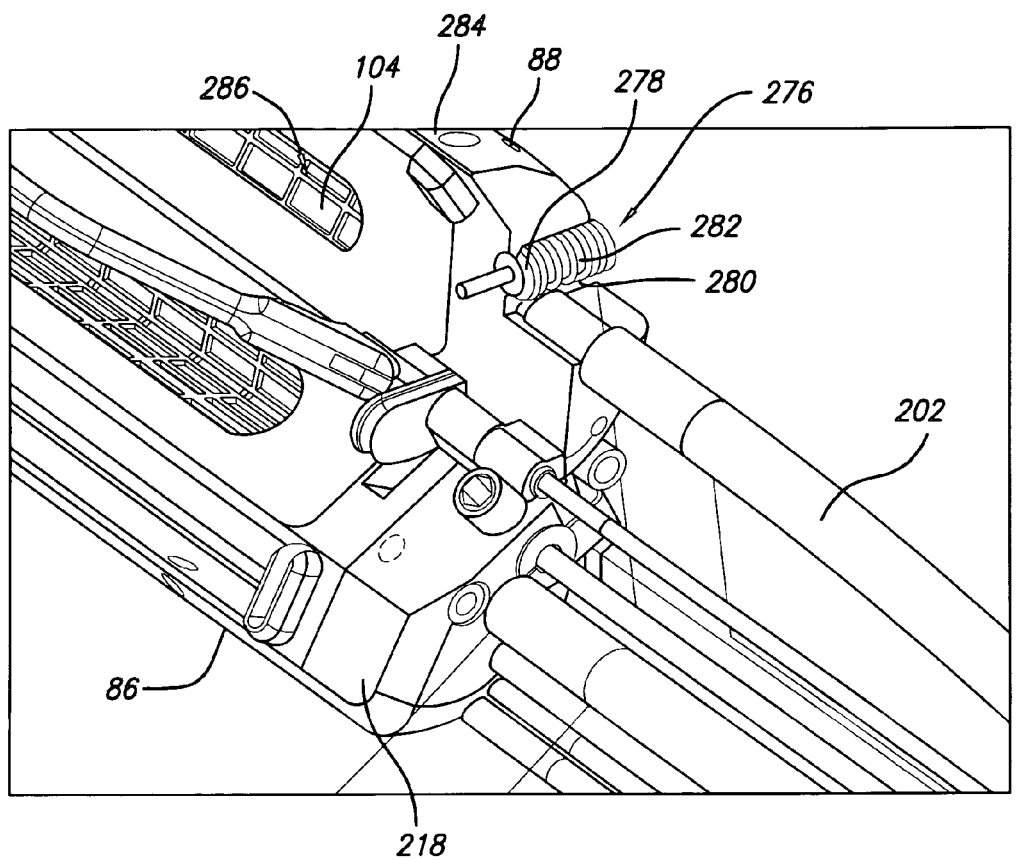
FIGS. 31 and 32 show a partial cross-sectional view of the proximal end of the tissue treatment device having a vacuum detection device for detecting closure of the jaws.
Figure 32:
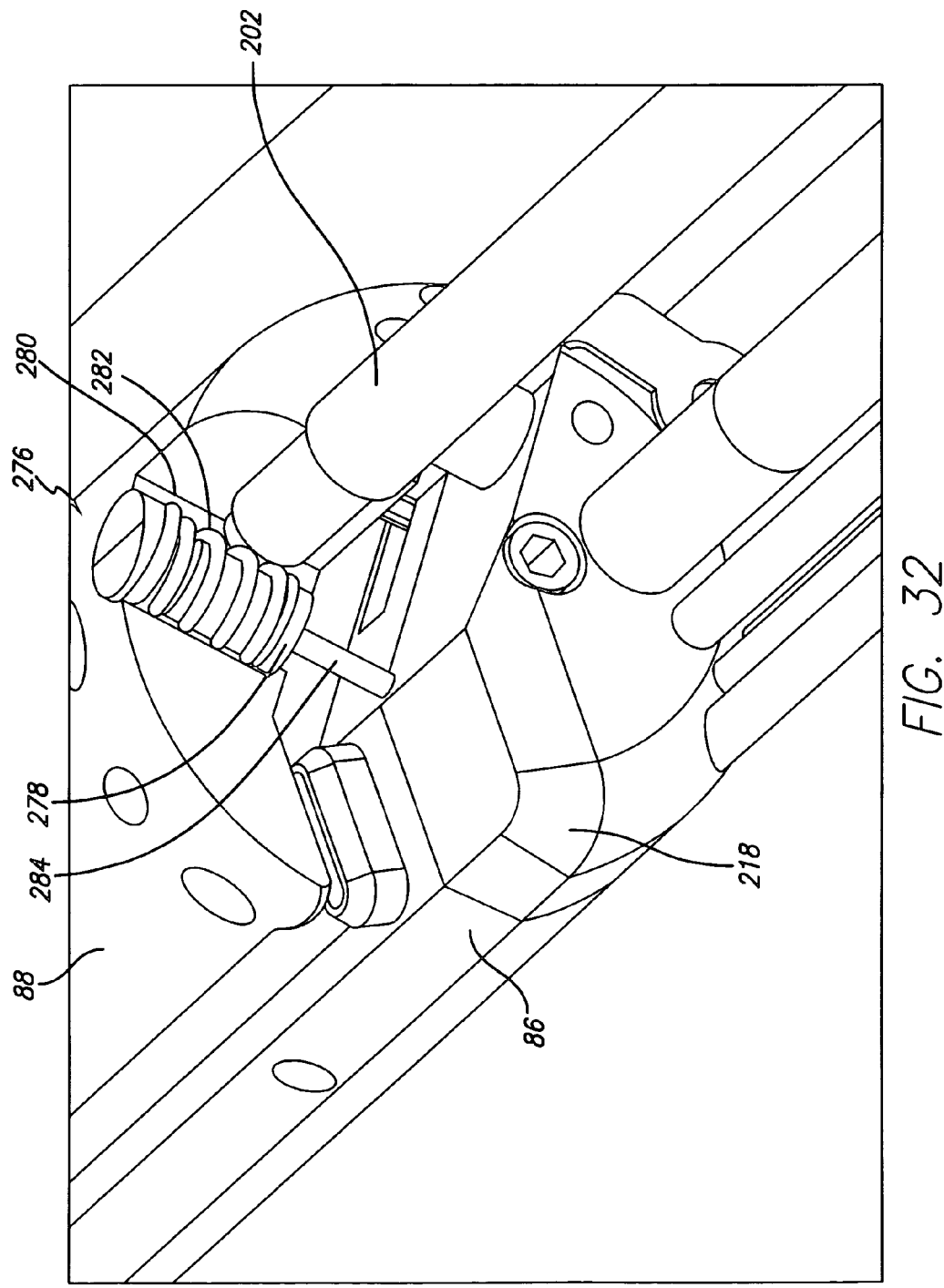

Referring now to FIGS. 31 and 32, a vacuum detection device 276 is shown attached to the proximal end of the tissue treatment device 52. The vacuum detection device includes a valve 278 positioned within a pocket 280 formed within the anvil member 88. The valve is biased open by a spring 282 that engages the valve within the pocket. A piston 284 attached to the valve extends out of the pocket and comes into contact with the proximal end cap 218 attached to the proximal end of the cartridge member 86 when the device is closed. The pocket is placed in the anvil member so that the valve intersects the vacuum line provided by the anvil vacuum tube 202 that supplies a vacuum to an anvil chamber 286 within the anvil member. During use, the vacuum created at the chamber and through the anvil opening 104 is measured at the handle assembly 60. When the jaws 86 and 88 are close to being completely closed as shown in FIG. 32, the piston comes in contact with the cartridge member, which in turn compresses the spring and the valve begins to open. The more the valve opens, the bigger the drop in the vacuum supplied by the anvil vacuum tube. The valve can provide about 5 inch of mercury drop when the jaws are fully closed. This drop in vacuum can be measured at the proximal end where the vacuum is created. When the vacuum begins to drop from the valve opening, tissue has already been acquired and is being clamped between the jaws, therefore, vacuum is no longer necessary to hold the tissue within the jaws. In another embodiment, a second valve can be placed on the distal end of the anvil member and/or be connected with the vacuum chamber of the cartridge member 86.

Figure 33:
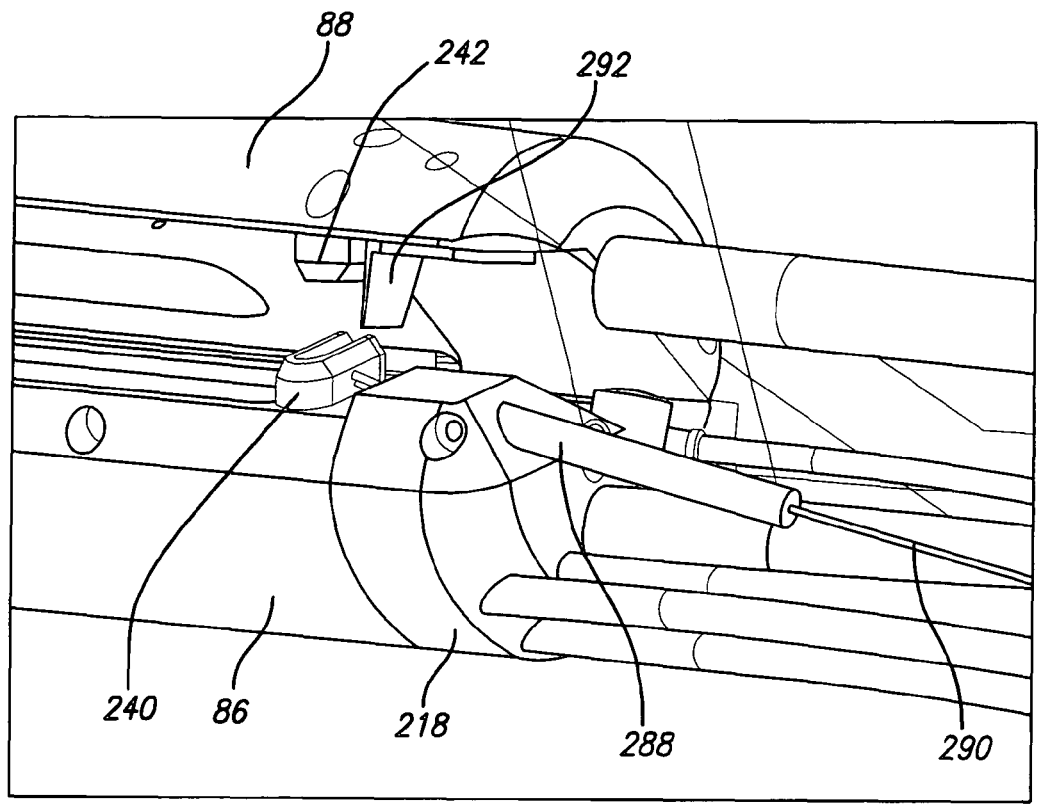
FIGS. 33 through 35 show the proximal end of the tissue treatment device having a fiber optic sensor for detecting closure of the jaws.
Figure 34:
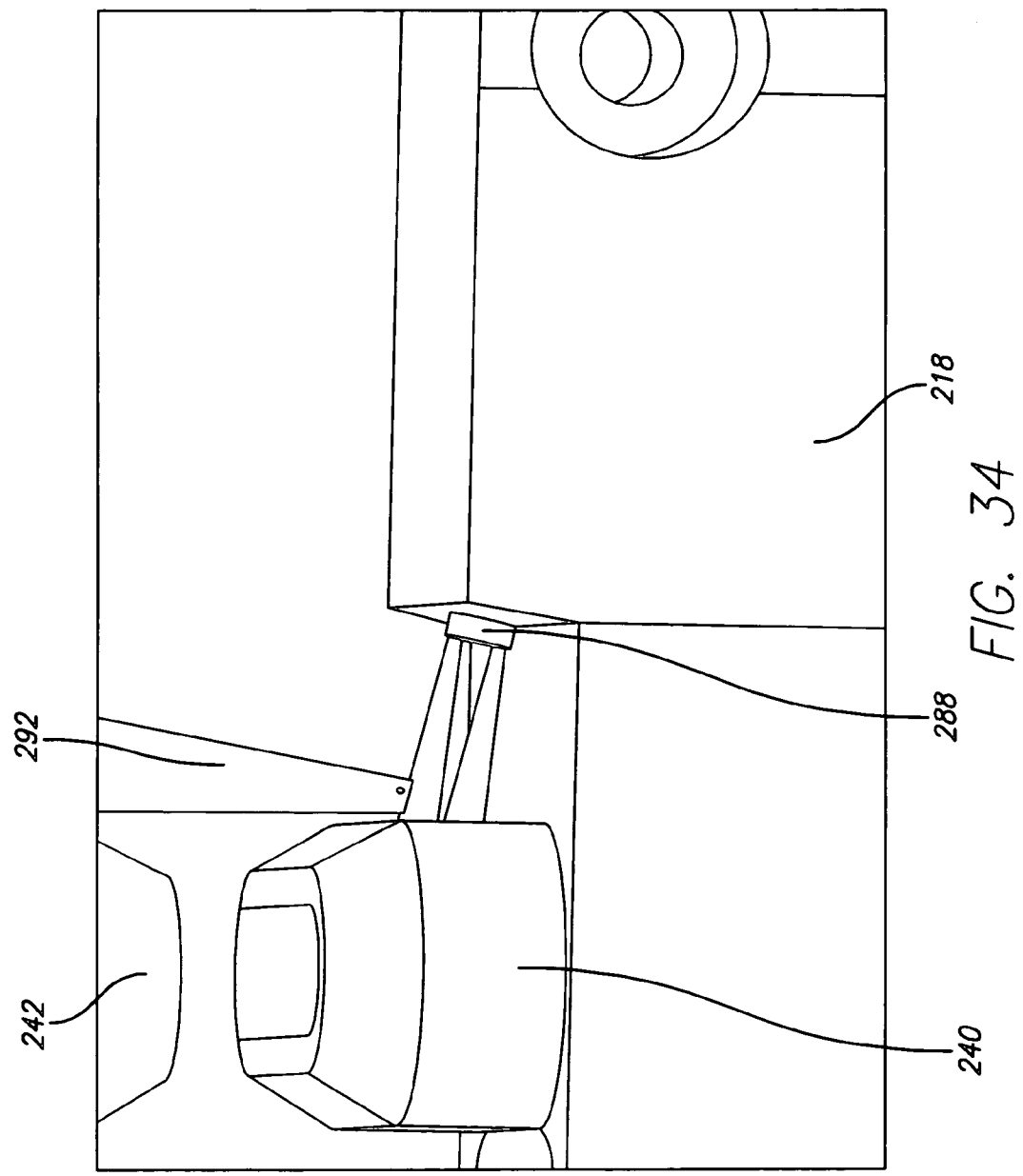
Figure 35:
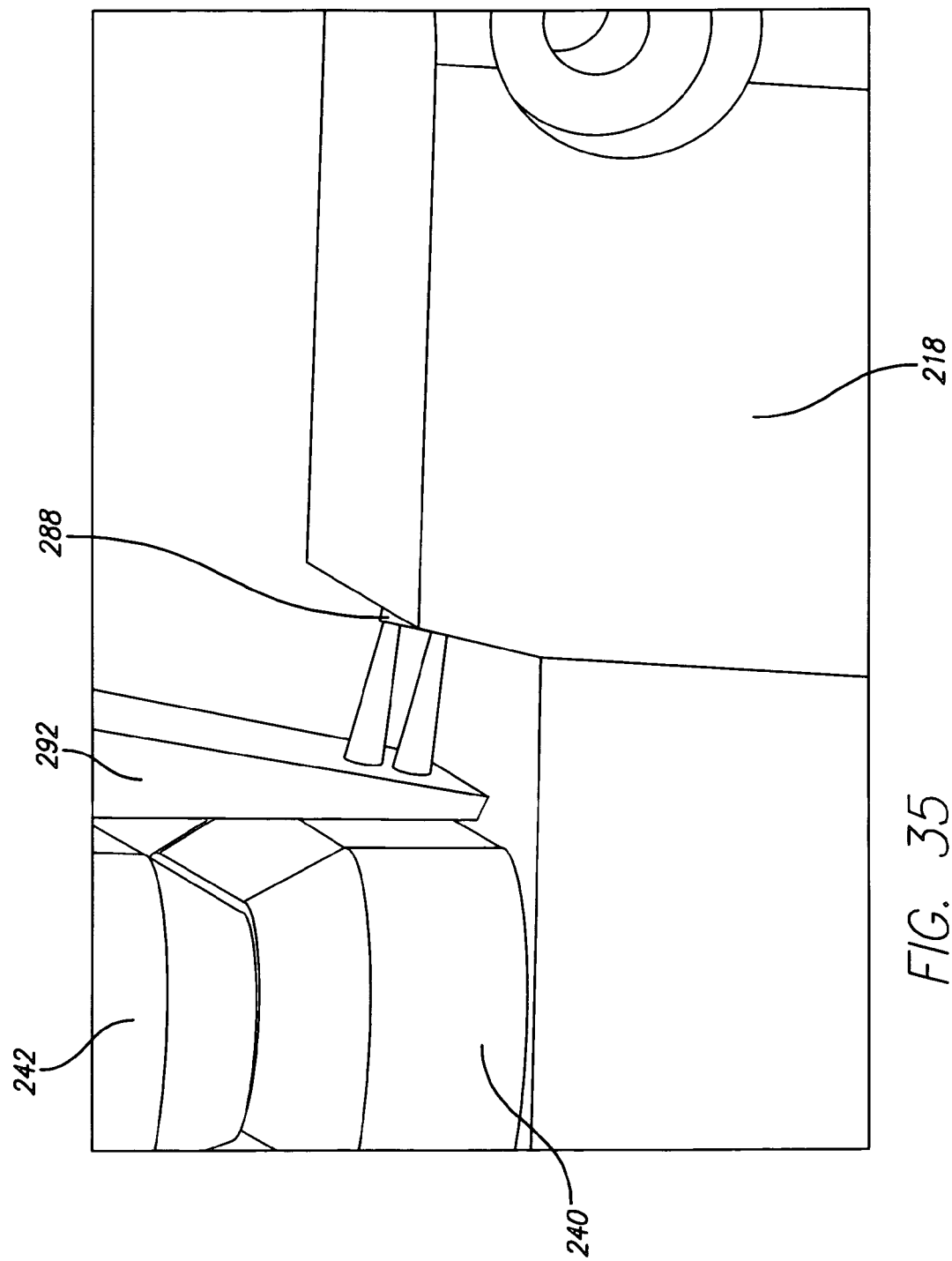

In another embodiment shown in FIG. 33 through 35, a fiber optic sensor 288 is mounted to the proximal end cap 218 and is directed towards the cartridge stop 240 located on the cartridge member 88. An optic fiber 290 runs from the tissue treatment device 62, through the elongated member 52, and to the handle assembly 60. When jaws 86 and 88 are open as shown in FIGS. 33 and 34, light emitted from the sensor is generally dispersed with a negligible amount of light being reflected off of the surface of the cartridge stop. A reflective material such as a mirror 292 is mounted on the anvil member as shown, so that when the jaws are about 0.035 inch apart (see FIG. 34), the mirror begins to intersect the optical path of the emitted light and reflects the a portion of the light. At this point, the distance between the mirror and the sensor in this embodiment is about 0.43 inch. When the jaws are fully closed as shown in FIG. 35, the distance between the mirror and the sensor is about 0.039 inch, a difference of more than 10% and producing a more than 20% difference in the projected optical path, which is enough to create a drop of about 50% in a photon counting electronic counter placed outside the device at the handle assembly. This reading taken at the handle assembly indicates to the user that the jaws are closed. In another embodiment, the optical sensor can be placed at the distal end of the tissue treatment device, or a second optical sensor can be placed at the distal end of the device.

Figure 36:
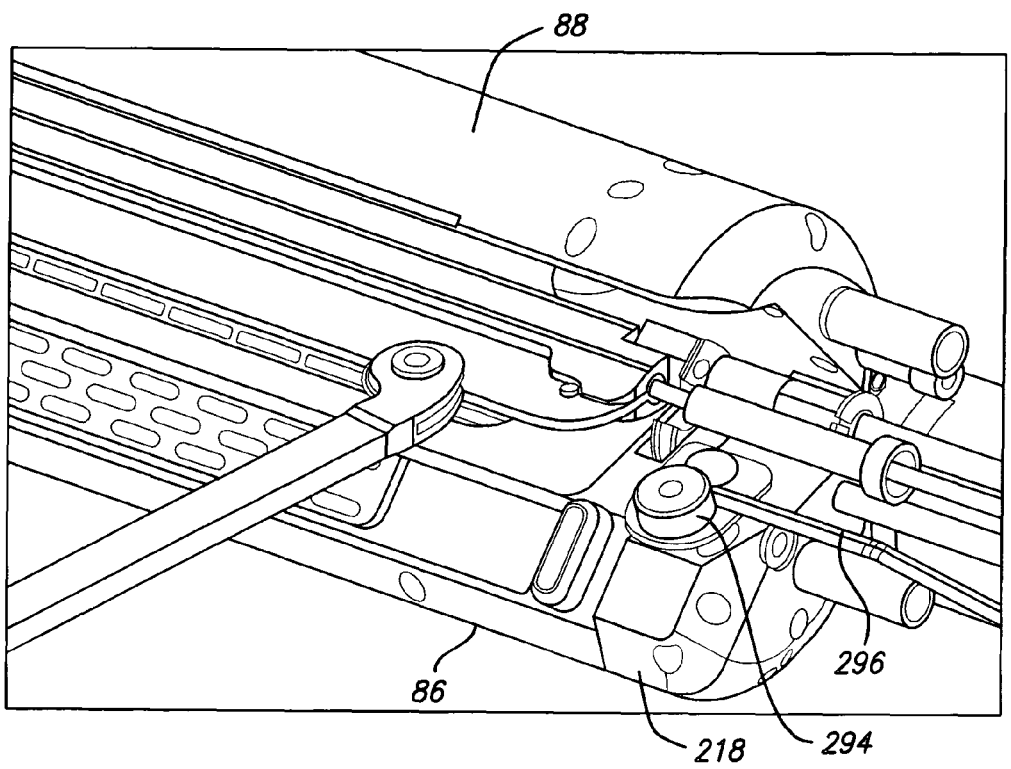
FIG. 36 shows the proximal end of the tissue treatment device having a proximity sensor for detecting closure of the jaws.

A proximity sensor 294 can also be used to detect closure of the jaws 86 and 88 as shown in FIG. 36. In this embodiment, the proximity sensor is mounted to the cartridge member 86 and detects the distance between itself and the proximal end of the anvil member 88. The sensor can be wired to work as a switch so that once the jaws are fully closed, the proximity sensor sends a signal along wires 296 back to the handle assembly 60 where an audio or visual output indicates that the jaws are closed. The sensor can also be wired to work as a distance measuring unit with a read out at the handle assembly to indicate when the jaws are fully closed. In another embodiment, the sensor can be programmed to trigger when the anvil reaches a certain distance from the sensor without any mechanical adjustments.

Figure 37:
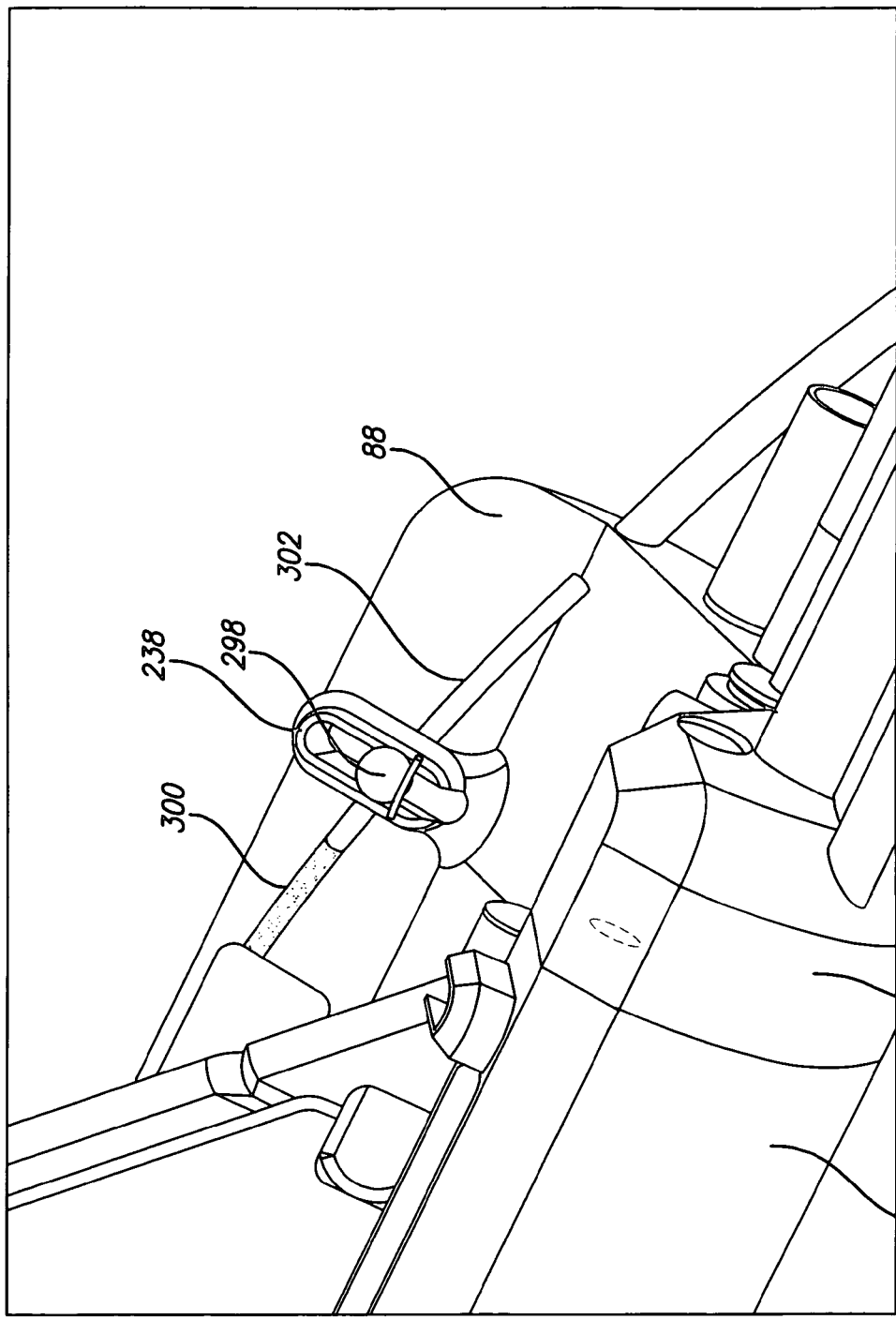
FIGS. 37 and 38 show the proximal end of the tissue treatment device having a mechanical clamp for detecting closure of the jaws.
Figure 38:
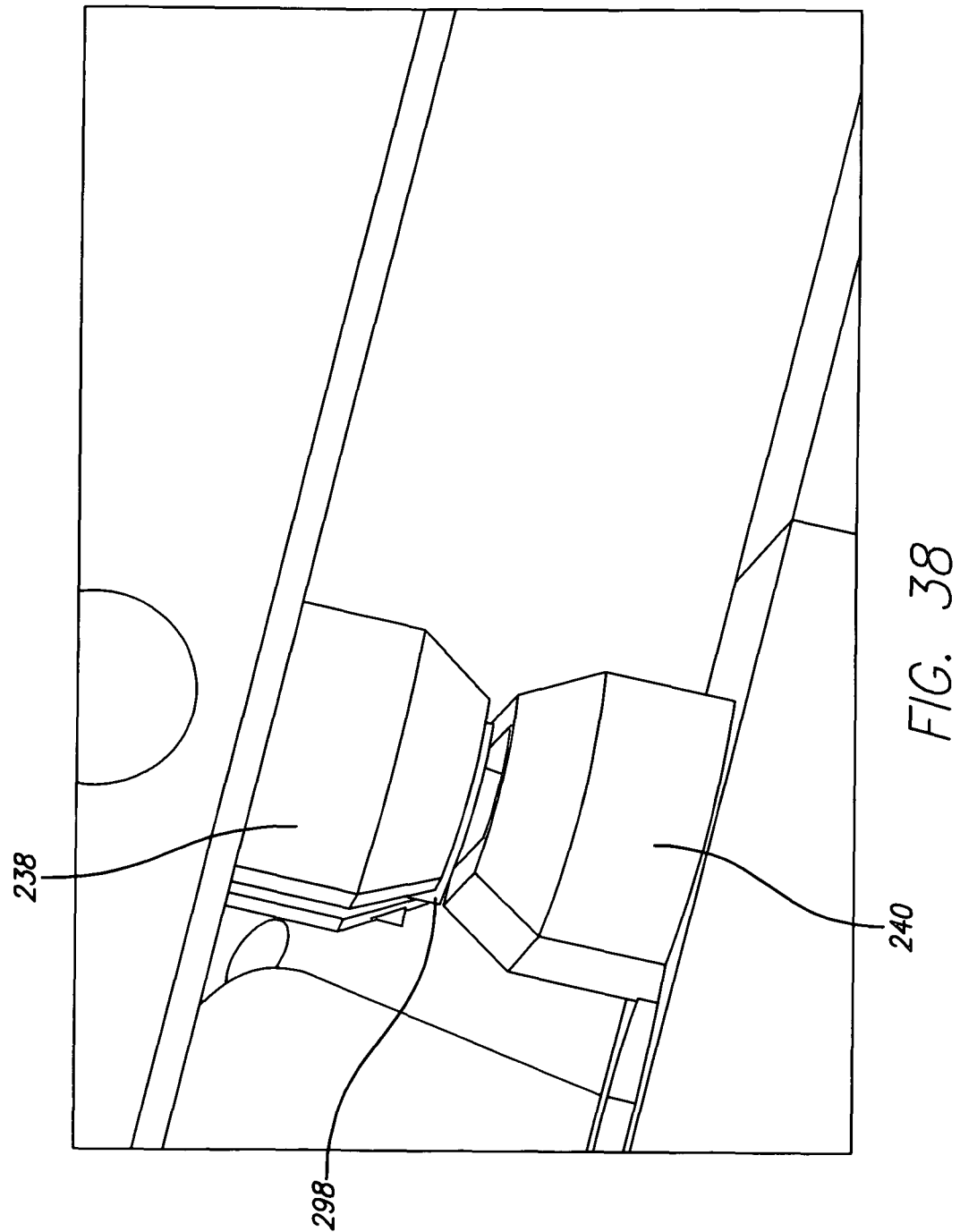

Referring now to FIGS. 37 and 38, a mechanical clamp 298 can be positioned within the anvil stop 238 and may be spring loaded to bias the clamp in an open position. A groove 300 is formed within the anvil member 88 and is sized such that a clamp wire 302 can be positioned within the groove with enough space to move or rotate. The groove and the clamp wire pass underneath the clamp, and when the clamp is in the open position because the jaws 86 and 88 of the tissue treatment device 62 are opened, the clamp wire, which runs along the elongate member 52 and out of the handle assembly 60, is free to rotate or be moved back and forth within the groove. When the jaws are fully closed as shown in FIG. 38, the cartridge stop 240 of the cartridge member 86 comes in contact with and pushes the mechanical clamp against the clamp wire in the groove. At this point, the user will notice an increase in resistance to rotate or move the clamp wire within the groove, indicating that the jaws are fully clamped.

Figure 39:
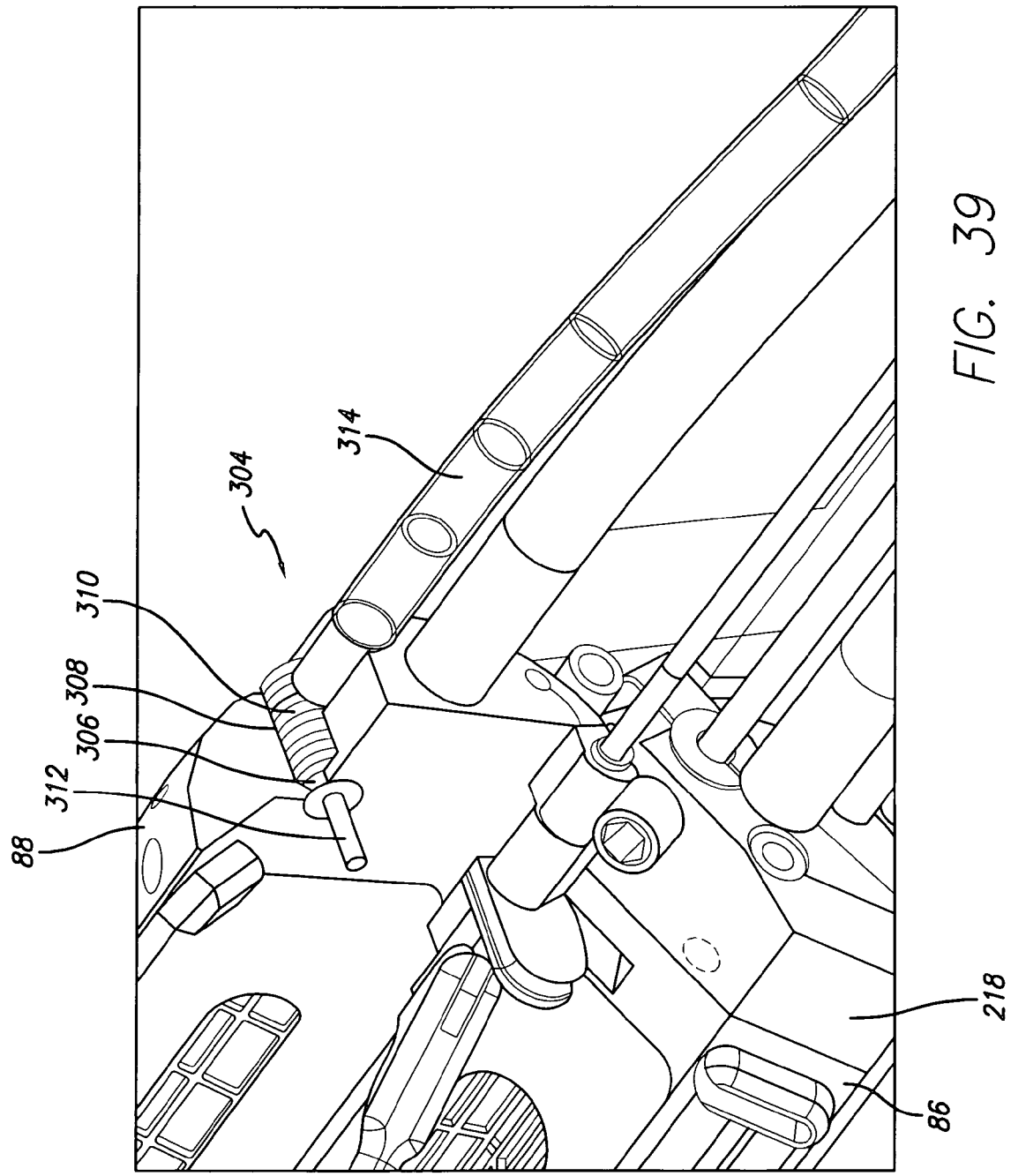
FIG. 39 shows a partial cross-sectional view of the proximal end of the tissue treatment device having a positive pressure device for detecting closure of the jaws.

In FIG. 39, a positive pressure device 304 is shown attached to the proximal end of the tissue treatment device 52. The positive pressure device includes a valve 306 positioned within a pocket 308 formed within the anvil member 88. The valve is biased open by a spring 310 that engages the valve within the pocket. A piston 312 attached to the valve extends out of the pocket and comes into contact with the proximal end cap 218 attached to the proximal end of the cartridge member 86 when the device is closed. There is also a separate fluid line 314 that is in communication with the pocket. During use, air or other fluid is supplied into the fluid line, and when the jaws 86 and 88 are close to being completely closed, the piston comes in contact with the cartridge member, which in turn compresses the spring and the valve begins to open. When the valve opens, the pressure drops, which can be detected at the handle assembly 60 by a pressure gauge that is in communication with the proximal end of the fluid line or at the source of the pressure.

Figure 40:
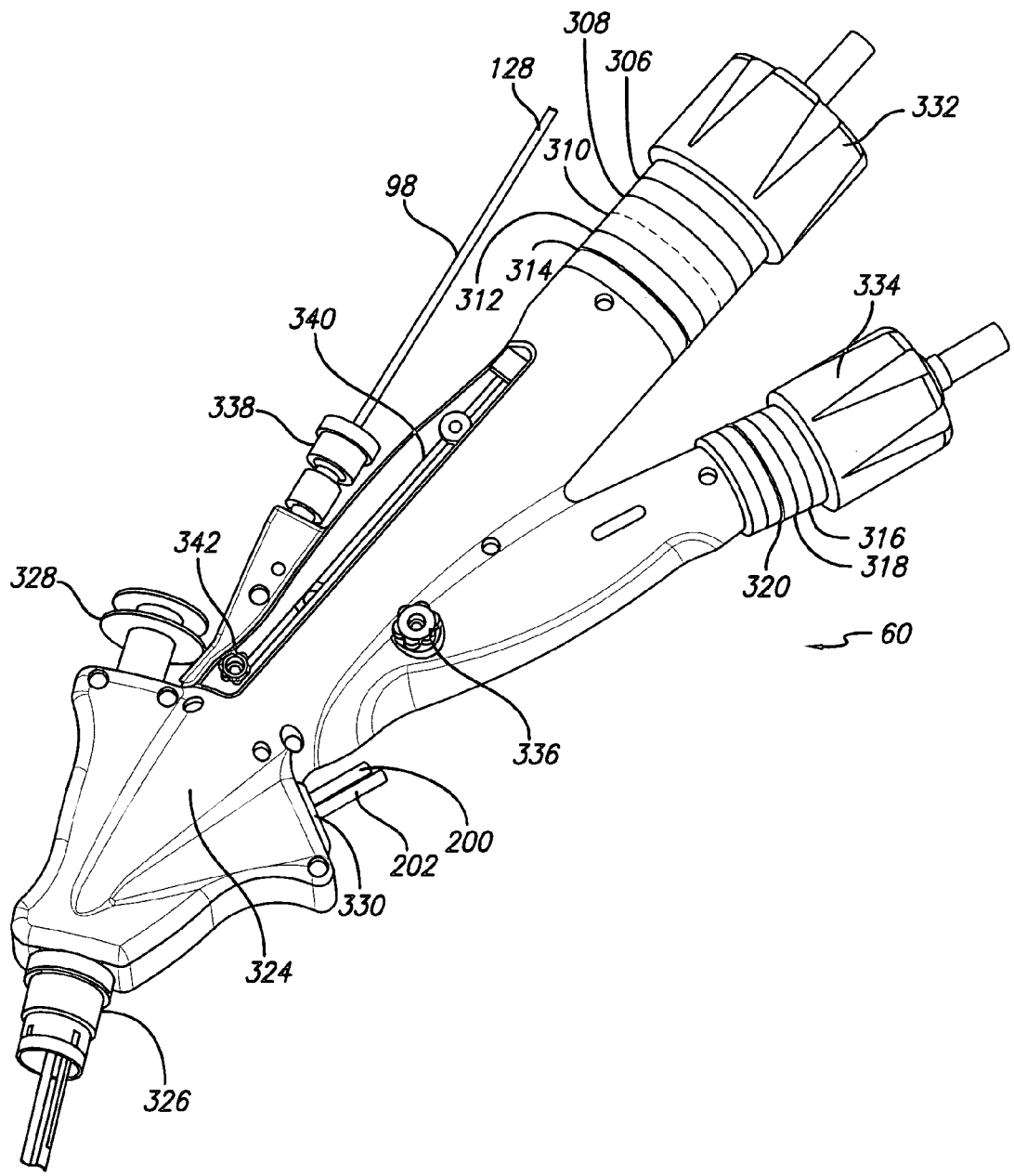
FIG. 40 shows a perspective view of a handle assembly.
Figure 41:
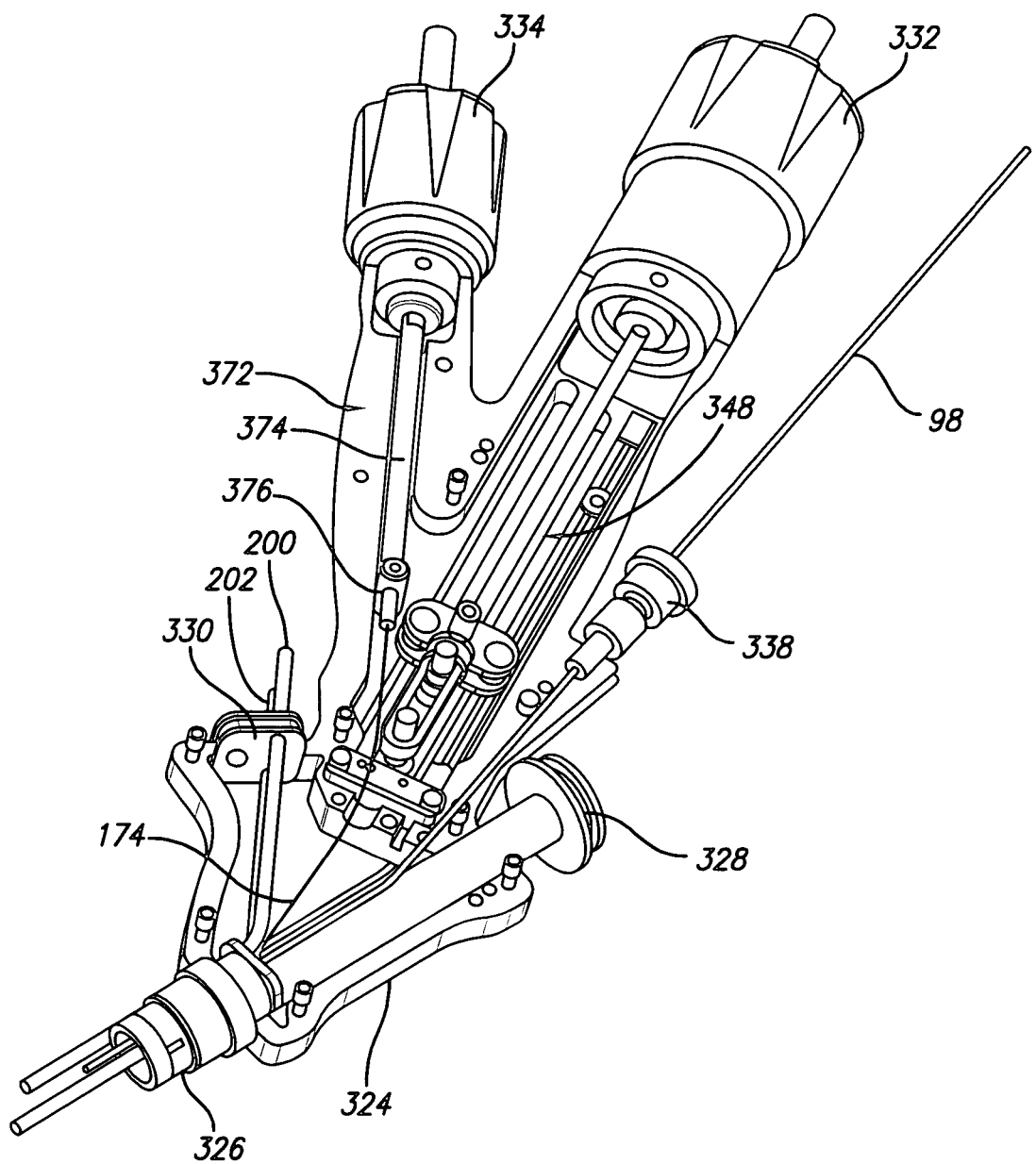
FIG. 41 shows a partial cross-sectional view of the handle assembly shown in FIG. 40.

Referring now to FIGS. 40 and 41, the handle assembly 60 will be discussed in detail. As shown in FIG. 40, the handle assembly includes a housing 324 having a transition knuckle 326 that attaches to the elongate tubular member 52. There is a scope tube and seal mount 328 which allows entry of an endoscope into the elongate member, and a vacuum tube adapter 330 which holds proximal ends of vacuum tubes 200, 202 and an insufflation tube (not shown) so that the tubes may be connected to a vacuum source. In one embodiment, the distal portion of the handle assembly including the transition knuckle, the scope tube and seal mount, and the vacuum tube adapter is sealed pressure tight. A clamp/open knob 332 is located at the proximal end of the handle assembly and is in connection with clamping and opening cables 204, 206, and 210. Twisting the clamp/open knob in a counter-clockwise direction opens the cartridge and anvil members 86 and 88 of the tissue treatment device 62, and twisting the clamp/open knob in a clockwise direction clamps the cartridge and anvil members of the tissue treatment device closed.

There is also a wedge fire knob 334 in this embodiment that is in connection with the staple actuation wire 174. Turning the wedge fire knob in a clockwise directions causes the wedge 172 to move proximally within the staple cartridge 148 to fire the staples 188. A wedge lock 336 is disposed on the housing 324 near the wedge fire knob and is used to lock the staple actuation wire in position to prevent the wedge from being moved prior to forming a staple line within the stomach. In other embodiments, the wedge fire knob may be replaced with a lever or other activation means to pull the wedge within the staple cartridge. The handle assembly 60 also includes a retractor seal 338 to allow entry of the retractor wire 98 into the elongate member 52 while maintaining the sealed portion of the handle. A proximal end of the retractor wire extends out of the retractor seal and the user may push or pull the retractor wire during the procedure to extend and retract the retractor wire within the stomach cavity. A groove 340 is also disposed on the housing to track a septum push-off knob 342 that may be tightened to secure the septum wire 116 attached to the septum 90. The septum push-off knob can be moved along the groove to push the septum wire distally, thereby moving the septum distally along the septum rail 108 when needed, as will be described below.

In one embodiment as shown in FIG. 40, there are markings, such as, colored bands and/or numbers disposed on the housing 324 of the handle assembly 60 adjacent the clamp/open knob 332 to indicate the force being applied at the tissue treatment device 712. A most proximal line or first line 306 adjacent the clamp/open knob symbolizes 40 pounds of force being applied to the opening cable 210. Therefore, when the bottom edge of the clamp/open knob is located at the first line, this is an indication that the jaws 86 and 88 of the tissue treatment device are open. A second line 308, distal to the first line represents neutral, meaning that there is no tension being applied to the opening cable or the clamping cables 204 and 206. Distally adjacent to the second line is a third line 310 that is dotted in this embodiment, and symbolized that approximately 50 pounds of force is being applied to the clamping cables for a light clamp. If the edge of the clamp/open knob is at a fourth line 312, then that is an indication that approximately 135 pounds of force is being applied to the clamping cables for a full clamp. The last or fifth line 314 is usually thicker than the other lines and is red in color to indicate danger because at this point there is approximately 150 pounds of force being applied to the clamping cables for an over clamp which is not desired because this force may exceed the strength of the cables.

Still referring to FIG. 40, there also are markings, such as, colored bands and/or numbers disposed on the housing 324 of the handle assembly 60 adjacent the wedge fire knob 334 to indicate the force being applied at the wedge 172 through staple actuation wire 174 that is connected to the wedge fire knob. A most proximal line or first line 316 adjacent the wedge fire knob represents neutral, meaning that there is no tension being applied to the actuation cable and. Therefore, when the bottom edge of the wedge fire knob is located at the first line or proximal to the first line, this is an indication that the wedge has not been moved within the staple cartridge 148. A second line 318, distal to the first line represents 25 pounds of force being applied to the staple actuation wire. This is enough force to break the shear pin, allowing the wedge to move the wedge proximally in the staple cartridge to begin firing staples. Distally adjacent to the second line is a third line 320 that is usually thicker than the previous two lines and is red to indicate danger, because this indicates that 60 pounds of force is being applied to the staple actuation wire, which may exceed its strength.

Figures 41A, 41B:
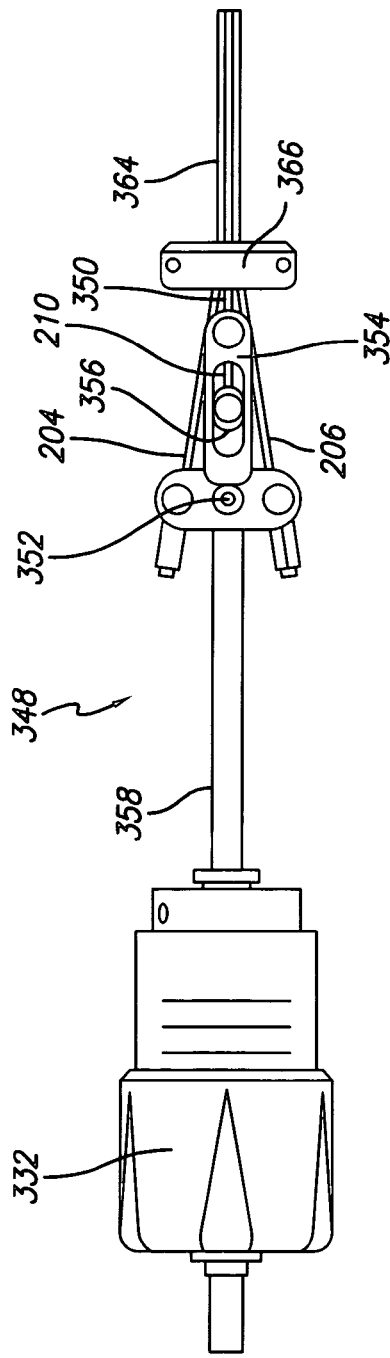
FIGS. 41A and 41B show a push/pull mechanism disposed within the handle assembly.

Referring now to FIGS. 41 through 41B, a push/pull mechanism 348 that is in connection with the clamp/open knob 332 and the cables 204, 206 and 210 will be described. FIG. 41A shows the push/pull mechanism in an opened configuration when the jaws 86 and 88 of the tissue treatment device 62 are opened. To open the jaws, the opening cable 210 is tensioned with respect to an open coil pipe 350. Tensioning is accomplished by turning knob 332 counterclockwise, which pushes a balance bar pivot 352 against a slide link 354. This action pushes a cross pin 356 distally, which moves the open coil pipe distally and has the effect of tensioning the opening cable 210. When the knob 332 is turned counterclockwise, a lead screw 358, which is fixed rotationally, translates with the balance bar pivot and is pushed distally. Once the balance bar pivot comes in contact with the slide link, an open thrust bearing 360 begins to compress open springs 362 in a spring holder 364.

FIG. 41B shows the push/pull mechanism 348 in a closed configuration when the jaws 86 and 88 of the tissue treatment device 62 are clamped together. To close or clamp the jaws, the outer and inner clamping cables 204, 206 are tensioned with respect to clamp coil pipes 364. Tensioning is accomplished by turning the knob 332 clockwise, which pulls the balance bar pivot 352 and the clamping cables proximally, and redirects the cables through guide block 366. When the knob 332 is turned clockwise, the lead screw 358 is pulled proximally to tension the clamping cables. Once the clamp cables begin to tension, a clamp thrust bearing 368 begins to compress clamp springs 370. Once the lead screw is pulled proximally so that the balance bar comes out of contact with the slide link(s), the tension on the open cables is released. Lead screws can have various thread pitches to create different clamp/open profiles. For example, constant thread pitch would cause the jaws to close at a consistent rate, but a varying pitch (along the lead screw) could generate sections of the travel to act quicker or slower, i.e. open fast, close slow, etc.

Referring back to FIG. 41, the wedge fire knob 334 is attached to a wedge fire mechanism 372 that is attached to the staple actuation wire 174. To fire the staples at the tissue treatment device 62, the knob 334 is turned clockwise to pull a lead screw 374 proximally into the knob. The lead screw is rotationally fixed, but it is free to translate. Attached to the lead screw is a wedge wire adaptor 376 that tensions the staple actuation wire and pulls the wedge 172 located within the staple cartridge 148 proximally. Before firing the staples, the wedge lock 336 should first be loosened and removed from a guide pin located between the lead screw and the wedge wire adaptor.

In one embodiment, the gastroplasty device 50 may be transorally delivered through the esophagus to create one or more plications within the stomach cavity. With reference to FIGS. 42-48A, one method of using the gastroplasy device will be described to form a sleeve or pouch within the stomach cavity and the gastroesophageal junction.

Figure 42:
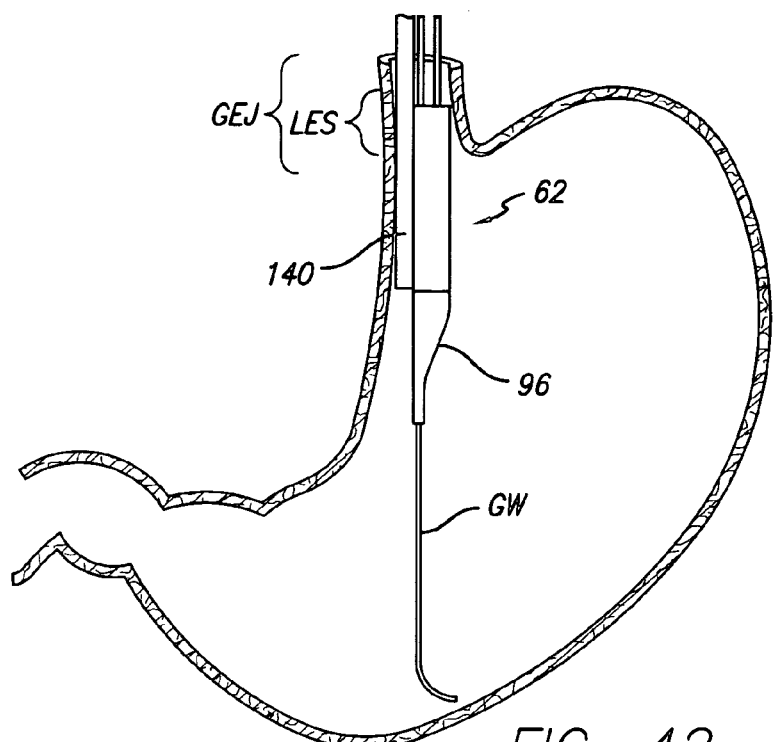
FIGS. 42 through 49 show illustrative views and cross-sectional views of one method of forming a gastric sleeve in a stomach cavity.
Figure 43:
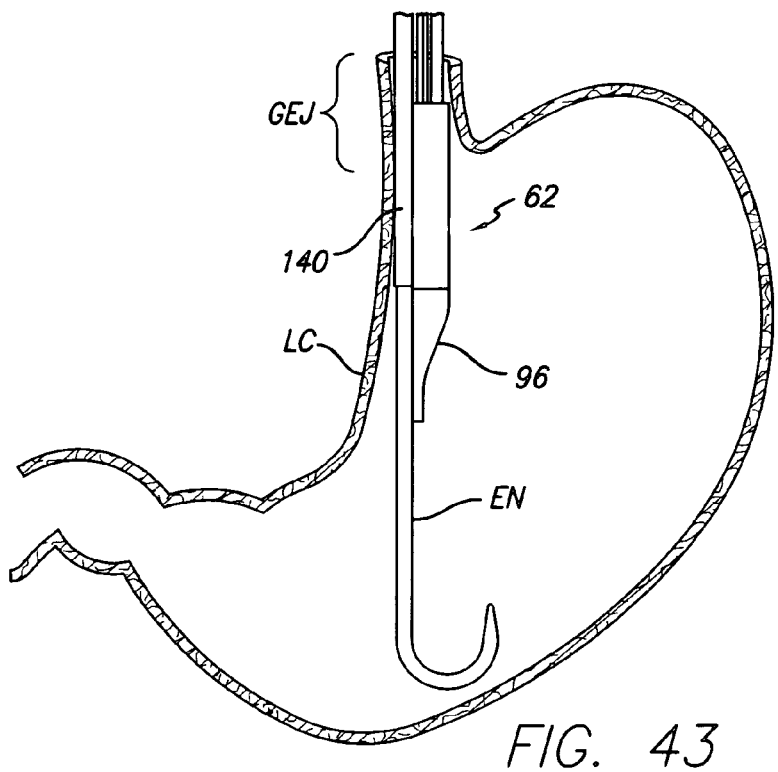

In one embodiment, an endoscope EN my be introduced transorally to the stomach cavity of the patient to inspect the upper gastrointestinal tract and the stomach cavity. During the procedure, the patient is placed in the supine position and a bite block is placed within the mouth of the patient for access to the patient's esophagus. During this initial inspection, it may be important to note the position of the Z-line. A guide wire GW may then be introduced through the endoscope to the stomach cavity and the endoscope may be removed from the patient. With the guide wire in position, a bougie dilator (not shown) is introduced over the guide wire to dilate the esophagus and the gastroesophageal junction ("GEJ"). The bougie dilator is removed and the proximal end of the guide wire is passed through the guide wire lumen 138 of the distal tip 96 and the tissue treatment device 62 is introduced through the esophagus and into the stomach cavity until the tissue treatment device is about 5 cm beyond the Z-line location as shown in FIG. 42. In one embodiment, there may be markings along the jaws 86 and 88 to properly position the tissue treatment device. Next, the guide wire GW is removed and the endoscope EN is inserted through the scope tube seal mount 328 of the handle assembly 60, the elongate member 52, and the shroud 140. As shown in FIG. 43, the endoscope EN exits the shroud and is retroflexed to view the tissue treatment device to verify that the proximal end of the jaws 86 and 88 are in the GEJ. In some embodiments, the stomach may be insufflated using the insufflation tube for easier viewing with the endoscope.

With the endoscope EN still in position to provide real-time viewing of the tissue treatment device 62, the jaws 86 and 88 are opened by rotating the clamp/open knob 332 counterclockwise until the knob approaches the first line 306. At this time the backside of the tissue treatment device, the side including the shroud 140, should be positioned against the lesser curve ("LC") of the stomach cavity and the septum 89 should be positioned away from the LC.

Figure 44:
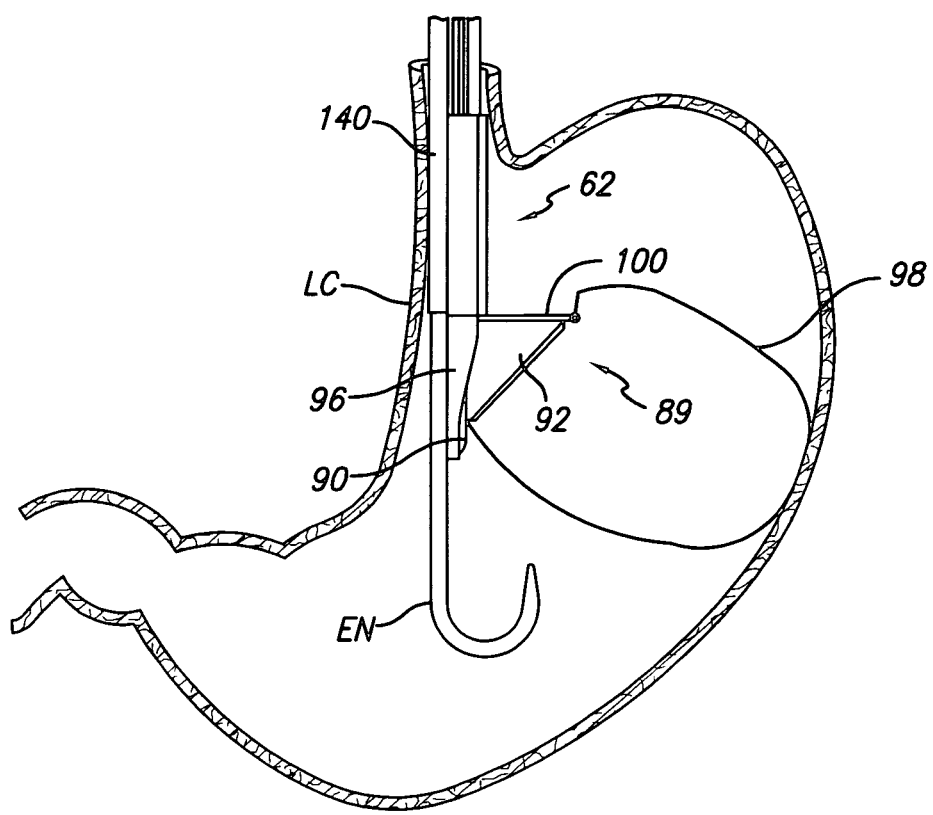

Next, the septum 89 is advanced distally until the stop 110 contacts the distal ridge 114 of the septum rail 108 and the retractor wire 98 and sail 92 are extended as shown in FIG. 44.

To advance the septum distally within the septum rail, the septum push-off knob 342 is unlocked by rotating it counter-clockwise, and then the knob is moved proximally along the groove 340 about 2 cm and is then tightened to capture the septum wire 116 and slide it distally within the groove, thereby pushing the septum wire distally at the tissue treatment device 62. This procedure can be repeated until the stop of the septum abuts the distal ridge of the septum rail. When the time comes to move the septum stop to the proximal ridge of the septum rail, this procedure is reversed. To advance the retractor wire 98 and deploy the sail 92, the retractor wire is advanced distally by pushing the proximal end 128 of the retractor wire through retractor seal 338 to retract the greater curvature ("GC") of the stomach with the excess loop of wire 130. Although not shown, a thumb screw may be attached to the proximal end of the retractor wire to more easily push the retractor wire distally. This action also deploys the sail 92 as shown in FIG. 44. The excess loop of wire can be positioned within the stomach by rotating the gastroplasty device 50 to achieve optimal tissue retraction.

The endoscope EN should then be positioned behind the tissue treatment device 62 to make sure the hinge line of the jaws 86 and 88 is close to the lesser curve LC, since excessive deployment of the retractor wire can possibly move the tissue treatment device away from the targeted tissue. If this unwanted movement does occur, then the retractor wire should be pulled back (proximally) until the tissue treatment device is positioned against the lesser curve LC. The axial position of the tissue treatment device should also be re-checked with the endoscope ensuring that the proximal portion of the vacuum pod openings 102 and 104 on the cartridge member 86 and anvil member 88 are buried in the lower esophageal sphincter ("LES"). Markings on the jaws of the tissue treatment device can be used to check this positioning.

Figure 45:
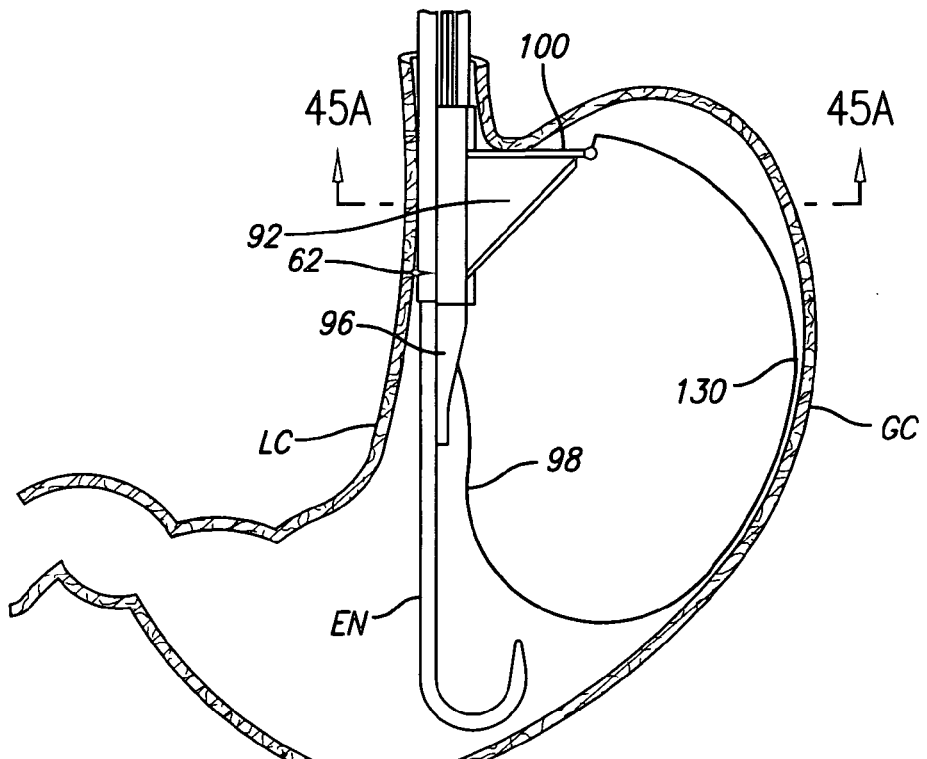
Figure 45A:
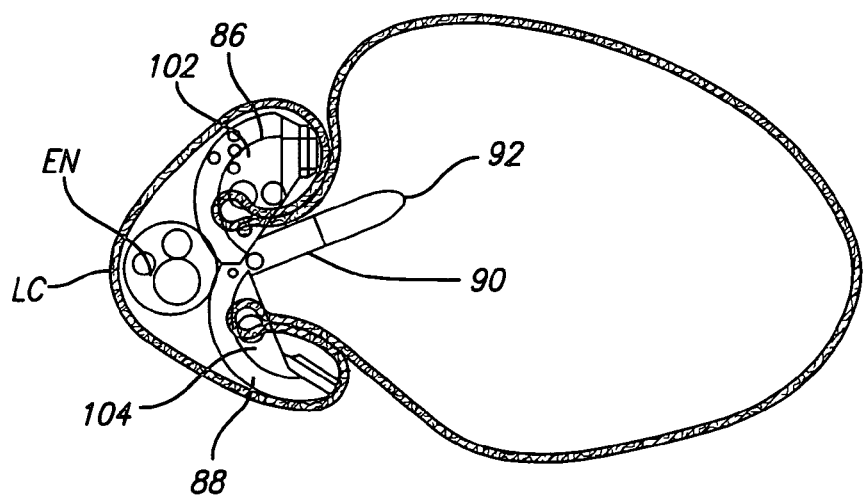

Once the physician is satisfied with the positioning of the tissue treatment device 62 within the stomach, the septum 89 is retracted or moved proximally along the septum rail 108 until the mast or sail arm 100 presses against the GEJ at the cardiac notch as shown in FIG. 45 to ensure that tissue of the GEJ is incorporated into the staple line, so that no unwanted communication exists between the newly created lumen or pouch, and the remnant stomach at the level of the GEJ. This movement is accomplished at the handle assembly 60 by pulling back (or moving proximally) on the septum knob. At this stage, the vacuum tubes 200 and 202 are clamped off and connected to a vacuum pump, which is then turned on. When the pump is stabilized at full vacuum, (between approximately 25 inHg-30 inHg, preferably 27 inhg-29.5 inhg), the stomach is slowly desufflated and the endoscope should be used to check that the tissue treatment device is close to the posterior lesser curve and that stomach tissue is presented optimally next to the openings 102 and 104 on the cartridge member and anvil member. The stomach is then completely desufflated and then the vacuum tubes 200 and 202 are opened to acquire tissue in each opening 102 and 104 of the cartridge and anvil members 86 and 88. In some embodiments, the vacuum tubes are opened simultaneously, however, the vacuum tubes may be opened at different times as well. The extended sail and retractor wire help organize the targeted tissue into the appropriate jaw and prevent the acquired tissue from crossing into both jaws of the tissue treatment device. FIG. 45A depicts a cross-sectional view taken along line 45A-45A of FIG. 45, with folds of tissue being acquired in the openings 102 and 104. After about one minute of acquiring tissue within the tissue treatment device, the septum 89 is advanced distally along the septum rail 108 until the septum stop 110 on base 90 contacts the distal ridge 114 of the septum rail using the method described above.

Figure 46:
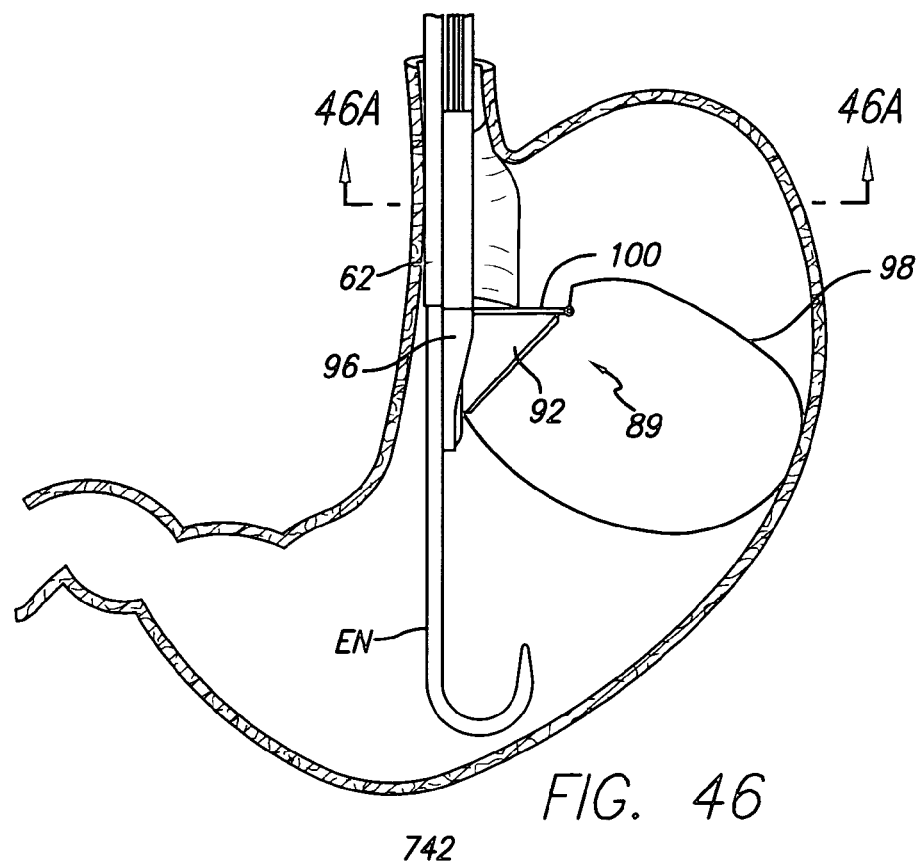
Figure 46A:
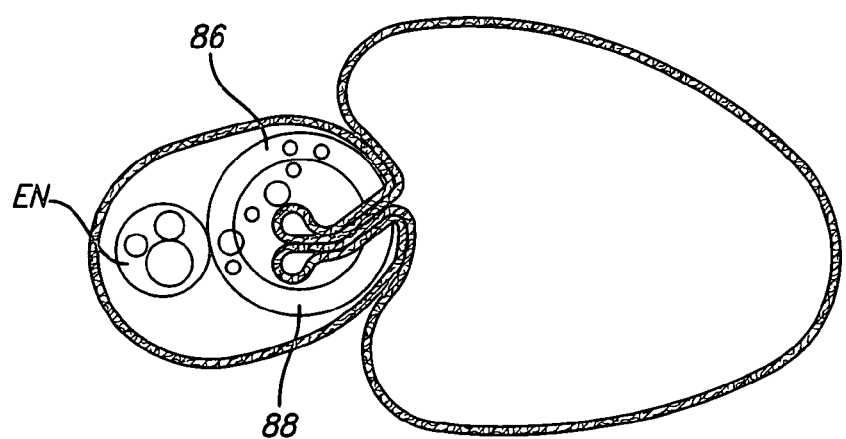

Referring to FIGS. 46 and 46A, with the septum 89 moved distally, the jaws 86 and 88 are lightly clamped together by rotating the clamp/open knob 332 in a clockwise direction until the knob completely covers the third line 310 on the handle assembly 60. It may be desired to insufflate the stomach once again to view the acquired tissue that is being held with the jaws of the tissue treatment device 62. When viewing the acquired tissue with the endoscope EN, the axial location of the tissue treatment device should also be rechecked as described above. It is desirable that the jaws have acquired tissue from both the GEJ, including a portion of the LES, and the stomach cavity. Acquiring tissue above the Z-line helps to ensure that no proximal stomas will be formed at the proximal end of the sleeve that is being created. The physician should also check to make sure that septum is fully advanced and away from the acquired tissue. It is desirable that the acquired tissue have no large folds or pleats so that a smooth double sleeve can be formed with the device.

Figure 47:
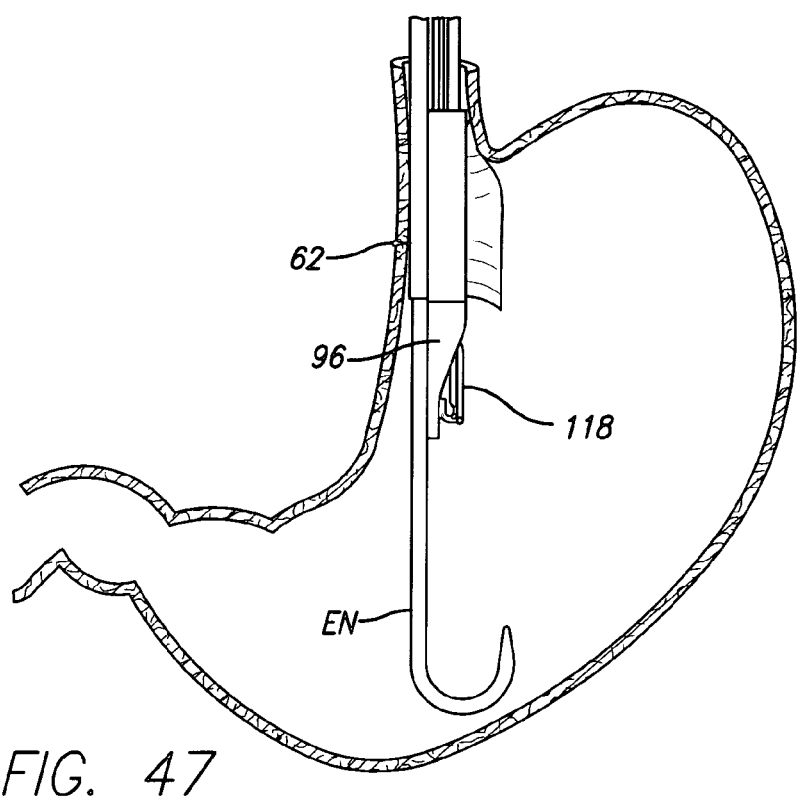

If the acquired tissue and septum position are acceptable, the retractor wire 98 is pulled proximally at the handle assembly 60 while holding the septum wire 116 in place to collapse the retractor wire and sail 92 as shown in FIG. 47. The stomach may then be desufflated once again and the vacuum tubes 200 and 202 may be unclamped to re-apply vacuum that holds the tissue within the openings of the members 86 and 88 of the tissue treatment device 62. After desufflation, the jaws 86 and 88 of the tissue treatment device are fully clamped together by rotating the clamp/open knob 332 in a clockwise direction until the knob covers the fourth line 312 on the handle assembly. The folds are now ready to be plicated, so in one embodiment, the wedge lock 336 on the side of the handle assembly is removed to allow the wedge fire knob to move the wedge and fire the staples. With tissue clamped between the members of the tissue treatment device, the dual folds of the tissue are stapled together by rotating the wedge fire knob 334 clockwise, which moves the wedge 172 proximally within the staple cartridge 148 to fire the rows of staples into the acquired tissue. FIG. 46A depicts a cross-sectional view taken along line 46A-46A of FIG. 46, and shows the two folds of tissue being stapled together with the tissue treatment device.

Figure 48:
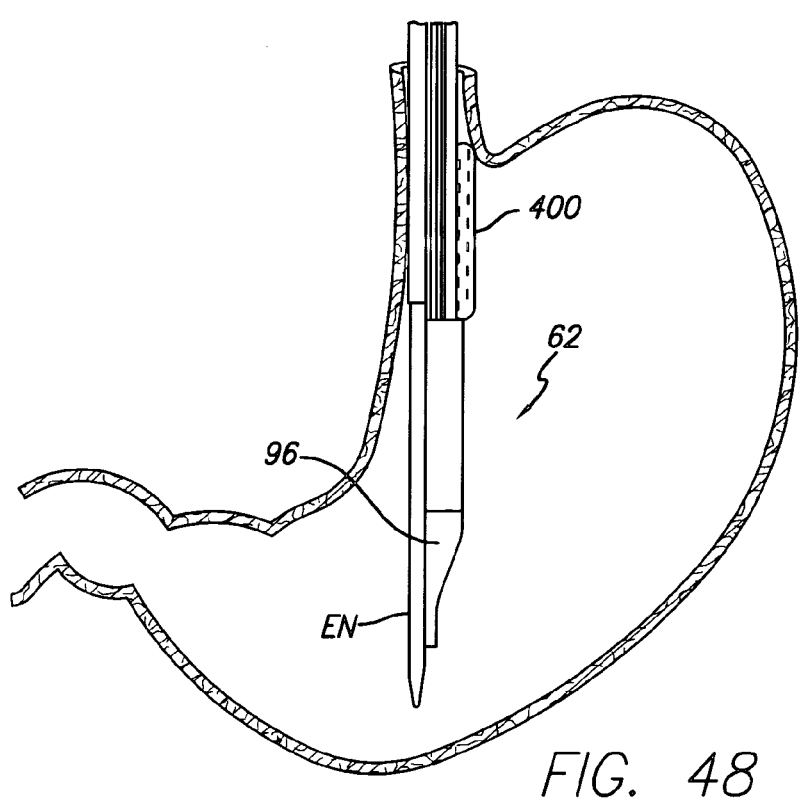
Figure 49:
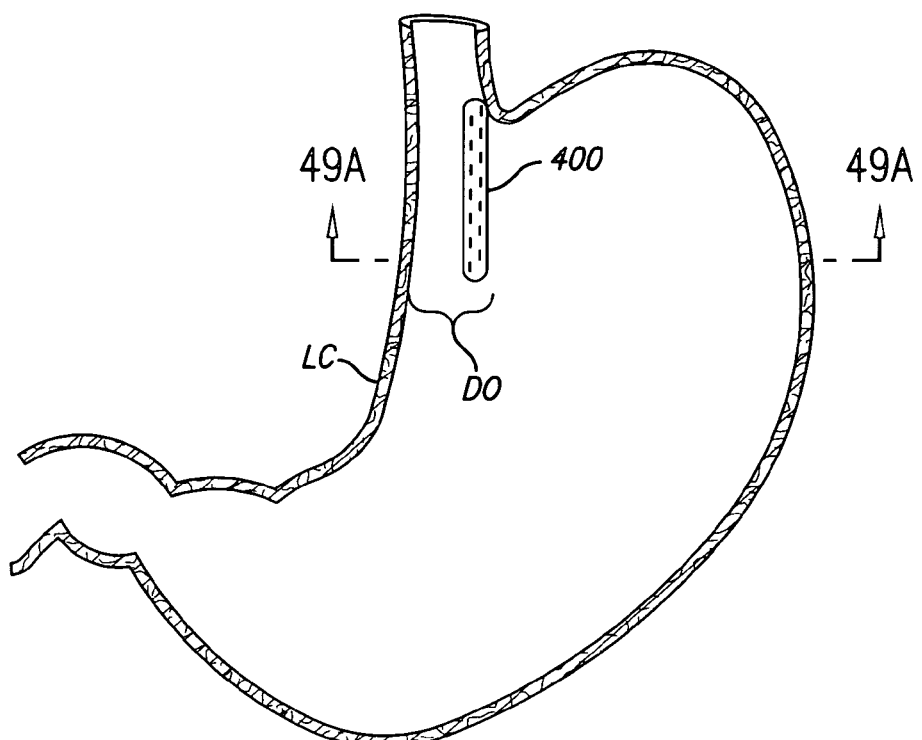
Figure 49A:
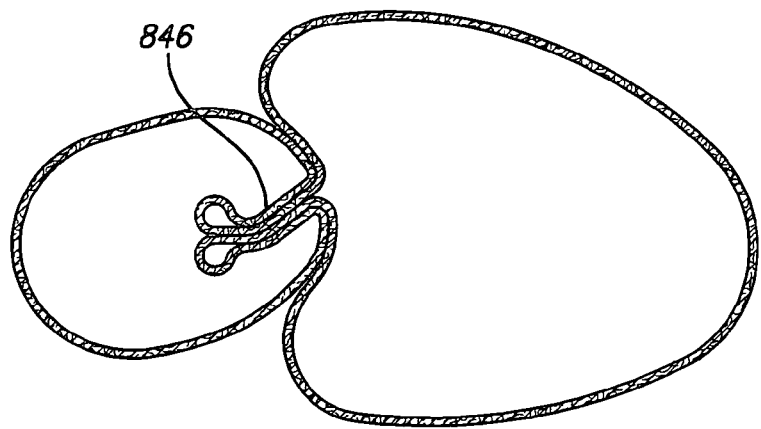

Once completed, the jaws of the tissue treatment device 62 are opened by rotating the clamp/open knob counterclockwise beyond the second line 308, and the vacuum pump connected to tubes 200 and 202 is turned off. In one embodiment, the jaws are not opened fully to prevent stretching the newly formed staple line in the stomach. Then, to remove the acquired tissue from the tissue treatment device, the acquired tissue may be flushed from the openings 102 and 104 of the members 86 and 88 with a sterile water bolus delivered via vacuum tubes with a syringe. The openings of the members may be flushed individually or simultaneously. The tissue treatment device may then be rotated and pushed back and forth until visual verification of pod-tissue disengagement can be made. As shown in FIG. 48, the device is advanced out of the distal end of the newly formed sleeve, and the septum wire 116 and retractor wire 98 are both pulled proximally from the handle assembly to move the septum 89 proximally along the septum rail 208 until the stop 110 of the base 90 contacts the proximal ridge 112 of the septum rail. The jaws of the tissue treatment device are then closed around the retracted septum and sail. The distal tip of the device can be visually inspected to ensure that the septum is clamped within the jaws, and then the endoscope EN is straightened as shown in FIG. 48. The endoscope is removed from the gastroplasty device 50, and then the entire device is removed from the stomach cavity, leaving a sleeve 400 within the stomach as shown in FIGS. 49 and 49A. The endoscope may be re-introduced to visualize the stapled sleeve. By acquiring tissue from the GEJ, the sleeve extends from the GEJ down into the body of the stomach, which may include extending towards the region of the pylorus. It is often desirable that tissue from the LES, in the vicinity of the Z-line, is incorporated in the sleeve. Beginning the staple line that forms the sleeve in the GEJ helps to minimize any communication between the remaining stomach and the newly formed sleeve or pouch. Therefore, no unwanted stomas or gaps should exist at the proximal end of the staple line.

If a long sleeve, two or more sleeves or staple lines, is to be disposed within the stomach cavity, the removable staple cartridge 148 can be replaced with a fresh staple cartridge, as described above, and the entire procedure can be repeated to form another sleeve acting as though the distal end of the first sleeve 400 were the GEJ. It is desirable that gaps or stomas are minimized between individual staple lines that form a long sleeve, and in one embodiment the staple lines of a long sleeve may be overlapped (end to end) to minimize gaps between staple lines. When forming a second staple line, it is preferred that the septum 89 be oriented to fit between the stapled folds of tissue of the first sleeve, or as close as possible. In one embodiment, the sail arm 100 of the septum is translated along the tissue treatment device to its proximal position such that it abuts the distal end of the first staple line. Placing the tissue treatment device in this position ensures that the tissue near the distal end of the first staple line will be acquired by the proximal end of the tissue treatment device and incorporated into the newly formed second staple line. This provides one continuous staple line with no unwanted stoma formed between the first and second staple line. In another embodiment, translating the sail arm of the septum such that it is just distal to its proximal position on the septum rail and then abutting the distal end of the first staple line with the staple arm allows the tissue treatment device to gather at least a portion of the first staple line to overlap the two staple lines. This helps to ensure that no unwanted stomas are formed. Translating the sail arm of the septum a greater distance distally along the sail rail before acquiring tissue allows for a greater portion of the first staple line to be acquired by the tissue treatment device when it is aligned such that the translated sail arm is pressed against the distal end of the first staple line.

Also, it is possible to reload the tissue treatment device 62 of the gastroplasty device 50 and then turn the tissue treatment device towards the lesser curve of the stomach to form a dual fold staple line down the lesser curve of the stomach. This procedure will narrow the sleeve formed by the two dual fold staple lines. In yet another embodiment, the tissue treatment device can be used to form a single fold staple line within the stomach cavity. In this embodiment, after forming a dual fold staple line, the tissue treatment device may be turned toward the lesser curve of the stomach to form another staple line. However, in this embodiment, a vacuum is only created in one of the vacuum openings 102 or 104 so that only one fold of tissue is acquired and then stapled to form a single fold staple line. This single fold staple line may be used to further restrict the sleeve formed by the initial dual fold staple line.

After forming plications within the stomach cavity using the gastroplasty device 50, a restrictor stapler 900 can then be used to perform a secondary step in a gastric sleeve or pouch formation procedure. The restrictor stapler may be similar to the endoscopic stapler described in U.S. patent application Ser. No. 11/107,382, which is incorporated by reference in its entirety. There are multiple uses for the restrictor stapler, such as forming additional plications in the distal end of a gastric sleeve, and in some situations to close a stoma or fistula created by a gastric sleeve.

Figure 50:
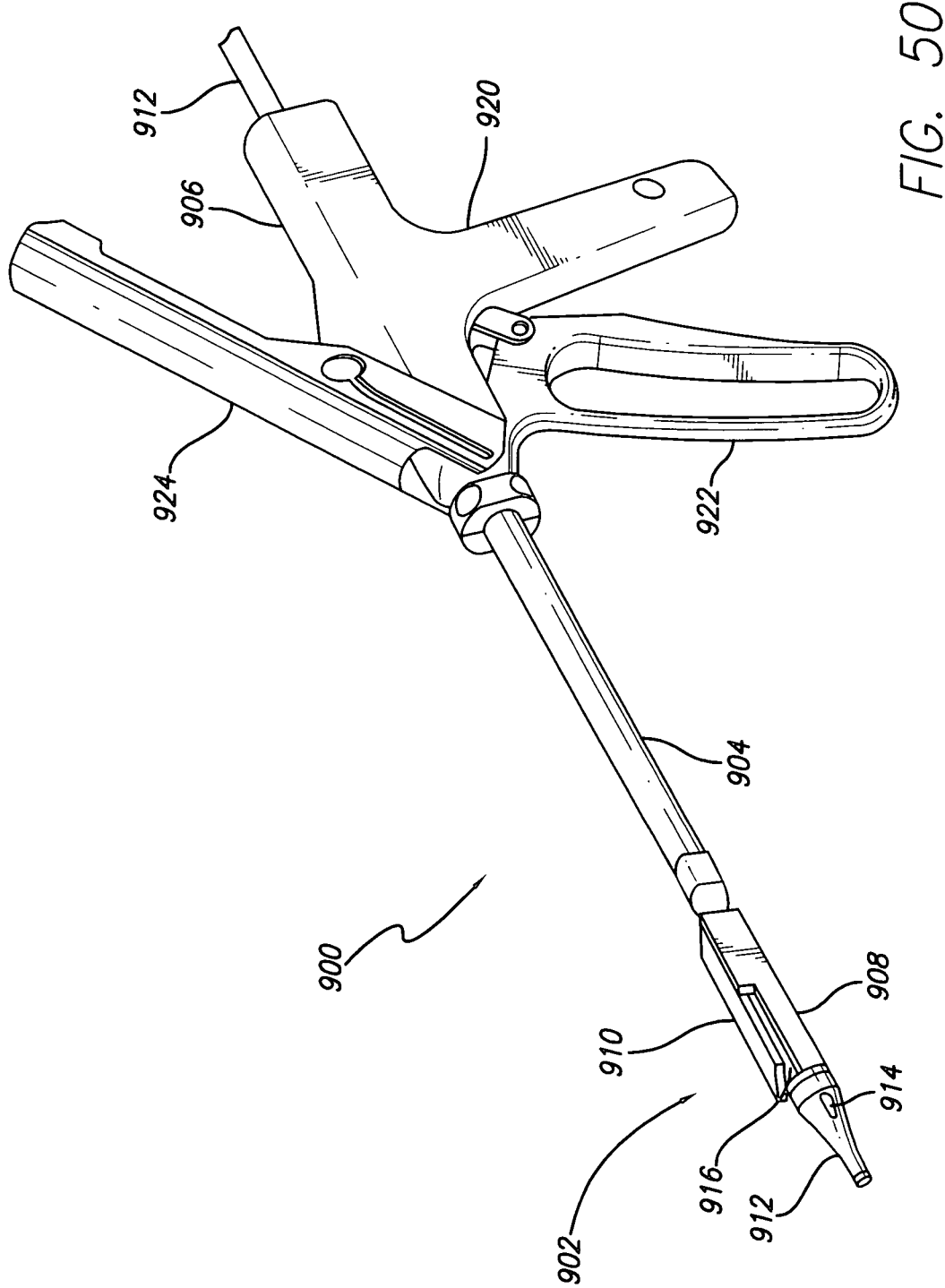
FIG. 50 shows a perspective view of a variation of a stapler restrictor.

Referring to FIG. 50, the restrictor stapler 900 includes a stapler assembly 902 or cartridge assembly connected via a flexible shaft 904 or elongated body having a proximal end and a distal end to a stapler handle 906. The stapler assembly includes a fixation member having a staple cartridge member 908, within which one or more staples are housed, and an anvil 910 in apposition to stapler cartridge member used to provide a staple closure surface when tissue to be affixed is adequately positioned between staple cartridge member and anvil. An optional smooth rubber tip 912 with a guide wire channel 914 may be attached to the distal end of the staple cartridge member. The atraumatic tip 912 prevents injury to tissue when the device is advanced down the esophagus, and the guide wire channel allows the fixation assembly to track down a guide wire. The staple assembly also includes an acquisition member for acquiring tissue. In one embodiment a vacuum pod 916 is attached or integrated into the staple cartridge member 908, and a vacuum line or tubing 917 extends from the vacuum pod, along the shaft 904 and to the handle 906. It is desirable that the overall insertion diameter of the stapler assembly and flexible shaft plus endoscope is equal to or less than 54 Fr. In one embodiment, with the jaws 908, 910 closed, the maximum perimeter of the device is equivalent to about 15.1 mm diameter (0.595 inch or 45 Fr diameter). With the jaws 908, 910 opened, the maximum perimeter of the device is equivalent to about 17 mm diameter (0.668 inch or 51 Fr diameter).

With stapler assembly 902 connected at the distal end of flexible shaft 904, the handle 906 is connected at the proximal end of shaft. The flexible shaft is configured to be curved, and in one embodiment can achieve a 4 inch bend radius with a low application of force. The handle 906 may include a housing and grip 920 in apposition to an actuation handle 922. In use, the handle 906 allows the surgeon or user to hold and manipulate the restrictor stapler 900 with grip 920 while articulating stapler assembly 902 between an open and close configuration via the actuation handle 922. A lever or staple deployment actuator 924 is also disposed on the handle 906 and is used to deploy staples from the stapler assembly 902. Moreover, the configuration of the handle 906 allows the surgeon or user to articulate the stapler assembly 902.

In one embodiment, the anvil 910 may be pivotally connected via a pivot 926 to the end of flexible shaft 904 as shown in FIG. 50A. The staple cartridge member 908 may be configured to remain stationary relative to the flexible shaft 904 while anvil 910 may be manipulated into an open and closed configuration with respect to flexible shaft and staple cartridge member. However, in another embodiment, the staple cartridge member may be pivotally connected to the flexible shaft and the anvil remains stationary. In yet another embodiment, both the anvil and the staple cartridge member can pivot into an open and closed configuration relative to the flexible shaft. The goal of this parallel jaw opening to minimize stretch of the sleeve to provide an even plication. To manipulate the anvil 910 to an open and closed configuration, a circular or disk-shaped cam may be pivotally attached about rotational pivot located on the side of the proximal end of stapler assembly 902, as described with reference to FIG. 31 in U.S. patent application Ser. No. 11/107382. Actuation wires or cables may be wound about cam such that when cable is pulled, cam is urged to rotate clock-wise about rotational pivot. Actuation cables may be manipulated from their proximal ends by the user. As cam is rotated in a clock-wise direction, a portion of staple cartridge member 908 may be engaged by the cam thereby forcing the anvil 910 to pivot into an open configuration. An additional cam may also be affixed on the opposite side of stapler assembly 902 such that dual cams are configured to open and close simultaneously in parallel. As shown in FIG. 50B, when dual cams are used and the jaws 908, 910 are opened, the surfaces of the jaws 908, 910 remain parallel to one another. This allows for better tissue acquisition between the jaws 908, 910.

In one embodiment as shown in FIG. 50C, the anvil 910 includes an anvil extension 928 disposed at the distal end of the anvil. The anvil extension contacts the ceiling of a pocket 930 disposed in the proximal end of the rubber tip 912 as shown in FIG. 50D. This keeps the distal end of the anvil in plane and forces the stapler cartridge 908 and anvil 910 to open in parallel as shown in FIG. 50B. Referring to FIG. 50C, the staple cartridge member 908 includes a cartridge extension 932 that engages a cutout 934 (see FIG. 50E) located at the proximal end of the rubber 912 to secure the rubber tip to the stapler assembly 902.

In one embodiment of the restrictor stapler 900, there are two rows of staple apertures 936 defined over the surface of the staple cartridge member 908, as best shown in FIG. 50D. Staples are deployed through the apertures in a similar manner as described with reference to FIGS. 22A to 23C of U.S. patent application Ser. No. 11/107,382, by pulling a staple actuation wire that in turn moves a wedge in contact with a staple pusher to fire a staple. In this embodiment, the lever or staple deployment actuator 924 is depressed to pull the actuation wire in order to fire the staples from the stapler assembly. The jaws 908, 910 of the stapler assembly 902 are closed, as shown in FIG. 50A, using the actuation handle 922, and then the staples may be deployed into the acquired tissue. Other variations may utilize fewer or greater than two rows of staple apertures.

In one embodiment of the restrictor stapler 900, the staple cartridge member 908 can be re-loaded with a removable staple cartridge 938. As shown in FIG. 50E, the removable staple cartridge may be integrated with the rubber tip 912, so that they are loaded and unloaded from the staple cartridge member 908 together. The removable staple cartridge 938 includes a detent pin 940 located near its distal end, that when placed into the staple cartridge member 908, locks into a lock hole 942 located near the distal end of the staple cartridge member. To load the removable staple cartridge 938 into the restrictor stapler 900, the jaws 908,910 of the stapler assembly 902 are opened, and the lever or staple deployment actuator 924 is raised to push a staple firing wedge to the distal end of the device. If the wedge does not travel to the end of the device, the wedge may be manually pulled using forceps. In one embodiment, firing cable struts can be disengaged from the lever and the lever can be lowered without moving the wedge from the distal location. The proximal end of the removable staple cartridge 938 may be inserted into the staple cartridge member 908 and slid back, ensuring wedge does not pre-fire the staples. Once the removable staple cartridge 938 is about 90% in place, the jaws of the stapler assembly are slowly closed to allow the anvil extension 928 to nest in the pocket 930 of the rubber tip. The removable staple cartridge 938 is then pushed down and back to ensure it is completely in the staple cartridge member 908, and the jaws 908, 910 are completely closed. As the rubber tip/removable staple cartridge are loaded onto the stapler assembly 902, cartridge extension 932 will engage the cutout 934 of the rubber tip 912 and the anvil extension 928 will fit into the pocket 930 of the rubber tip, and the detent pin 940 will snap into the lock hole 942. To unload or remove the rubber tip/removable staple cartridge, the jaws are opened and the detent pin 940 is pushed away from the lock hole 942 and the rubber tip/removable staple cartridge is removed by the user. The removable staple cartridges 938 may include two rows of six staples, each having 4.8 mm leg length with 3 mm backspan. The staple line length in this embodiment is about 25.0 mm (0.984 inch), although the length of the staple line may range from about 12.5 mm (0.492 inch) to about 50.0 mm (1.97 inch).

Figure 51:
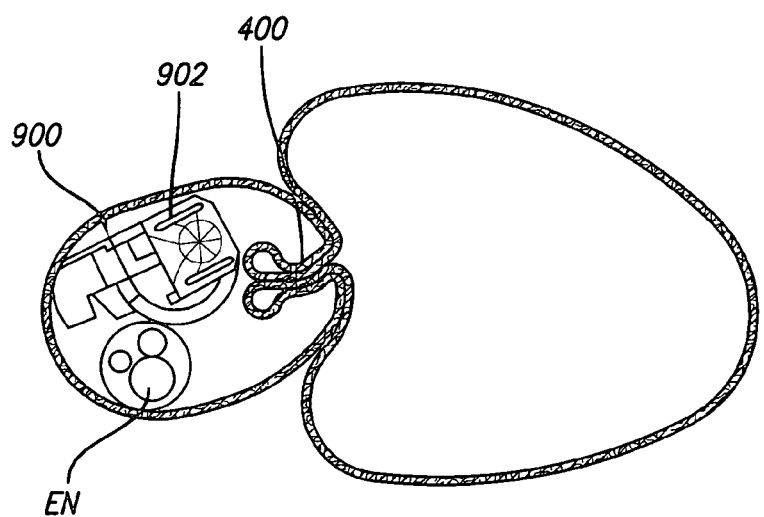
FIGS. 51 through 53A show cross-sectional views of one method of forming a single fold of tissue near a distal stoma of a gastric sleeve to narrow the distal stoma.
Figure 52:
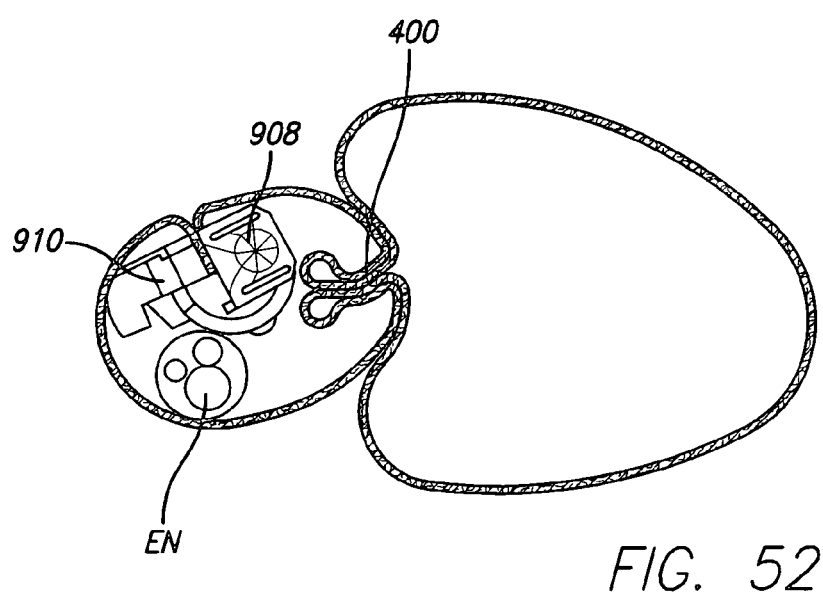
Figure 53:
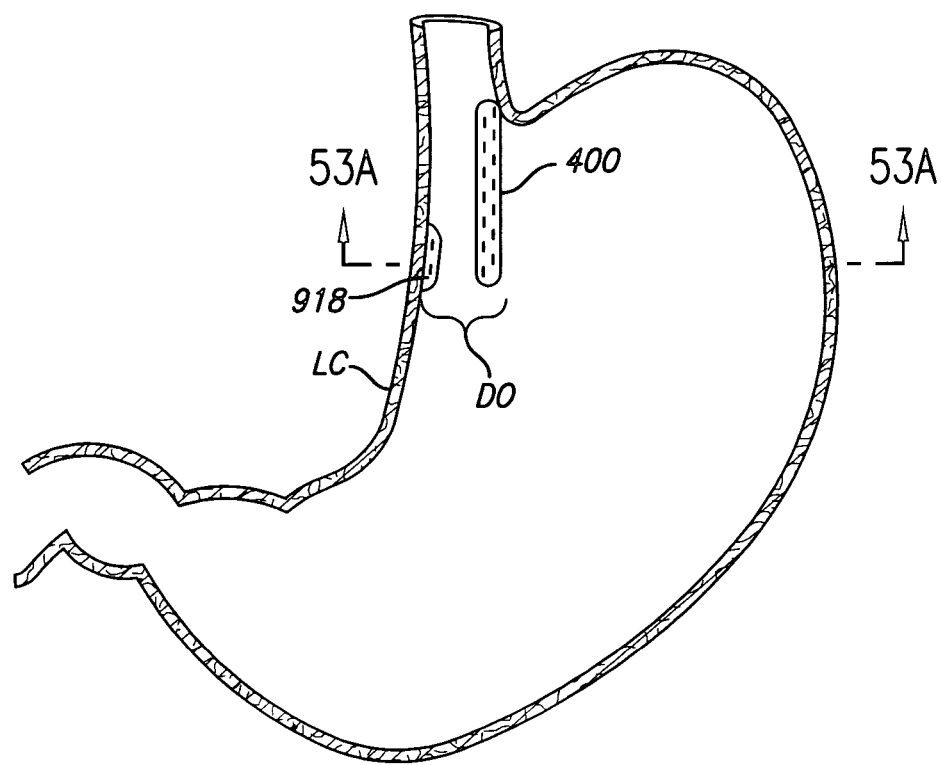
Figure 53A:
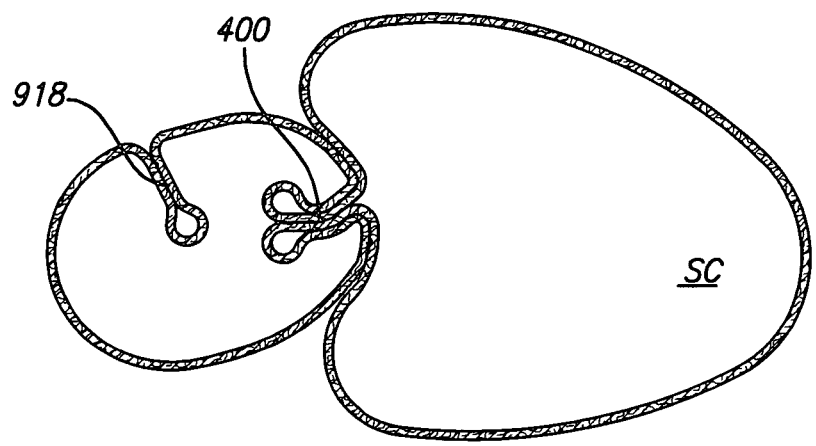
Figure 54:
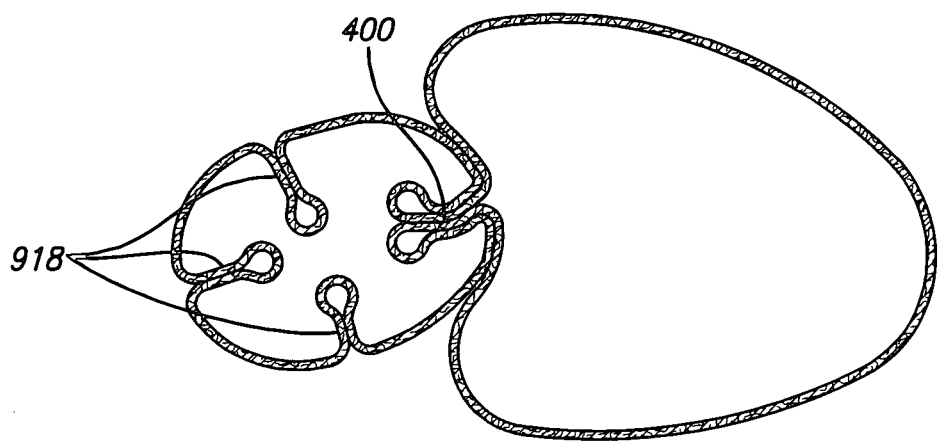
FIG. 54 shows a cross-sectional view of a gastric sleeve formed with one dual fold plication and restricted with three single fold plications.
Figure 57:
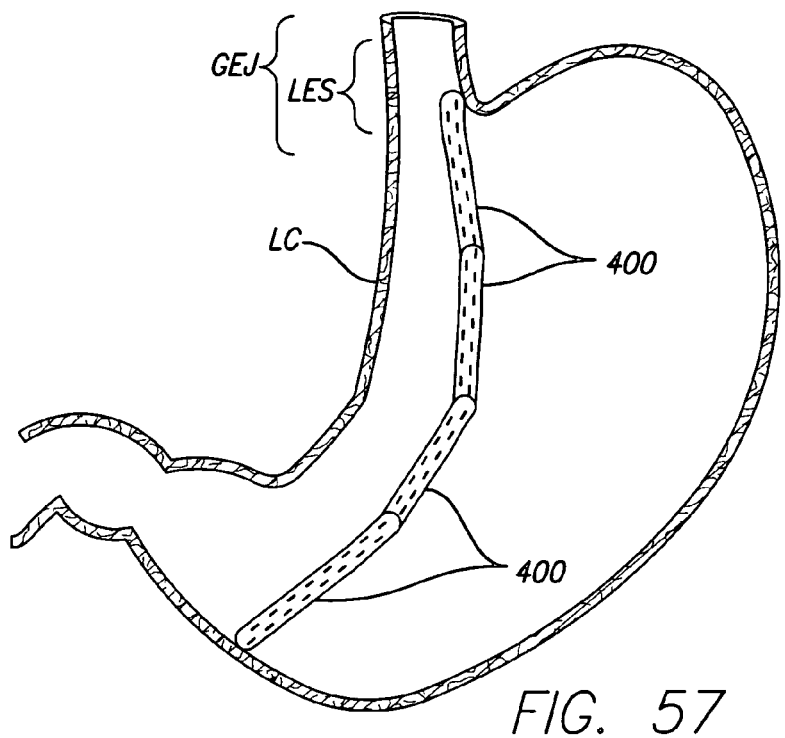
FIG. 57 shows an illustration of a stomach cavity with four dual fold plications forming a long sleeve from the gastroesophageal junction to the pylorus.

Generally, as shown in FIG. 51 the restrictor stapler 900 is advanced over a guide wire through the guide wire channel 914 of the rubber tip 912 and down the esophagus to the stomach cavity, the stapler assembly 902 is preferably in a closed configuration. Further, the restrictor stapler may be compatible with the side-by-side insertion of a 8.6 mm diameter flexible endoscope EN or similar scope. The device will be axially located by referencing external markings on the shaft of the device, or visually by using markings on the head of the stapler assembly 902 relative to the distal end of the stapled sleeve. In terms of radial location, the device will be rotated and placed while under direct visualization. Alternatively, the user may rely on markings on the handle to rotationally orient the device. Once the stapler assembly 902 is in the desired position within the stomach cavity for placing a plication along the stomach wall, the guide wire is removed, and the stapler assembly may be articulated into an open configuration as shown in FIG. 50B. A vacuum may then be created at the vacuum pod 916 to acquire a fold of tissue 918 between the staple cartridge member 908 and the anvil 910. It is desirable that a vacuum device be used to achieve a vacuum level of about 27 inHg to about 29.5 inHg. After the vacuum level has stabilized, the jaws of the stapler assembly 902 are then clamped closed over the tissue as shown in FIG. 52. The vacuum created at the vacuum pod 916 is shut-off, and the stomach cavity is insufflated to inspect and verify that the restrictor stapler is in the desired position relative to the distal end of the sleeve. If the position is acceptable, the endoscope may be straightened and removed. The stomach cavity is desufflated and vacuum is again created at the vacuum pod. The jaws of the stapler assembly 902 are then fully opened to complete the tissue acquisition and then held until the vacuum stabilizes. Once stabilized, the jaws of the stapler assembly are then clamped closed over the tissue. In some embodiments, the user waits fifteen seconds and then the staples are deployed into the acquired tissue to form a single fold plication. Vacuum is then released and the stapler assembly 902 is opened and the device is slightly advanced and rotated to allow for the gastric tissue to pull free from the vacuum pod, or the vacuum chamber may be flushed with sterile water or other fluids to expel the tissue from the pod. Once the tissue is free, the device is withdrawn leaving the geometry shown in FIGS. 57 and 57A, which is a cross-sectional view taken along line 57a-57b of FIG. 57. FIG. 57 is an illustrative view showing the longitudinal plication or dual fold sleeve 846 and the single fold of tissue 918 created by the restrictor stapler 900 to decrease the diameter of the distal outlet D0. The staple cartridge member may be reloaded with another removable staple cartridge 940 for another firing if necessary. Multiple plications may be positioned using the restrictor stapler 900 anywhere within the stomach cavity or newly created gastric sleeve or pouch. For example, three additional single folds of tissue 918 may be created near the distal outlet D0 created by the dual fold sleeve 846 as shown in FIG. 54.

By placing a single fold plication at the distal outlet D0 of the sleeve 400, the restrictor stapler 900 may reduce the diameter of the distal outlet from about 1.5 cm to about 0.5 cm. For example, in a wet lab test using canine tissue, a 19 mm diameter sleeve (57 Fr or 0.75 inch diameter) was reduced to 11.7 mm diameter (35 Fr or 0.46 inch diameter) by placing two restrictor plications adjacent to each other at the distal end of the 19 mm diameter sleeve. Therefore, these two restrictor plications removed 7.3 mm (22 Fr or 0.29 inch) from the sleeve diameter. The final size of the distal outlet was smaller than the perimeter of the stapler assembly. In a further example, the restrictor stapler places a plication that takes-up approximately 15 mm (0.59 inches) of circumferential tissue. This would yield approximately 4.8 mm diameter reduction (14.3 Fr or 0.188 inch diameter). The restrictor plication can have a variety of lengths, for example a length between about 0.25 inch to about 2 inch.

Figure 55:
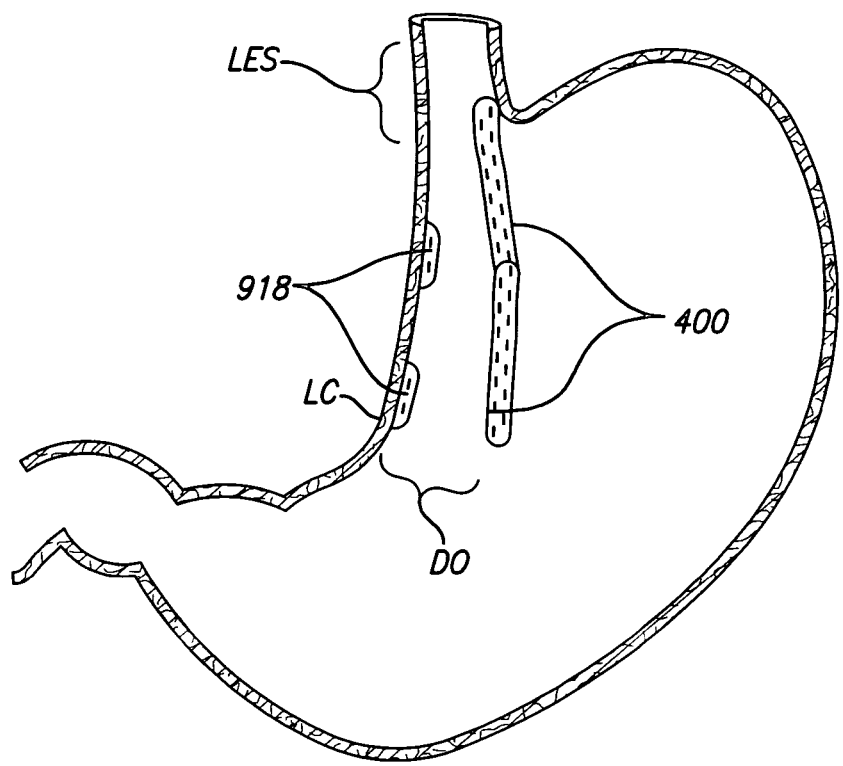
FIG. 55 shows an illustration of a stomach cavity with two dual fold plications forming a long sleeve and two single fold plications along the lesser curve to narrow the gastric sleeve.
Figure 56:
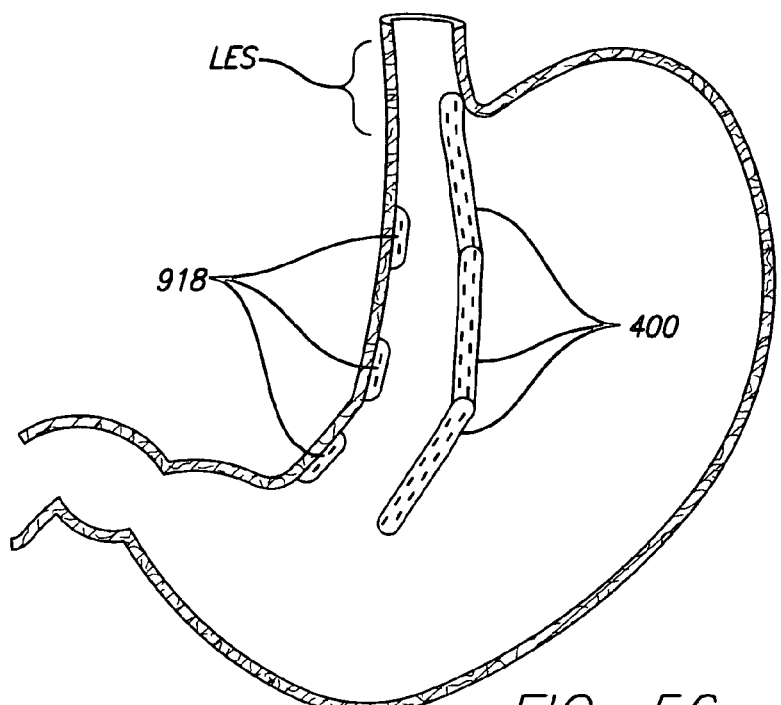
FIG. 56 shows an illustration of a stomach cavity with three dual fold plications forming a long sleeve and three single fold plications along the lesser curve to narrow the gastric sleeve.

The gastroplasty device 50 and the restrictor stapler 900 can be used together to form a variety of geometries, some of which are disclosed in U.S. patent application Ser. No. 11/107,382, which has already been incorporated by reference. In addition, multiple dual fold sleeves 400 may be placed consecutively in the stomach cavity to form a longer gastric sleeve, and multiple single folds of tissue 918 can be positioned within the longer gastric sleeve to reduce the diameter of the stoma. For example, FIG. 55 depicts two dual fold sleeves 400 placed consecutively in the stomach cavity, with two single folds of tissue 918 each placed near the distal end of the individual sleeves 400. FIG. 56 depicts three consecutively placed sleeves 400 and three single folds of tissue 918 each placed near the dial end of the individual sleeves 400. Although not shown, the single folds of tissue 918 can be placed anywhere along the lesser curve LC or circumferentially within the formed pouch to further restrict the diameter of the pouch. In another example as shown in FIG. 57, multiple sleeves 400 have been created within the stomach cavity from the GEJ to the pylorus. No single folds of tissue are shown in this example, however, it may be desirable to place multiple single folds of tissue along the lesser curve LC of the stomach.

In other embodiments, the distal outlet D0 of the gastric sleeve or pouch may be further restricted by cinching the distal stoma together as disclosed in U.S. patent application Ser. No. 11/056,327, which is hereby incorporated by reference in its entirety. In this embodiment, anchors may be placed circumferentially around the distal stoma, and then cinched together using a wire attached to all of the anchors. In another embodiment, an intragastric band may be placed at the distal outlet to further reduce its diameter as described in U.S. patent application Ser. No. 11/067,598, which is hereby incorporated by reference in its entirety. Here, the intragastric band is attached circumferentially around the distal outlet, and then the band itself cinches the distal outlet. It should be recognized that once the gastric sleeve or pouch is created, many methods may used to further restrict the diameter of the distal outlet created by the sleeve or pouch.

In describing the system and its components, certain terms have been used for understanding, brevity, and clarity. They are primarily used for descriptive purposes and are intended to be used broadly and construed in the same manner. Having now described the invention and its method of use, it should be appreciated that reasonable mechanical and operational equivalents would be apparent to those skilled in this art. Those variations are considered to be within the equivalence of the claims appended to the specification.

We claim:
1. A method for reducing the volume of a stomach cavity, comprising:
    inserting a tissue treatment device having a proximal end and a distal end transorally to the stomach cavity, the tissue treatment device having a first jaw opposite a second jaw and the first jaw being loaded with at least one fastener;

positioning the proximal end of the tissue treatment device within the stomach at the region of gastroesophageal junction and the distal end of the tissue treatment device within the stomach cavity;

acquiring tissue above a Z-line and from the stomach with the tissue treatment device; and forming a plication from the acquired tissue and extending downward into the body of the stomach using the at least one fastener loaded within the first jaw.

2. The method of claim 1, further comprising deploying a retractor disposed along the tissue treatment device and movable from a delivery configuration to a retraction configuration to manage stomach tissue relative to the tissue treatment device, allowing the acquired tissue from above the Z-line and from the stomach to be treated with the tissue treatment device.

3. The method of claim 2, further comprising extending a barrier disposed between the first jaw and the second jaw of the tissue treatment device and movable from a collapsed configuration to an extended configuration.

4. The method of claim 3, wherein extending the barrier between the first jaw and second jaw before acquiring tissue from above the Z-line and from the stomach with the tissue treatment device.

5. The method of claim 3, wherein the barrier is connected to the retractor.

6. The method of claim 3, further comprising removing the barrier from between the first jaw and the second jaw before forming the plication from the acquired tissue and extending downward into the body of the stomach.

7. The method of claim 6, wherein removing the barrier includes sliding the barrier past the distal end of the tissue treatment device.

8. The method of claim 7, wherein sliding the barrier includes moving a wire attached to the barrier distally.

9. The method of claim 2, wherein deploying the retractor pushes tissue away from the tissue treatment device.

10. The method of claim 1, further comprising viewing at least a portion of the acquiring tissue from above the Z-line and from the stomach with an endoscope.

11. The method of claim 1, wherein forming the plication from the acquired tissue and extending downward into the body of the stomach forms a pouch along the lesser curve of the stomach.

12. The method of claim 1, wherein acquiring tissue from above the Z-line and from the stomach using a vacuum generated within vacuum pods disposed within the tissue treatment device.

13. A method of providing therapy to the stomach cavity of a patient, comprising:

inserting at least a portion of a tissue treatment device within the stomach cavity; and forming a pouch extending downward from the gastroesophageal junction into the body of the stomach cavity by placing a first plication at least partially within the stomach cavity with the tissue treatment device, and the pouch having a distal outlet, wherein forming the pouch includes acquiring tissue from above a Z-line and from the stomach with the tissue treatment device.

14. The method of claim 13, wherein acquiring tissue from above the Z-line and from the stomach using a vacuum generated within vacuum pods disposed within the tissue treatment device.

15. The method of claim 13, further comprising positioning a restrictor device adjacent the distal outlet of the pouch and forming at least one restricting plication near the distal outlet of the pouch with the restrictor device reducing the size of the distal outlet.

16. The method of claim 15, wherein the restrictor device plicates a single fold of tissue.

17. The method of claim 13, wherein placing at least one restricting plication near the distal outlet of the pouch with the tissue treatment device.

18. The method of claim 13, further comprising positioning the tissue treatment device adjacent the distal outlet of the pouch and extending the length of the pouch by forming a second plication generally in-line with first plication.

19. The method of claim 18, wherein extending the length of the pouch the second plication at least partially overlaps the first plication.

20. The method of claim 18, wherein extending the length of the pouch includes aligning a septum disposed on the tissue treatment device with the first plication.

21. The method of claim 20, wherein aligning the septum with the first plication includes extending a retractor wire attached to the septum to extend the septum, and translating the septum along the tissue treatment device to come into contact with a distal end of the first plication.

22. The method of claim 13, wherein forming the pouch with the tissue treatment device, the tissue treatment device plicates a dual fold of tissue.

23. A method of providing therapy to the stomach cavity of a patient, comprising:

inserting at least a portion of a tissue treatment device within the stomach cavity;

forming a first plication with the tissue treatment device, the first plication extending downward from the gastroesophageal junction into the stomach cavity, and wherein forming the first plication includes acquiring tissue from above a Z-line and from the stomach with the tissue treatment device to form the first plication;

repositioning the tissue treatment device near a distal end of the first plication; and forming a second plication near the first plication with the tissue treatment device, wherein the first and second plications form a pouch along a lesser curve of the stomach with a distal outlet.

24. The method of claim 23, wherein forming the second plication generally in-line with the first plication.

25. The method of claim 23, further comprising positioning a restrictor device adjacent the distal outlet of the pouch and forming at least one restricting application near the distal outlet of the pouch with the restrictor device reducing the size of the distal outlet.

26. The method of claim 25, further comprising repositioning the restrictor device within the pouch and forming multiple restricting plications within the pouch.

27. The method of claim 23, further comprising positioning a restrictor device between the first plication and the second plication and forming a restricting plication to close a stoma between the first plication and the second plication.

28. The method of claim 23, wherein forming the second plication with the tissue treatment device, the second plication is continuous with the first plication.

29. The method of claim 23, wherein forming the second plication with the tissue treatment device, the second plication overlaps the distal end of the first plication.

\* \* \* \* \*